US009382297B2

(12) United States Patent
Honda et al.

(10) Patent No.: US 9,382,297 B2
(45) Date of Patent: Jul. 5, 2016

(54) MUTATED PROTEIN OF PROTEIN A HAVING REDUCED AFFINITY IN ACIDIC REGION AND ANTIBODY-CAPTURING AGENT

(71) Applicant: NAT'L INSTITUTE OF ADVANCED INDUSTRIAL SCIENCE AND TECHNOLOGY, Tsukuba-shi, Ibaraki (JP)

(72) Inventors: Shinya Honda, Tsukuba (JP); Hideki Watanabe, Tsukuba (JP); Masayuki Tsukamoto, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 14/095,638

(22) Filed: Dec. 3, 2013

(65) Prior Publication Data

US 2014/0179898 A1 Jun. 26, 2014

Related U.S. Application Data

(63) Continuation of application No. PCT/JP2012/064072, filed on May 31, 2012.

(30) Foreign Application Priority Data

Jun. 3, 2011 (JP) ................................. 2011-124916

(51) Int. Cl.
*C07K 14/00* (2006.01)
*C07K 14/005* (2006.01)
*C07K 1/22* (2006.01)
*C07K 14/31* (2006.01)

(52) U.S. Cl.
CPC ................. *C07K 14/005* (2013.01); *C07K 1/22* (2013.01); *C07K 14/00* (2013.01); *C07K 14/31* (2013.01); *C07K 2319/705* (2013.01)

(58) Field of Classification Search
CPC ...... C07K 14/00; C07K 14/005; C07K 14/31; C07K 1/22; C07K 2319/705
See application file for complete search history.

(56) References Cited

U.S. PATENT DOCUMENTS

| 3,995,018 A | 11/1976 | Sjoquist |
| 2012/0208234 A1 | 8/2012 | Yoshida et al. |
| 2014/0179898 A1* | 6/2014 | Honda et al. ................... 530/324 |

FOREIGN PATENT DOCUMENTS

| EP | 2202310 A2 | 6/2010 |
| JP | 63-258500 A | 10/1988 |
| JP | 63-267281 A | 11/1988 |
| JP | 2010-081866 A | 4/2010 |
| WO | 2010-110288 A1 | 9/2010 |
| WO | WO 2011005341 A2 * | 1/2011 ........... A61K 39/085 |

OTHER PUBLICATIONS

Maghnus O'Seaghdha, *Staphylococcus aureus* protein A binding to von Willebrand factor A1 domain is mediated by conserved IgG binding regions, FEBS Journal 273 (2006) 4831-4841, 2006.*
English Translation of the Description of JP2010-081866, accessed on Jan. 22, 2015.*
Graille et al.; "Crystal structure of a *Staphylococcus aureus* protein A domain complexed with the Fab fragment of a human IgM antibody: Structural basis for recognition of B-cell receptors and superantigen activity"; PNAS; May 9, 2000; pp. 5399-5404; vol. 97, No. 10; www.pnas.org.
Jansson et al.; "All individual domains of staphylococcal protein A show Fab binding"; FEMS Immunology and Medical Microbiology; 1998; pp. 69-78; vol. 20; Elsevier Science B.V.
International Search Report of PCT/JP2012/064072, mailing date of Jul. 10, 2012.
Foresgren, A. et al., "'Protein A' from *S. aureus*: I. Pseudo-Immune Reaction with Human g-Globulin", The Journal of Immunology, 1966, vol. 97, No. 6, pp. 822-827.
Boyle, M. D.P., Bacterial Immunoglobulin Binding Proteins, vol. 1, pp. 29-38, cited in specification, 1990.
Tashiro, Mitsuru et al., "Structures of bacterial immunoglobulin-binding domains and their complexes with immunoglobulins", Current Opinion in Structural Biology, 1995, vol. 5, pp. 471-481, cited in specification.
Gagnon, Pete, Purification Tools for Monoclonal Antibodies, 1996, pp. 155-186, cited in specification.
Watanabe, Hideki et al., "Rational design of a pH-sensitive affinity ligand by introduction of electrostatic repulsion into a binding interface", Dai 9 Kai Protein Science Society of Japan Nenkai Program Yoshishu, 2009, p. 151, cited in ISR.
Tsukamoto, Masayuki et al., "Enhancement of pH Sensitivity of Protein A used for antibody Purification", Dai 11 Kai Proetein Science Society of Japan Nenkai Program Yoshishu, 2011, p. 107, cited in ISR.

(Continued)

*Primary Examiner* — James H Alstrum Acevedo
*Assistant Examiner* — Erinne Dakowski
(74) *Attorney, Agent, or Firm* — Westerman, Hattori, Daniels & Adrian LLP

(57) ABSTRACT

A modified protein of an extracellular domain of protein A, which has the reduced ability to bind to immunoglobulin in an acidic region, compared with the wild-type extracellular domain of protein A, without impairing a selective antibody-binding activity in a neutral region. On the basis of three-dimensional structure coordinate data on a complex of the extracellular domain of protein A bound with the Fc region of immunoglobulin G, the modified protein is obtained by the substitution of amino acid residues that are located within the range of 10 angstroms from the Fc region and have a 20% or more ratio of exposed surface area, by histidine residues. Preferably, the modified protein is obtained by the substitution of amino acid residues at sites identified from the analysis of sequences selected from a library constituted by the protein group, by histidine residues. These substitutions may be combined.

20 Claims, 10 Drawing Sheets

(56) References Cited

OTHER PUBLICATIONS

Hirota, Kiyonori et al., "Kotai Iyakuhin no Tameno Tailor-Made Seisei Gijutsu Kaihatsu", Chemical Engineering, 2011, vol. 56, No. 4, pp. 293-299, cited in ISR.

Brown, Nicola L. et al., "A Study of the Interactions Between an IgG-Binding Domain Based on the B Domain of Staphylococcal Protein A and Rabbit IgG", Molecular Biology, 1998, vol. 10, No. 1, pp. 9-16, cited in ISR.

Gore, Michael G. et al., "pH-sensitive interactions between IgG and a mutated IgG-binding protein based upon two B domains of Protein A from *Staphylococcus aureus*", Protein Engineering, 1992, vol. 5, No. 6, pp. 577-582, cited in ISR.

* cited by examiner

```
E domain  NAAQHDEAQQNAFYQVLNMPNLNADQRNGFIQSLKDDPSQSANVLGEAQKLNDSQAPK
D domain  QQNNFNKDQQSAFYEILNMPNLNEAQRNGFIQSLKDDPSQSTNVLGEAKKLNESQAPK
A domain  ADNNFNKEQQNAFYEILNMPNLNEEQRNGFIQSLKDDPSQSANLLSEAKKLNESQAPK
B domain  ADNKFNKEQQNAFYEILHLPNLNEEQRNGFIQSLKDDPSQSANLLAEAKKLNDAQAPK
C domain  ADNKFNKEQQNAFYEILHLPNLTEEQRNGFIQSLKDDPSVSKEILAEAKKLNDAQAPK Z domain  VDNKFNKEQQNAFYEILHLPNLNEEQRNAFIQSLKDDPSQSANLLAEAKKLNDAQAPK
```

FIG. 2

\>gi|87201381:73429-74979 Staphylococcus aureus subsp. aureus NCTC 8325, complete genome reverse complement
ttgaaaaagaaaaacatttattcaattcgtaaactaggtgtaggtattgcatctgtaact
ttaggtacattacttatatctggtggcgtaacacctgctgcaaatgctgcgcaacacgat
gaagctcaacaaaatgcttttttatcaagtcttaaatatgcctaacttaaatgctgatcaa
cgcaatggttttatccaaagccttaaagatgatccaagccaaagtgctaacgttttaggt
gaagctcaaaaacttaatgactctcaagctccaaaagctgatgcgcaacaaaataacttc
aacaaagatcaacaaagcgccttctatgaaatcttgaacatgcctaacttaaacgaagcg
caacgtaacggcttcattcaaagtcttaaagacgacccaagccaaagcactaacgtttta
ggtgaagctaaaaaattaaacgaatctcaagcaccgaaagctgataacaatttcaacaaa
gaacaacaaaatgctttctatgaaatcttgaatatgcctaacttaaacgaagaacaacgc
aatggtttcatccaaagcttaaaagatgacccaagccaaagtgctaacctattgtcagaa
gctaaaaagttaaatgaatctcaagcaccgaaagcggataacaaattcaacaaagaacaa
caaaatgctttctatgaaatcttacatttacctaacttaaacgaagaacaacgcaatggt
ttcatccaaagcctaaaagatgacccaagccaaagcgctaaccttttagcagaagctaaa
aagctaaatgatgctcaagcaccaaaagctgacaacaaattcaacaaagaacaacaaaat
gctttctatgaaattttacatttacctaacttaactgaagaacaacgtaacggcttcatc
caaagccttaaagacgatccttcagtgagcaaagaaatttagcagaagctaaaaagcta
aacgatgctcaagcaccaaaagaggaagacaataacaagcctggcaaagaagacaataac
aagcctggcaaagaagacaacaacaagcctggtaaagaagacaacaacaagcctggtaaa
gaagacaacaacaagcctggcaaagaagacggcaacaagcctggtaaagaagacaacaaa
aaacctggtaaagaagatggcaacaagcctggtaaagaagacaacaaaaaacctggtaaa
gaagacggcaacaagcctggcaaagaagatggcaacaaacctggtaaagaagatggtaac
ggagtacatgtcgttaaacctggtgatacagtaaatgacattgcaaaagcaaacggcact
actgctgacaaaattgctgcagataacaaattagctgataaaaacatgatcaaacctggt
caagaacttgttgttgataagaagcaaccagcaaaccatgcagatgctaacaaagctcaa
gcattaccagaaactggtgaagaaaatccattcatcggtacaactgtatttggtggatta
tcattagccttaggtgcagcgttattagctggacgtcgtgcgaactataa

FIG. 3

The B domain is depicted as a surface model, and the Fc region is depicted as a ribbon model.

17 amino acid residues (Phe5, Asn6, Gln9, Gln10, Asn11, Phe13, Tyr14, Glu15, Leu17, His18, Glu24, Glu25, Arg27, Asn28, Ile31, Gln32, Lys35, and Asp36) of the B domain selected as sites to be mutated are indicated in gray.

Pattern of elution of human monoclonal antibody by pH-gradient affinity chromatography
The solid line represents absorbance at 280 nm (left axis). The dotted line represents pH (right axis).
(A) M-PAZ01-immobilized column  (B) M-PAB02-immobilized column
(C) M-PAB03-immobilized column  (D) HiTrap™ rProtein A FF (GE Healthcare)

Pattern of elution of human monoclonal antibody by stepwise affinity chromatography
The solid line represents absorbance at 280 nm (left axis). The dotted line represents pH (right axis).
(A)M-PAZ01-immobilized column(elution at pH 4.0) (B)M-PAB02-immobilized column(elution at pH 4.0)
(C)M-PAB03-immobilized column(elution at pH 4.0) (D)HiTrap™ rProtein A FF (GE Healthcare)

Pattern of elution of human monoclonal antibody by pH-gradient affinity chromatography. The solid line represents absorbance at 280 nm (left axis). The dotted line represents pH (right axis). (A) M-PA801-immobilized column (B) M-PA807-immobilized column (C) M-PA808M-immobilized column (D) M-PA809-immobilized column Pattern of elution of human monoclonal antibody by pH-gradient affinity chromatography. The solid line represents absorbance at 280 nm (left axis). The dotted line represents pH (right axis). (A) M-PAB10-immobilized column (B) M-PAB13-immobilized column (C) M-PAB14-immobilized column (D) M-PAB15-immobilized column Pattern of elution of human monoclonal antibody by pH-gradient affinity chromatography. The solid line represents absorbance at 280 nm (left axis). The dotted line represents pH (right axis). (A) M-PAC01-immobilized column (B) M-PAC08-immobilized column (C) M-PAC09-immobilized column (D) M-PAC13-immobilized column

MUTATED PROTEIN OF PROTEIN A HAVING REDUCED AFFINITY IN ACIDIC REGION AND ANTIBODY-CAPTURING AGENT

TECHNICAL FIELD

The present invention relates to a novel modified protein of an extracellular domain of protein A which is an antibody-binding protein, a nucleic acid encoding the protein, and an antibody-capturing agent that exploits the ability of the protein to bind to antibodies.

BACKGROUND ART

Protein A, a *Staphylococcus aureus*-derived protein, is known to have affinity for constant regions of antibodies immunoglobulin G, immunoglobulin A, and immunoglobulin M (Non Patent Literatures 1 and 2).

The protein A is a multidomain membrane protein composed of a plurality of domains. Of these domains, some extracellular domains exhibit a binding activity to proteins having a constant region of immunoglobulin (hereinafter, referred to as an antibody-binding activity) (Non Patent Literature 2). For example, in the case of NCTC8325 strain-derived protein A shown in FIGS. 1 and 3, five domains, i.e., E, D, A, B, and C domains, exhibit the antibody-binding activity. These domains are small proteins each having a little less than 60 amino acids and exhibit high homology among their amino acid sequences (FIG. 2). It is also known that each domain isolated by the cleavage of protein A maintains the antibody-binding activity in itself (Non Patent Literature 3).

Meanwhile, a Z domain is an artificial protein synthesized on the basis of the sequence of the B domain (Non Patent Literature 3) and differs from the B domain by two amino acid residues (FIG. 2). These two substitutions of AlalVal and Gly29Ala are known to stabilize the structure, though the substitutions do not cancel the ability to bind to antibodies. The thermal denaturation temperature thereof is approximately 90° C. (Non Patent Literature 3).

The extracellular domains (E, D, A, B, and C) of protein A and the Z domain are currently commercially available as many products that exploit their selective antibody-binding activities (e.g., carriers for affinity chromatography for antibody purification (Patent Literatures 1 and 2) and test reagents for antibody detection, research reagents, etc.). The binding strength of each extracellular domain of protein A with antibodies is known to be high in a neutral region and low in a strongly acidic region (Non Patent Literature 4).

For the purpose of antibody isolation, recovery, and purification, an antibody-containing sample solution such as serum is first rendered neutral and contacted with a protein A extracellular domain-immobilized water-insoluble solid-phase support (e.g., beads) to selectively adsorb the antibodies thereon. Then, the support is washed with a neutral solution of pH 7 to remove components other than the antibodies. Finally, a strongly acidic solution of pH 3.0 is generally added thereto to desorb the antibodies from the antibody-bound protein A, followed by elution of the antibodies together with the strongly acidic solution (Patent Literatures 1, 2, and 3). In this way, the antibodies can be isolated, recovered, and purified with high purity.

The antibodies, however, may be deteriorated in a strongly acidic solution having a pH of approximately 3.0, due to denaturation, aggregation, or the like and may lose its original functions, depending on the types of the antibodies (Non Patent Literature 4). In order to prevent this problem, the elution treatment has been attempted in a weakly acidic region higher than pH 3.0. In this weakly acidic region, the antibodies cannot be eluted from protein A due to the strong binding strength of the protein A extracellular domains with the antibodies and thus, cannot be recovered in sufficient amounts.

Thus, the inventors disclosed the modification of protein A in Patent Literature 4. Specifically, the object of the study therein was to provide a modified protein of an extracellular domain of protein A having the reduced ability to bind to the Fc region of immunoglobulin in a weakly acidic region, compared with the wild-type extracellular domain of protein A, without impairing a high antibody-binding activity in a neutral region. On the basis of three-dimensional structure coordinate data on a complex of each extracellular domain of protein A bound with the Fc region of immunoglobulin G, the modified protein was obtained by the substitution of amino acid residues that were located within the range of 6.5 angstroms from the Fc region and had a 35% or more ratio of exposed surface area, by histidine residues. These substitutions may be combined.

Since the influence of amino acid substitutions on protein functions may however cause unexpected change, it is desirable to experimentally confirm the effects of each individual amino acid substitution. Thus, in the three-dimensional structure coordinate data on a complex of each extracellular domain of protein A bound with the Fc region of immunoglobulin G, amino acid residues that were located within the range of 10.0 angstroms from the Fc region and had a 20% or more ratio of exposed surface area were targeted to prepare a molecular library containing comprehensive combinations of these residues substituted by histidine residues. Effective sequences were selected from among approximately 260,000 molecular species, and the frequency of their appearance was further analyzed statistically to experimentally confirm the effects of each individual amino acid substitution. Then, specific substitution-mutated protein A was prepared. While actual activity was confirmed, more effective modification of protein A was continued. As a result, the present invention has been completed.

CITATION LIST

Patent Literature

Patent Literature 1: U.S. Pat. No. 3,995,018
Patent Literature 2: Japanese Patent Laid-Open No. 63-258500
Patent Literature 3: Japanese Patent Laid-Open No. 63-267281
Patent Literature 4: Japanese Patent Laid-Open No. 2010-81866

Non Patent Literature

Non Patent Literature 1: Forsgren A and Sjoquist J (1966) "Protein A" from *S. Aureus*. J. Immunol. 97, 822-827.
Non Patent Literature 2: Boyle M. D. P., Ed. (1990) Bacterial Immunoglobulin Binding Proteins. Academic Press, Inc., San Diego, Calif., USA.
Non Patent Literature 3: Tashiro M, Montelione G T. (1995) Structures of bacterial immunoglobulin-binding domains and their complexes with immunoglobulins. Curr Opin Struct *Biol.* 5, 471-481.
Non Patent Literature 4: Gagnon P. (1996) Purification Tools for Monoclonal Antibodies, Validated Biosystems Inc., Tucson, Ariz., USA.

SUMMARY OF INVENTION

Technical Problem

An object of the present invention is to solve the problems of the conventional techniques and, more specifically, to provide a modified protein having the reduced ability to bind to a constant region of immunoglobulin in an acidic region, compared with the wild-type extracellular domain of protein A, without impairing a selective antibody-binding activity in a neutral region and to enable antibodies to be easily captured and recovered using this modified protein without denaturing the antibodies.

Solution to Problem

The present inventors have hypothesized that the deterioration of antibodies by a strong acid during the acid elution of the antibodies from a protein A extracellular domain-immobilized solid-phase support can be prevented by modifying the amino acid sequence of the protein A extracellular domain so as to permit elution from the solid-phase support using a weakly acidic solution. As a result of conducting diligent studies, the present inventors have constructed a method for designing the sequence of a novel protein A mutant, whereby the modified protein has the ability to bind to immunoglobulin constant regions in a neutral region at the same level as in wild-type protein A and has the largely reduced ability to bind to antibodies in an acidic region, compared with wild-type protein A. Then, the mutated protein synthesized on the basis of the design has been confirmed to have physical properties as intended. As a result, the present invention has been completed.

(1)

A mutant protein derived from the B domain protein of protein A of the amino acid sequence set forth in SEQ ID NO: 1, the mutant protein having any of the following amino acid sequences according to (a) to (c), having a binding activity to a constant region of immunoglobulin, and having a reduced binding activity in an acidic region to the constant region of immunoglobulin, compared with the wild-type B domain of protein A:

(a) an amino acid sequence derived from the amino acid sequence set forth in SEQ ID NO: 1 by the substitution of any one or more amino acid residues of Phe5, Asn6, Gln9, Gln10, Asn11, Phe13, Tyr14, Glu15, Leu17, Glu24, Glu25, Arg27, Asn28, Ile31, Gln32, Lys35, and Asp36 by a histidine residue;

(b) a mutant protein consisting of an amino acid sequence derived from the histidine-substituted amino acid sequence according to (a) by the addition or insertion of one or several amino acid residues; and (c) a mutant protein consisting of an amino acid sequence derived from the histidine-substituted amino acid sequence according to (a) or (b) by the deletion or substitution of one or several amino acid residues other than the histidine residue-substituted site(s).

(2)

A mutant protein derived from the Z domain protein of protein A of the amino acid sequence set forth in SEQ ID NO: 2, the mutant protein having any of the following amino acid sequences according to (a) to (c), having a binding activity to a constant region of immunoglobulin, and having a reduced binding activity in an acidic region to the constant region of immunoglobulin, compared with the Z domain of protein A:

(a) an amino acid sequence derived from the amino acid sequence set forth in SEQ ID NO: 2 by the substitution of any one or more amino acid residues of Phe5, Asn6, Gln9, Gln10, Asn11, Phe13, Tyr14, Glu15, Leu17, Glu24, Glu25, Arg27, Asn28, Ile31, Gln32, Lys35, and Asp36 by a histidine residue;

(b) a mutant protein consisting of an amino acid sequence derived from the histidine-substituted amino acid sequence according to (a) by the addition or insertion of one or several amino acid residues; and (c) a mutant protein consisting of an amino acid sequence derived from the histidine-substituted amino acid sequence according to (a) or (b) by the deletion or substitution of one or several amino acid residues other than the histidine residue-substituted site(s).

(3)

A mutant protein derived from the E domain protein of protein A of the amino acid sequence set forth in SEQ ID NO: 3, the mutant protein having any of the following amino acid sequences according to (a) to (c), having a binding activity to a constant region of immunoglobulin, and having a reduced binding activity in an acidic region to the constant region of immunoglobulin, compared with the wild-type E domain of protein A:

(a) an amino acid sequence derived from the amino acid sequence set forth in SEQ ID NO: 3 by the substitution of any one or more amino acid residues of Asp6, Gln9, Gln10, Asn11, Phe13, Tyr14, Gln15, Leu17, Asn18, Ala24, Asp25, Arg27, Asn28, Ile31, Gln32, Lys35, and Asp36 by a histidine residue;

(b) a mutant protein consisting of an amino acid sequence derived from the histidine-substituted amino acid sequence according to (a) by the addition or insertion of one or several amino acid residues; and (c) a mutant protein consisting of an amino acid sequence derived from the histidine-substituted amino acid sequence according to (a) or (b) by the deletion or substitution of one or several amino acid residues other than the histidine residue-substituted site(s).

(4)

A mutant protein derived from the D domain protein of protein A of the amino acid sequence set forth in SEQ ID NO: 4, the mutant protein having any of the following amino acid sequences according to (a) to (c), having a binding activity to a constant region of immunoglobulin, and having a reduced binding activity in an acidic region to the constant region of immunoglobulin, compared with the wild-type D domain of protein A:

(a) an amino acid sequence derived from the amino acid sequence set forth in SEQ ID NO: 4 by the substitution of any one or more amino acid residues of Phe5, Asn6, Gln9, Gln10, Ser11, Phe13, Tyr14, Glu15, Leu17, Asn18, Glu24, Ala25, Arg27, Asn28, Ile31, Gln32, Lys35, and Asp36 by a histidine residue;

(b) a mutant protein consisting of an amino acid sequence derived from the histidine-substituted amino acid sequence according to (a) by the addition or insertion of one or several amino acid residues; and (c) a mutant protein consisting of an amino acid sequence derived from the histidine-substituted amino acid sequence according to (a) or (b) by the deletion or substitution of one or several amino acid residues other than the histidine residue-substituted site(s).

(5)

A mutant protein derived from the A domain protein of protein A of the amino acid sequence set forth in SEQ ID NO: 5, the mutant protein having any of the following amino acid sequences according to (a) to (c), having a binding activity to a constant region of immunoglobulin, and having a reduced binding activity in an acidic region to the constant region of immunoglobulin, compared with the wild-type A domain of protein A:
(a) an amino acid sequence derived from the amino acid sequence set forth in SEQ ID NO: 5 by the substitution of any one or more amino acid residues of Phe5, Asn6, Gln9, Gln10, Asn11, Phe13, Tyr14, Glu15, Leu17, Asn18, Glu24, Glu25, Arg27, Asn28, Ile31, Gln32, Lys35, and Asp36 by a histidine residue;
(b) a mutant protein consisting of an amino acid sequence derived from the histidine-substituted amino acid sequence according to (a) by the addition or insertion of one or several amino acid residues; and
(c) a mutant protein consisting of an amino acid sequence derived from the histidine-substituted amino acid sequence according to (a) or (b) by the deletion or substitution of one or several amino acid residues other than the histidine residue-substituted site(s).

(6)
A mutant protein derived from the C domain protein of protein A of the amino acid sequence set forth in SEQ ID NO: 6, the mutant protein having any of the following amino acid sequences according to (a) to (c), having a binding activity to a constant region of immunoglobulin, and having a reduced binding activity in an acidic region to the constant region of immunoglobulin, compared with the wild-type C domain of protein A:
(a) an amino acid sequence derived from the amino acid sequence set forth in SEQ ID NO: 6 by the substitution of any one or more amino acid residues of Phe5, Asn6, Gln9, Gln10, Asn11, Phe13, Tyr14, Glu15, Leu17, Glu24, Glu25, Arg27, Asn28, Ile31, Gln32, Lys35, and Asp36 by a histidine residue;
(b) a mutant protein consisting of an amino acid sequence derived from the histidine-substituted amino acid sequence according to (a) by the addition or insertion of one or several amino acid residues; and
(c) a mutant protein consisting of an amino acid sequence derived from the histidine-substituted amino acid sequence according to (a) or (b) by the deletion or substitution of one or several amino acid residues other than the histidine residue-substituted site(s).

(7)
A mutant protein derived from the B domain protein of protein A of the amino acid sequence set forth in SEQ ID NO: 1, the mutant protein having any of the following amino acid sequences according to (a) to (c), having a binding activity to a constant region of immunoglobulin, and having a reduced binding activity in an acidic region to the constant region of immunoglobulin, compared with the wild-type B domain of protein A:
(a) an amino acid sequence derived from the amino acid sequence set forth in SEQ ID NO: 1 by the substitution of any one or more amino acid residues of Phe5, Gln9, Gln10, Asn11, Glu15, Arg27, Asn28, Lys35, and Asp36 by a histidine residue;
(b) a mutant protein consisting of an amino acid sequence derived from the histidine-substituted amino acid sequence according to (a) by the addition or insertion of one or several amino acid residues; and
(c) a mutant protein consisting of an amino acid sequence derived from the histidine-substituted amino acid sequence according to (a) or (b) by the deletion or substitution of one or several amino acid residues other than the histidine residue-substituted site(s).

(8)
A mutant protein derived from the Z domain protein of protein A of the amino acid sequence set forth in SEQ ID NO: 2, the mutant protein having any of the following amino acid sequences according to (a) to (c), having a binding activity to a constant region of immunoglobulin, and having a reduced binding activity in an acidic region to the constant region of immunoglobulin, compared with the Z domain of protein A:
(a) an amino acid sequence derived from the amino acid sequence set forth in SEQ ID NO: 2 by the substitution of any one or more amino acid residues of Phe5, Gln9, Gln10, Asn11, Glu15, Arg27, Asn28, Lys35, and Asp36 by a histidine residue;
(b) a mutant protein consisting of an amino acid sequence derived from the histidine-substituted amino acid sequence according to (a) by the addition or insertion of one or several amino acid residues; and
(c) a mutant protein consisting of an amino acid sequence derived from the histidine-substituted amino acid sequence according to (a) or (b) by the deletion or substitution of one or several amino acid residues other than the histidine residue-substituted site(s).

(9)
A mutant protein derived from the E domain protein of protein A of the amino acid sequence set forth in SEQ ID NO: 3, the mutant protein having any of the following amino acid sequences according to (a) to (c), having a binding activity to a constant region of immunoglobulin, and having a reduced binding activity in an acidic region to the constant region of immunoglobulin, compared with the wild-type E domain of protein A:
(a) an amino acid sequence derived from the amino acid sequence set forth in SEQ ID NO: 3 by the substitution of any one or more amino acid residues of Gln9, Gln10, Asn11, Gln15, Asn18, Arg27, Asn28, Lys35, and Asp36 by a histidine residue;
(b) a mutant protein consisting of an amino acid sequence derived from the histidine-substituted amino acid sequence according to (a) by the addition or insertion of one or several amino acid residues; and
(c) a mutant protein consisting of an amino acid sequence derived from the histidine-substituted amino acid sequence according to (a) or (b) by the deletion or substitution of one or several amino acid residues other than the histidine residue-substituted site(s).

(10)
A mutant protein derived from the D domain protein of protein A of the amino acid sequence set forth in SEQ ID NO: 4, the mutant protein having any of the following amino acid sequences according to (a) to (c), having a binding activity to a constant region of immunoglobulin, and having a reduced binding activity in an acidic region to the constant region of immunoglobulin, compared with the wild-type D domain of protein A:
(a) an amino acid sequence derived from the amino acid sequence set forth in SEQ ID NO: 4 by the substitution of any one or more amino acid residues of Phe5, Gln9, Gln10, Ser11, Glu15, Asn18, Arg27, Asn28, Lys35, and Asp36 by a histidine residue;
(b) a mutant protein consisting of an amino acid sequence derived from the histidine-substituted amino acid sequence according to (a) by the addition or insertion of one or several amino acid residues; and
(c) a mutant protein consisting of an amino acid sequence derived from the histidine-substituted amino acid sequence according to (a) or (b) by the deletion or substitution of one or several amino acid residues other than the histidine residue-substituted site(s).

(11)
A mutant protein derived from the A domain protein of protein A of the amino acid sequence set forth in SEQ ID NO: 5, the mutant protein having any of the following amino acid sequences according to (a) to (c), having a binding activity to a constant region of immunoglobulin, and having a reduced binding activity in an acidic region to the constant region of immunoglobulin, compared with the wild-type A domain of protein A:
(a) an amino acid sequence derived from the amino acid sequence set forth in SEQ ID NO: 5 by the substitution of any one or more amino acid residues of Phe5, Gln9, Gln10, Asn11, Glu15, Asn18, Arg27, Asn28, Lys35, and Asp36 by a histidine residue;
(b) a mutant protein consisting of an amino acid sequence derived from the histidine-substituted amino acid sequence according to (a) by the addition or insertion of one or several amino acid residues; and
(c) a mutant protein consisting of an amino acid sequence derived from the histidine-substituted amino acid sequence according to (a) or (b) by the deletion or substitution of one or several amino acid residues other than the histidine residue-substituted site(s).

(12)
A mutant protein derived from the C domain protein of protein A of the amino acid sequence set forth in SEQ ID NO: 6, the mutant protein having any of the following amino acid sequences according to (a) to (c), having a binding activity to a constant region of immunoglobulin, and having a reduced binding activity in an acidic region to the constant region of immunoglobulin, compared with the wild-type C domain of protein A:
(a) an amino acid sequence derived from the amino acid sequence set forth in SEQ ID NO: 6 by the substitution of any one or more amino acid residues of Phe5, Gln9, Gln10, Asn11, Glu15, Arg27, Asn28, Lys35, and Asp36 by a histidine residue;
(b) a mutant protein consisting of an amino acid sequence derived from the histidine-substituted amino acid sequence according to (a) by the addition or insertion of one or several amino acid residues; and
(c) a mutant protein consisting of an amino acid sequence derived from the histidine-substituted amino acid sequence according to (a) or (b) by the deletion or substitution of one or several amino acid residues other than the histidine residue-substituted site(s).

(13)
A mutant protein derived from the B domain protein of protein A of the amino acid sequence set forth in SEQ ID NO: 1, the mutant protein having any of the following amino acid sequences according to (a) to (c), having a binding activity to a constant region of immunoglobulin, and having a reduced binding activity in an acidic region to the constant region of immunoglobulin, compared with the wild-type B domain of protein A:
(a) an amino acid sequence set forth in any of SEQ ID NOs: 7, 8, 10 to 12, 15, 20 to 23, and 25 to 27;
(b) an amino acid sequence derived from the amino acid sequence according to (a) by the insertion or addition of one or several amino acid residues; and
(c) an amino acid sequence derived from the amino acid sequence according to (a) or (b) by the deletion or substitution of one or several amino acid residues other than histidine residue-substituted site(s).

(14)
A mutant protein derived from the B domain protein of protein A of the amino acid sequence set forth in SEQ ID NO: 1, the mutant protein having any of the following amino acid sequences according to (a) to (c), having a binding activity to a constant region of immunoglobulin, and having a reduced binding activity in an acidic region to the constant region of immunoglobulin, compared with the wild-type B domain of protein A:
(a) an amino acid sequence set forth in any of SEQ ID NOs: 13, 14, 16 to 19, 24, and 61 to 71;
(b) an amino acid sequence derived from the amino acid sequence according to (a) by the insertion or addition of one or several amino acid residues; and
(c) an amino acid sequence derived from the amino acid sequence according to (a) or (b) by the deletion or substitution of one or several amino acid residues other than histidine residue-substituted site(s).

(15)
A mutant protein derived from the Z domain protein of protein A of the amino acid sequence set forth in SEQ ID NO: 2, the mutant protein having any of the following amino acid sequences according to (a) to (c), having a binding activity to a constant region of immunoglobulin, and having a reduced binding activity in an acidic region to the constant region of immunoglobulin, compared with the Z domain of protein A:
(a) an amino acid sequence set forth in SEQ ID NO: 9 or 72;
(b) an amino acid sequence derived from the amino acid sequence according to (a) by the insertion or addition of one or several amino acid residues; and
(c) an amino acid sequence derived from the amino acid sequence according to (a) or (b) by the deletion or substitution of one or several amino acid residues other than histidine residue-substituted site(s).

(16)
A mutant protein derived from the C domain protein of protein A of the amino acid sequence set forth in SEQ ID NO: 6, the mutant protein having any of the following amino acid sequences according to (a) to (c), having a binding activity to a constant region of immunoglobulin, and having a reduced binding activity in an acidic region to the constant region of immunoglobulin, compared with the C domain of protein A:
(a) an amino acid sequence set forth in any of SEQ ID NOs: 74 to 76;
(b) an amino acid sequence derived from the amino acid sequence according to (a) by the insertion or addition of one or several amino acid residues; and
(c) an amino acid sequence derived from the amino acid sequence according to (a) or (b) by the deletion or substitution of one or several amino acid residues other than histidine residue-substituted site(s).

(17)
A tandem-type protein comprising an amino acid sequence in which the amino acid sequence of a protein according to any one of items (1) to (16) and an arbitrary amino acid sequence are alternately arranged.

(18)
A fusion protein comprising an amino acid sequence in which the amino acid sequence of a protein according to any one of items (1) to (17) is linked to an amino acid sequence of an additional protein.

(19)
A spacer-attached protein comprising an amino acid sequence in which the amino acid sequence of a protein according to any one of items (1) to (18) is linked to an amino acid sequence of a spacer for immobilizing the protein onto a water-insoluble solid-phase support.

(20)
A nucleic acid encoding a protein according to any one of items (1) to (19).

(21)

The nucleic acid according to item (20), wherein the nucleic acid comprises a nucleotide sequence set forth in any of SEQ ID NOs: 28 to 30, 43 to 60, and 77 to 91.

(22)

A nucleic acid which hybridizes under stringent conditions to a nucleic acid comprising a sequence complementary to the nucleotide sequence of a nucleic acid according to item (20) or (21) and encodes a mutant protein having a binding activity to a constant region of immunoglobulin and having a reduced binding activity in an acidic region to the constant region of immunoglobulin, compared with the wild-type antibody-binding domain of protein A.

(23)

A recombinant vector comprising a nucleic acid according to any one of items (20) to (22).

(24)

A transformant comprising a recombinant vector according to item (23) introduced therein.

(25)

An immobilized protein comprising a protein according to any one of items (1) to (19) immobilized on a water-insoluble solid-phase support.

(26)

A capturing agent for an antibody, immunoglobulin G, or a protein having a constant region of immunoglobulin, the capturing agent comprising a protein according to any one of items (1) to (19).

(27)

A capturing agent for an antibody, immunoglobulin G, or a protein having a constant region of immunoglobulin, the capturing agent comprising an immobilized protein according to item (25).

Advantageous Effects of Invention

The present invention can provide a mutated protein that has the largely reduced ability to bind to a constant region of immunoglobulin in an acidic region, compared with each corresponding wild-type domain (B, E, D, A, or C) of protein A consisting of an amino acid sequence set forth in any of SEQ ID NOs: 1 and 3 to 6 or the Z domain consisting of the amino acid sequence set forth in SEQ ID NO: 2, while maintaining the original antibody-binding activity in a neutral region. An antibody captured using an antibody-capturing agent comprising the mutated protein can be easily eluted without being denatured in a weakly acidic region.

Meanwhile, wild-type protein A extracellular domains are currently commercially available as affinity chromatography carriers for antibody purification or test reagents for antibody detection and widely used in each field of life science. In response to the recent development of antibody-related industries including antibody drugs, demands for these products are drastically growing. Thus, such a modified protein of the present invention can be used as a substitute for the wild-type protein in many products containing protein A extracellular domains, thereby reducing antibody deterioration attributed to acid elution. Hence, the present invention makes a great contribution to technical development in extensive technical fields that handle antibodies.

BRIEF DESCRIPTION OF DRAWINGS

FIG. 2 is a diagram showing the amino acid sequences of antibody-binding domains of protein A (a portion different from the B domain is underlined). The "E domain" corresponds to SEQ ID NO: 3. The "D domain" corresponds to SEQ ID NO: 4. The "A domain" corresponds to SEQ ID NO: 5. The "B domain" corresponds to SEQ ID NO: 1. The "C domain" corresponds to SEQ ID NO: 6. The "Z domain" corresponds to SEQ ID NO: 2.

FIG. 3 is a diagram showing the nucleotide sequence of the gene of protein A derived from *Staphylococcus aureus* subsp. *aureus* NCTC 8325 (sequences corresponding to the antibody-binding domains are underlined). This sequence corresponds to SEQ ID NO: 97.

DESCRIPTION OF EMBODIMENTS

Figure 1:
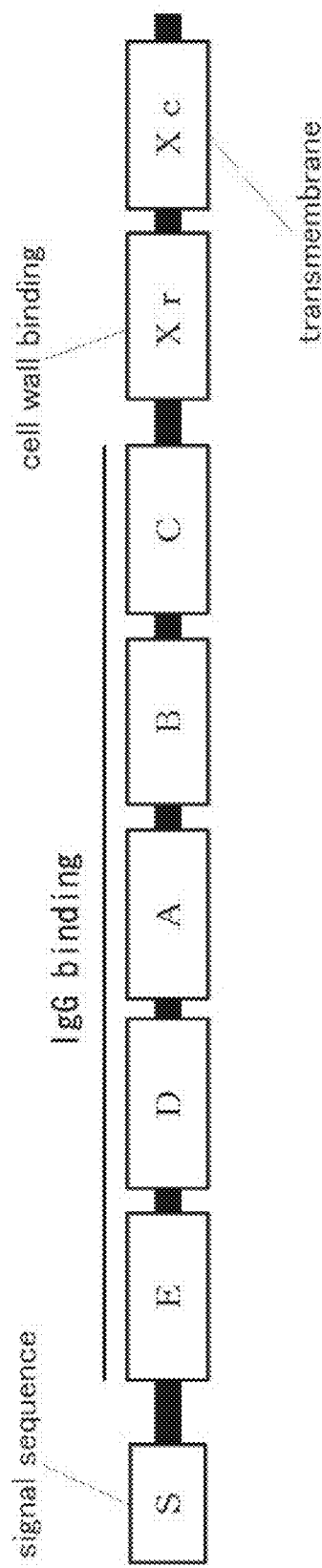
FIG. 1 is a diagram showing the structure of the gene of protein A derived from *Staphylococcus aureus* subsp. *aureus* NCTC 8325.

The modified protein of the present invention comprises an amino acid sequence artificially designed on the basis of the amino acid sequence of protein A. The modified protein of the present invention has a weak antibody-binding activity in an acidic region, compared with the wild-type extracellular domain of protein A, without impairing a selective antibody-binding activity in a neutral region, and permits elution of an antibody in a weakly acidic solution.

Aspects of the modified protein of the present invention are described in the following (i) to (vi):

(i) Mutated Protein of B Domain of Protein A

The mutated protein of the B domain of protein A of the present invention has a binding activity to a constant region of immunoglobulin and has a reduced binding activity in an acidic region to the constant region of immunoglobulin, compared with the wild-type B domain of protein A. This mutated protein comprises: a) an amino acid sequence derived from the amino acid sequence represented by SEQ ID NO: 1 by the substitution of any one or more amino acid residues of Phe5, Asn6, Gln9, Gln10, Asn11, Phe13, Tyr14, Glu15, Leu17, Glu24, Glu25, Arg27, Asn28, Ile31, Gln32, Lys35, and Asp36, preferably Phe5, Gln9, Gln10, Asn11, Glu15, Arg27, Asn28, Lys35, and Asp36, in the B domain protein of protein A by a histidine residue; b) an amino acid sequence derived from the mutated amino acid sequence a) by the insertion or addition of one or several amino acid residues; or c) an amino acid sequence derived from the amino acid sequence a) or b) by the deletion or substitution of one or several amino acid residues other than the histidine residue-substituted residue(s).

(ii) Mutated Protein of Z Domain of Protein A

The mutated protein of the Z domain of protein A of the present invention has a binding activity to a constant region of immunoglobulin and has a reduced binding activity in an acidic region to the constant region of immunoglobulin, compared with the Z domain of protein A. This mutated protein comprises:
a) an amino acid sequence derived from the amino acid sequence set forth in SEQ ID NO: 2 by the substitution of any one or more amino acid residues of Phe5, Asn6, Gln9, Gln10, Asn11, Phe13, Tyr14, Glu15, Leu17, Glu24, Glu25, Arg27, Asn28, Ile31, Gln32, Lys35, and Asp36, preferably Phe5, Gln9, Gln10, Asn11, Glu15, Arg27, Asn28, Lys35, and Asp36, in the Z domain protein of protein A by a histidine residue; b) an amino acid sequence derived from the mutated amino acid sequence according to a) by the insertion or addition of one or several amino acid residues; or c) an amino acid sequence derived from the amino acid sequence according to a) or b) by the deletion or substitution of one or several amino acid residues other than the histidine residue-substituted residue(s).

(iii) Mutated Protein of E Domain of Protein A

The mutated protein of the E domain of protein A of the present invention has a binding activity to a constant region of immunoglobulin and has a reduced binding activity in an acidic region to the constant region of immunoglobulin, compared with the wild-type E domain of protein A. This mutated protein comprises: a) an amino acid sequence derived from the amino acid sequence set forth in SEQ ID NO: 3 by the substitution of any one or more amino acid residues of Asp6, Gln9, Gln10, Asn11, Phe13, Tyr14, Glu15, Leu17, Asn18, Ala24, Asp25, Arg27, Asn28, Ile31, Gln32, Lys35, and Asp36, preferably Gln9, Gln10, Asn11, Glu15, Asn18, Arg27, Asn28, Lys35, and Asp36, in the E domain of protein A by a histidine residue; b) an amino acid sequence derived from the mutated amino acid sequence according to a) by the insertion or addition of one or several amino acid residues; or c) an amino acid sequence derived from the amino acid sequence according to a) or b) by the deletion or substitution of one or several amino acid residues other than the histidine residue-substituted residue(s).

(iv) Mutated Protein of D Domain of Protein A

The mutated protein of the D domain of protein A of the present invention has a binding activity to a constant region of immunoglobulin and has a reduced binding activity in an acidic region to the constant region of immunoglobulin, compared with the wild-type D domain of protein A. This mutated protein comprises: a) an amino acid sequence derived from the amino acid sequence represented by SEQ ID NO: 4 by the substitution of any one or more amino acid residues of Phe5, Asn6, Gln9, Gln10, Ser11, Phe13, Tyr14, Glu15, Leu17, Asn18, Glu24, Ala25, Arg27, Asn28, Ile31, Gln32, Lys35, and Asp36, preferably Phe5, Gln9, Gln10, Ser11, Glu15, Asn18, Arg27, Asn28, Lys35, and Asp36, by a histidine residue; b) an amino acid sequence derived from the mutated amino acid sequence a) by the insertion or addition of one or several amino acid residues; or c) an amino acid sequence derived from the amino acid sequence a) or b) by the deletion or substitution of one or several amino acid residues other than the histidine residue-substituted site(s).

(v) Mutated Protein of A Domain of Protein A

The mutated protein of the A domain of protein A of the present invention has a binding activity to a constant region of immunoglobulin and has a reduced binding activity in an acidic region to the constant region of immunoglobulin, compared with the wild-type A domain of protein A. This mutated protein comprises: a) an amino acid sequence derived from the amino acid sequence set forth in SEQ ID NO: 5 by the substitution of any one or more amino acid residues of Phe5, Asn6, Gln9, Gln10, Asn11, Phe13, Tyr14, Glu15, Leu17, Asn18, Glu24, Glu25, Arg27, Asn28, Ile31, Gln32, Lys35, and Asp36, preferably Phe5, Gln9, Gln10, Asn11, Glu15, Asn18, Arg27, Asn28, Lys35, and Asp36, in the A domain protein of protein A by a histidine residue; b) an amino acid sequence derived from the mutated amino acid sequence according to a) by the insertion or addition of one or several amino acid residues; or c) an amino acid sequence derived from the amino acid sequence according to a) or b) by the deletion or substitution of one or several amino acid residues other than the histidine residue-substituted residue(s).

(vi) Mutated Protein of C Domain of Protein A

The mutated protein of the C domain of protein A of the present invention has a binding activity to a constant region of immunoglobulin and has a reduced binding activity in an acidic region to the constant region of immunoglobulin, compared with the wild-type C domain of protein A. This mutated protein comprises: a) an amino acid sequence derived from the amino acid sequence set forth in SEQ ID NO: 6 by the substitution of any one or more amino acid residues of Phe5, Asn6, Gln9, Gln10, Asn11, Phe13, Tyr14, Glu15, Leu17, Glu24, Glu25, Arg27, Asn28, Ile31, Gln32, Lys35, and Asp36, preferably Phe5, Gln9, Gln10, Asn11, Glu15, Arg27, Asn28, Lys35, and Asp36, in the C domain of protein A by a histidine residue; b) an amino acid sequence derived from the mutated amino acid sequence according to a) by the insertion or addition of one or several amino acid residues; or c) an amino acid sequence derived from the amino acid sequence according to a) or b) by the deletion or substitution of one or several amino acid residues other than the histidine residue-substituted residue(s).

1. Design of Amino Acid Sequence of Modified Protein

The mutated proteins (i) to (vi) are designed on the basis of sites to be mutated selected as shown below and amino acid residues that substitute the sites, and obtained by a genetic engineering approach or the like.

The sites to be mutated for designing the amino acid sequence of the modified protein of the present invention were selected using three-dimensional structure atomic coordinate data on a complex of the B domain of protein A bound with the Fc region of immunoglobulin G (Reference 4), and frequency analysis data of a screening experiment from a mutated protein A library obtained by a phage display method.

The ability of each extracellular domain of protein A to bind to antibodies in an acidic region can be reduced by the substitution of binding-surface amino acid residues of the protein A extracellular domain directly involved in binding to the Fc region and their neighboring amino acid residues from wild-type ones to non-wild-type ones.

Thus, in the complex of the B domain of protein A bound with the Fc region of immunoglobulin G, amino acid residues of the B domain of protein A located within the range of a predetermined distance from the Fc region are first identified and used as candidates for sites to be mutated. Of these candidates, only amino acid residues exposed at the molecular surface of the B domain of protein A were subsequently determined as sites to be mutated in order to minimize the structural destabilization of the protein A extracellular domain attributed to the amino acid substitution.

Specifically, as shown later in Examples, the range of the distance was set to within 10 angstroms, and the ratio of exposed surface area was set to 20% or more. As a result, 18 residues in the wild-type amino acid sequence (SEQ ID NO:

1) of the B domain of protein A were selected as sites to be mutated: Phe5, Asn6, Gln9, Gln10, Asn11, Phe13, Tyr14, Glu15, Leu17, His18, Glu24, Glu25, Arg27, Asn28, Ile31, Gln32, Lys35, and Asp36. Of these 18 sites to be mutated, more preferred sites to be mutated that could be expected to produce high effects were subsequently selected using sequence analysis data of a screening experiment from a mutated protein A library obtained by a phage display method.

Specifically, as shown later in Examples, sites that gave higher frequency of histidine residues than the frequency of wild-type amino acid residues in the sequence analysis data were determined to select 10 residues Phe5, Gln9, Gln10, Asn11, Glu15, His18, Arg27, Asn28, Lys35, and Asp36 in the wild-type amino acid sequence (SEQ ID NO: 1) of the B domain of protein A as preferred sites to be mutated.

As described above, the extracellular domains of protein A have high sequence homology to each other (FIG. 2). In addition, the D, E, and Z domains whose three-dimensional structures have been revealed experimentally rarely differ in structure from the B domain alone (References 5 to 8). Thus, findings about the three-dimensional structure of the B domain-Fc complex can also be applied to E, D, A, C, and Z domain-Fc complexes.

Specifically, although the three-dimensional structures of the E domain-Fc complex, the D domain-Fc complex, the A domain-Fc complex, the C domain-Fc complex, and the Z domain-Fc complex have not yet been revealed, the deduction that the E, D, A, C, and Z domain-Fc complexes form a structure homologous to that of the B domain-Fc complex can be drawn naturally on the basis of the sequence homology of each extracellular domain and similarity in the three-dimensional structures of the B, D, E, and Z domains alone.

Thus, the selected 18 sites to be mutated are strongly expected to be positioned, also in the E, D, A, C, and Z domain-Fc complexes, in spatial arrangement equivalent to that in the B domain-Fc complex. These 18 sites to be mutated (residues 5, 6, 9, 10, 11, 13, 14, 15, 17, 18, 24, 25, 27, 28, 31, 32, 35, and 36) derived from the three-dimensional structure of the B domain-Fc complex can be selected as sites to be mutated in the B domain as well as the D, A, C, and Z domains.

Also, the 10 preferred sites to be mutated (residues 5, 9, 10, 11, 15, 18, 27, 28, 35 and 36) selected using the frequency analysis data of a screening experiment can be selected as preferred sites to be mutated in the B domain as well as the D, A, C, and Z domains.

Specifically, 18 residues Phe5, Asn6, Gln9, Gln10, Asn11, Phe13, Tyr14, Glu15, Leu17, His18, Glu24, Glu25, Arg27, Asn28, Ile31, Gln32, Lys35, and Asp36, preferably 10 residues Phe5, Gln9, Gln10, Asn11, Glu15, His18, Arg27, Asn28, Lys35, and Asp36, in the amino acid sequence (SEQ ID NO: 2) of the Z domain of protein A, 18 residues His5, Asp6, Gln9, Gln10, Asn11, Phe13, Tyr14, Gln15, Leu17, Asn18, Ala24, Asp25, Arg27, Asn28, Ile31, Gln32, Lys35, and Asp36, preferably 10 residues His5, Gln9, Gln10, Asn11, Gln15, Asn18, Arg27, Asn28, Lys35, and Asp36, in the wild-type amino acid sequence (SEQ ID NO: 3) of the E domain of protein A, 18 residues Phe5, Asn6, Gln9, Gln10, Ser11, Phe13, Tyr14, Glu15, Leu17, Asn18, Glu24, Ala25, Arg27, Asn28, Ile31, Gln32, Lys35, and Asp36, preferably 10 residues Phe5, Gln9, Gln10, Ser11, Glu15, Asn18, Arg27, Asn28, Lys35, and Asp36, in the wild-type amino acid sequence (SEQ ID NO: 4) of the D domain of protein A, 18 residues Phe5, Asn6, Gln9, Gln10, Asn11, Phe13, Tyr14, Glu15, Leu17, Asn18, Glu24, Glu25, Arg27, Asn28, Ile31, Gln32, Lys35, and Asp36, preferably 10 residues Phe5, Gln9, Gln10, Asn11, Glu15, Asn18, Arg27, Asn28, Lys35, and Asp36, in the wild-type amino acid sequence (SEQ ID NO: 5) of the A domain of protein A, and 18 residues Phe5, Asn6, Gln9, Gln10, Asn11, Phe13, Tyr14, Glu15, Leu17, His18, Glu24, Glu25, Arg27, Asn28, Ile31, Gln32, Lys35, and Asp36, preferably 10 residues Phe5, Gln9, Gln10, Asn11, Glu15, His18, Arg27, Asn28, Lys35, and Asp36, in the wild-type amino acid sequence (SEQ ID NO: 6) of the C domain of protein A were selected as sites to be mutated.

On the other hand, the best amino acid residue that substitutes each of the original amino acid residues at the sites to be mutated is histidine. This is because histidine largely varies in chemical state due to the dissociation of side chain protons between a neutral region and an acidic region and therefore, can largely change the ability of each domain of protein A to bind to antibodies between the neutral region and the acidic region.

Thus, as shown later in Examples, the modified protein of the present invention encompasses the following: the mutant of the B domain of the protein A according to the aspect (i), comprising any one or more of Phe5His, Asn6His, Gln9His, Gln10His, Asn11His, Phe13His, Tyr14His, Glu15His, Leu17His, Glu24His, Glu25His, Arg27His, Asn28His, Ile31His, Gln32His, Lys35His, Asp36His, preferably Phe5His, Gln9His, Gln10His, Asn11His, Glu15His, Arg27His, Asn28His, Lys35His, and Asp36His; the mutant of the Z domain of the protein A according to the aspect (ii), comprising any one or more of Phe5His, Asn6His, Gln9His, Gln10His, Asn11His, Phe13His, Tyr14His, Glu15His, Leu17His, Glu24His, Glu25His, Arg27His, Asn28His, Ile31His, Gln32His, Lys35His, Asp36His, preferably Phe5His, Gln9His, Gln10His, Asn11His, Glu15His, Arg27His, Asn28His, Lys35His, and Asp36His; the mutant of the E domain of the protein A according to the aspect (iii), comprising any one or more of Asp6His, Gln9His, Gln10His, Asn11His, Phe13His, Tyr14His, Gln15His, Leu17His, Asn18His, Ala24His, Asp25His, Arg27His, Asn28His, Ile31His, Gln32His, Lys35His, Asp36His, preferably Asp6His, Gln10His, Asn11His, Gln15His, Asn18His, Arg27His, Asn28His, Lys35His, and Asp36His; the mutant of the D domain of the protein A according to the aspect (iv), comprising any one or more of Phe5His, Asn6His, Gln9His, Gln10His, Ser11His, Phe13His, Tyr14His, Glu15His, Leu17His, Asn18His, Glu24His, Ala25His, Arg27His, Asn28His, Ile31His, Gln32His, Lys35His, Asp36His, preferably Phe5His, Gln9His, Gln10His, Ser11His, Glu15His, Asn18His, Arg27His, Asn28His, Lys35His, and Asp36His; the mutant of the A domain of the protein A according to the aspect (v), comprising any one or more of Phe5His, Asn6His, Gln9His, Gln10His, Asn11His, Phe13His, Tyr14His, Glu15His, Leu17His, Asn18His, Glu24His, Glu25His, Arg27His, Asn28His, Ile31His, Gln32His, Lys35His, Asp36His, preferably Phe5His, Gln9His, Gln10His, Asn11His, Glu15His, Asn18His, Arg27His, Asn28His, Lys35His, and Asp36His; and the mutant of the C domain of the protein A according to the aspect (vi), comprising any one or more of Phe5His, Asn6His, Gln9His, Gln10His, Asn11His, Phe13His, Tyr14His, Glu15His, Leu17His, Glu24His, Glu25His, Arg27His, Asn28His, Ile31His, Gln32His, Lys35His, Asp36His, preferably Phe5His, Gln9His, Gln10His, Asn11His, Glu15His, Arg27His, Asn28His, Lys35His, and Asp36H is. In this context, the wild-type amino acid at residue 5 in the E domain and residue 18 in the B, C, and Z domains is histidine. The substitution of these residues by histidine causes no change between before and after the substitution. Thus, His5His in the E domain and His18His in the B, C, and Z domains are excluded therefrom.

As is evident from above, the sites to be mutated selected in the design of the modified protein of the present invention are not limited to one residue. Appropriate residues can be selected from among a plurality of sites to be mutated and combined to prepare a point mutant or a multiple mutant as the modified protein. This selection may be performed at random or in consideration of other pieces of information known in the art, such as structure activity correlation. Alternatively, these mutations may be combined with a mutation already known to change the properties of the protein A extracellular domain to preferred ones.

Specifically, examples of the modified protein of the present invention included in the aspect (i) include: an Asn6His/Asn11His/Glu15Asp/Glu24Gln/Glu25His quintuple mutant (SEQ ID NO: 7) of the B domain of protein A obtained by selecting residues 6, 11, 15, 24, and 25 as sites to be mutated and introducing histidine residues to the residues 6, 11, and 25; an Asn6His/Glu24His/Glu25Gln/Gln32His/Asp36His quintuple mutant (SEQ ID NO: 8) of the B domain of protein A obtained by selecting residues 6, 24, 25, 32, and 36 as the sites and introducing histidine residues to the residues 6, 24, 32, and 36; an Asn6His point mutant (SEQ ID NO: 10) of the B domain of protein A obtained by introducing a histidine residue to residue 6; a Glu24His point mutant (SEQ ID NO: 11) of the B domain of protein A obtained by introducing a histidine residue to residue 24; a Gln32His point mutant (SEQ ID NO: 12) of the B domain of protein A obtained by introducing a histidine residue to residue 32; an Asp36His point mutant (SEQ ID NO: 13) of the B domain of protein A obtained by introducing a histidine residue to residue 36; a Phe5His/Gln9His/Gln10His/Asn11His/Phe13Leu/Glu15His/Glu25 Asp/Arg27His/Asn28His/Lys35His/Asp36His undecuple mutant (SEQ ID NO: 14) of the B domain of protein A obtained by selecting residues 5, 9, 10, 11, 13, 15, 25, 27, 28, 35, and 36 as the sites and introducing histidine residues to the residues 5, 9, 10, 11, 15, 27, 28, 35, and 36; a Phe5His/Asn6His/Gln9His/Gln10His/Asn11His/Phe13Leu/Glu15His/Glu25Asp/Arg27His/Asn28His/Lys35His/Asp36His duodecuple mutant (SEQ ID NO: 15) of the B domain of protein A obtained by selecting residues 5, 6, 9, 10, 11, 13, 15, 25, 27, 28, 35, and 36 as the sites and introducing histidine residues to the residues 5, 6, 9, 10, 11, 15, 27, 28, 35, and 36; and a Phe5His/Gln9His/Gln10His/Asn11His/Phe13Leu/Glu15His/Glu24Gln/Glu25Asp/Arg27His/Asn28His/Ile31Leu/Lys35His/Asp36His tredecuple mutant (SEQ ID NO: 16) of the B domain of protein A obtained by selecting residues 5, 9, 10, 11, 13, 15, 24, 25, 27, 28, 31, 35, and 36 as the sites and introducing histidine residues to the residues 5, 9, 10, 11, 15, 27, 28, 35, and 36.

Also, multiple mutants of the B domain of protein A shown in SEQ ID NOs: 17 to 27 and 65 to 71 and point mutants of the B domain of protein A shown in SEQ ID NOs: 61 to 64 are examples of the modified protein of the present invention included in the aspect (i). Examples of the modified protein of the present invention included in the aspect (ii) include: an Asn6His/Glu24His/Glu25Gln/Gln32His/Asp36His quintuple mutant (SEQ ID NO: 9) of the Z domain of protein A obtained by selecting residues 6, 24, 25, 32, and 36 as sites to be mutated and introducing histidine residues to the residues 6, 24, 32, and 36; and an Asp36His point mutant (SEQ ID NO: 72) of the Z domain of protein A obtained by introducing a histidine residue to residue 36. Examples of the modified protein of the present invention included in the aspect (vi) include: an Asp36His point mutant (SEQ ID NO: 74) of the C domain of protein A obtained by introducing a histidine residue to residue 36 as a site to be mutated; a Gln9His point mutant (SEQ ID NO: 75) of the C domain of protein A obtained by introducing a histidine residue to residue 9; and a Gln9His/Asp36His double mutant (SEQ ID NO: 76) of the C domain of protein A obtained by introducing histidine residues to residues 9 and 36. As shown later in Examples, plural types of amino acid sequences as described above can be designed for the modified protein of the present invention.

The modified protein of the present invention, including the point mutants and the multiple mutants shown in SEQ ID NOs: 7 to 27, 61 to 72, and 74 to 76, may further have an insertion or addition mutation at one or several amino acid residues or a deletion or substitution mutation at one or several amino acid residues except for the histidine-substituted residue(s), as long as the resulting modified protein has a binding activity to an antibody, immunoglobulin G, or a protein having the Fc region of immunoglobulin G and has a reduced binding activity in an acidic region to the constant region of immunoglobulin, compared with each corresponding wild-type extracellular domain protein of protein A.

For example, the modified protein of the present invention may be synthesized in the form of a tagged protein such as a His-tagged protein or a fusion protein with an additional protein. In such a case, one to several amino acid residues derived from the tag or the additional protein may remain at the N-terminus or C-terminus of the modified protein even if the protein thus synthesized is digested, between the tag and the modified protein or between the additional protein and the modified protein, with a sequence-specific proteolytic enzyme. Alternatively, start codon-derived methionine or the like may be added to the N-terminal side of the modified protein of the present invention produced using, for example, *E. coli*. As shown later in Examples, however, the addition of these amino acid residues does not largely change the ability to bind to antibodies. Also as shown later in Examples, the addition of these amino acid residues does not cancel effects brought about by the designed mutation. Thus, the modified protein of the present invention also includes these mutants, as a matter of course.

In order to prepare a modified protein without the addition of such amino acid residues, N-terminal amino acid residues are selectively cleaved from the modified protein produced using, for example, *E. coli*, using an enzyme such as methionyl aminopeptidase (Reference 9). The modified protein of interest can be obtained from the resulting reaction mixture through separation and purification by chromatography or the like.

Alternatively, the amino acid sequence of the modified protein of the present invention may be a tandem-type amino acid sequence in which the amino acid sequence and an arbitrary linker sequence are alternately arranged as a plurality of repeats. Such a sequence may be, for example, [amino acid sequence (a)]—linker sequence A—[amino acid sequence (a)]—linker sequence B—[amino acid sequence (a)] or [amino acid sequence (a)]—linker sequence C—[amino acid sequence (b)]-linker sequence D—[amino acid sequence (c)].

As is evident from the fact that: wild-type protein A has a repeat structure of a plurality of antibody-binding domains via linker sequences (FIGS. 1 and 3); and each domain isolated by the cleavage of wild-type protein A maintains the antibody-binding activity in itself (Reference 3), the configuration of this tandem-type amino acid sequence is effective because wild-type protein A assumes a repeat structure of a plurality of antibody-binding domains capable of functioning even alone to increase the local concentration, thereby enhancing the effects of the ability to bind to antibodies.

Alternatively, the modified protein of the present invention may be a fusion protein comprising a fused amino acid sequence in which the amino acid sequence is linked to the amino acid sequence of an arbitrary additional protein. Such a sequence may be, for example, [amino acid sequence (a)]—linker sequence E—additional protein A, or additional protein B—linker sequence F—[amino acid sequence (a)]—linker sequence G—additional protein C—linker sequence H—[amino acid sequence (c)]. The configuration of this fused amino acid sequence is effective on the grounds that: wild-type protein A has a multidomain structure composed of antibody-binding domains linked to other domains (FIGS. 1 and 3); and each domain isolated by the cleavage of wild-type protein A maintains the antibody-binding activity in itself (Reference 3), i.e., the linking of the antibody-binding domains to a protein responsible for other functions allows the resulting protein to exert a plurality of functions including the antibody-binding activity.

The amino acid sequence of a spacer for immobilization reaction may be added to the C-terminus, N-terminus, or central portion of the modified protein of the present invention. Such a sequence may be, for example, [amino acid sequence (a)]—spacer sequence A, spacer sequence B—[amino acid sequence (b)], or [amino acid sequence (c)]—spacer sequence C—[amino acid sequence (d)]. The spacer is used for the purpose of, for example, promoting the efficiency of immobilization reaction or reducing steric hindrance with an immobilization carrier. The amino acid sequence or chain length of the spacer can be appropriately selected according to the type of the immobilization reaction used, etc. For example, GlyArgAlaCysGly (Reference 10) or GlyGlyGlyGlyCysAlaAspAspAspAspAspAsp (Reference 11) can be used. However, the amino acid sequence or chain length of the spacer used in the modified protein of the present invention is not particularly limited.

2. Production of Modified Protein (1) Production of Modified Protein by Genetic Engineering Approach a. Gene Encoding Modified Protein In the present invention, each modified protein thus designed can be produced using a genetic engineering method.

The gene used in such a method encodes the amino acid sequence of any of the proteins (i) to (vi). More specifically, the gene comprises a nucleic acid encoding a) an amino acid sequence represented by any of SEQ ID NOs: 7 to 27, 61 to 72, and 74 to 76, b) a protein which comprises an amino acid sequence derived from the amino acid sequence represented by any of SEQ ID NOs: 7 to 27, 61 to 72, and 74 to 76 by the insertion or addition of one or several amino acid residues, has a binding activity to an antibody, immunoglobulin G, or a protein having a constant region of immunoglobulin, and has a reduced binding activity in an acidic region compared with a neutral region, or c) a protein which comprises an amino acid sequence derived from the amino acid sequence represented by any of SEQ ID NOs: 7 to 27, 61 to 72, and 74 to 76 by the deletion or substitution of one or several amino acid residues other than histidine residues, has a binding activity to an antibody, immunoglobulin G, or a protein having a constant region of immunoglobulin, and has a reduced binding activity in an acidic region compared with a neutral region. More specifically, the gene is, for example, a nucleic acid comprising a nucleotide sequence represented by any of SEQ ID NOs: 28 to 30, 43 to 60, and 77 to 91.

Examples of the gene used in the present invention also include a nucleic acid which hybridizes under stringent conditions to a nucleic acid comprising a sequence complementary to the nucleotide sequence of any of the nucleic acids described above and encodes the mutated protein having a binding activity to an antibody, immunoglobulin G, or a protein having a constant region of immunoglobulin and having a reduced binding activity in an acidic region to the constant region of immunoglobulin, compared with each corresponding wild-type extracellular domain protein of protein A.

In this context, the stringent conditions refer to conditions under which specific hybrids are formed and nonspecific hybrids are not formed. The stringent conditions refer to, for example, conditions under which nucleic acids having high homology (60% or higher, preferably 80% or higher, more preferably 90% or higher, most preferably 95% or higher homology) hybridize to each other. More specifically, the conditions involve a sodium concentration of 150 to 900 mM, preferably 600 to 900 mM, and a temperature of 60 to 68° C., preferably 65° C. For example, successful hybridization under conditions involving hybridization at 65° C. and washing at 65° C. for 10 minutes in 0.1×SSC containing 0.1% SDS can be confirmed by a conventional approach, for example, Southern blot or dot blot hybridization, and thereby regarded as hybridization under stringent conditions.

Alternatively, the gene used in the present invention may be a gene in which a plurality of any of the nucleic acids described above are linked to a plurality of nucleic acids each encoding the arbitrary linker sequence in an alternate manner, or may be designed so that the nucleic acid is linked to a nucleic acid encoding the amino acid sequence of an arbitrary protein to encode a fused amino acid sequence.

b. Gene, Recombinant Vector, and Transformant

The gene of the present invention can be synthesized by chemical synthesis, PCR, cassette mutagenesis, site-directed mutagenesis, or the like. For example, a plurality of oligonucleotides up to approximately 100 bases having approximately 20-bp complementary regions at their ends are chemically synthesized. An overlap extension method (Reference 12) can be performed using combinations of these synthesized oligonucleotides to fully synthesize the gene of interest.

The recombinant vector of the present invention can be obtained by ligating (inserting) the gene comprising the nucleotide sequence to an appropriate vector. The vector used in the present invention is not particularly limited as long as the vector is replicable in a host or permits integration of the gene of interest into the host genome. Examples thereof include bacteriophages, plasmids, cosmids, and phagemids.

Examples of the plasmid DNA include ray fungus-derived plasmids (e.g., pK4, pRK401, and pRF31), E. coli-derived plasmids (e.g., pBR322, pBR325, pUC118, pUC119, and pUC18), Bacillus subtilis-derived plasmids (e.g., pUB110 and pTP5), and yeast-derived plasmids (e.g., YEp13, YEp24, and YCp50). Examples of the phage DNA include λ phages (λgt10, λgt11, λZAP, etc.). Alternatively, a vector derived from an animal virus such as retrovirus or vaccinia virus or an insect virus such as baculovirus may be used.

The gene can be inserted to the vector by the adoption of a method which involves, for example, first cleaving purified DNA with appropriate restriction enzymes and ligating the resulting fragment with a vector by insertion into an appropriate restriction site or a multicloning site of the vector DNA. The gene must be incorporated in the vector such that the modified protein of the present invention is expressed.

In this respect, the vector of the present invention can have a sequence linked to a promoter, the nucleotide sequence of the gene, and if desired, a cis element such as an enhancer, a splicing signal, a poly-A addition signal, a selection marker, a ribosomal binding sequence (SD sequence), a start codon, a stop codon, etc. Also, the vector sequence may be linked to a tag sequence for facilitating the purification of produced proteins. A nucleotide sequence encoding a tag known in the art such as a His, GST, MBP, or BioEase tag can be used as the tag sequence.

Whether or not the gene is successfully inserted in the vector can be confirmed by use of a genetic engineering technique known in the art. In the case of, for example, a plasmid vector, the vector is subcloned using competent cells. After DNA extraction, its nucleotide sequence can be determined using a DNA sequencer to confirm successful insertion. A similar approach can also be used for other vectors that may be subcloned using bacterial or other hosts. Vector screening using a selection marker such as a drug resistance gene is also effective.

The transformant can be obtained by transferring the recombinant vector of the present invention into host cells such that the host cells are capable of expressing the modified protein of the present invention. The host used in transformation is not particularly limited as long as the host can express proteins or polypeptides. Examples thereof include bacteria (*E. coli*, *Bacillus subtilis*, etc.), yeasts, plant cells, animal cells (COS cells, CHO cells, etc.), and insect cells.

For a bacterial host, preferably, the recombinant vector is autonomously replicable in the bacterium and also constituted by a promoter, a ribosomal binding sequence, a start codon, the nucleic acid encoding the modified protein of the present invention, and a transcription termination sequence. Examples of the *E. coli* include *Escherichia coli* BL21. Examples of the *Bacillus subtilis* include *Bacillus subtilis* strains. The method for transferring the recombinant vector to the bacterium is not particularly limited as long as the method can transfer DNA to bacteria. Examples thereof include a heat shock method, a method using calcium ions, and electroporation.

In the case of using a yeast as the host, for example, *Saccharomyces cerevisiae* or *Schizosaccharomyces pombe* is used. The method for transferring the recombinant vector to the yeast is not particularly limited as long as the method can transfer DNA to yeasts. Examples thereof include electroporation, spheroplast, and lithium acetate methods.

In the case of using animal cells as the host, for example, monkey cells COS-7, Vero, Chinese hamster ovary cells (CHO cells), mouse L cells, rat GH3, or human FL cells are used. Examples of the method for transferring the recombinant vector to the animal cells include electroporation, calcium phosphate, and lipofection methods.

In the case of using insect cells as the host, for example, Sf9 cells are used. Examples of the method for transferring the recombinant vector to the insect cells include calcium phosphate, lipofection, and electroporation methods.

Whether or not the gene is successfully introduced in the host can be confirmed by PCR, Southern hybridization, Northern hybridization, or the like. For example, DNA is prepared from the transformant and subjected to PCR using designed DNA-specific primers. Subsequently, the PCR amplification product is subjected to, for example, agarose gel electrophoresis, polyacrylamide gel electrophoresis, or capillary electrophoresis. The gel is stained with ethidium bromide, a Sybr Green solution, or the like. The amplification product can be detected as a single band to confirm successful transformation. Alternatively, PCR may be performed using primers labeled in advance with fluorescent dyes or the like, and the amplification product can be detected.

c. Obtainment of Modified Protein by Transformant Culture

When produced as a recombinant protein, the modified protein of the present invention can be obtained by culturing the transformant and collecting the protein of interest from the cultures. The cultures mean any of a culture supernatant, cultured cells or a cultured bacterial body, and homogenates of the cells or the bacterial body. The transformant of the present invention is cultured according to a usual method for use in host culture.

Any of natural and synthetic media may be used for culturing the transformant obtained from a microbial (e.g., *E. coli* or yeast) host as long as the medium contains a carbon source, a nitrogen source, inorganic salts, and the like utilizable by the microbe and permits efficient culture of the transformant.

Examples of the carbon source include: hydrocarbons such as glucose, fructose, sucrose, and starch; organic acids such as acetic acid and propionic acid; and alcohols such as ethanol and propanol. Examples of the nitrogen source include: ammonia; ammonium salts of inorganic or organic acids such as ammonium chloride, ammonium sulfate, ammonium acetate, and ammonium phosphate; other nitrogen-containing compounds; and peptone, meat extracts, and corn steep liquors. Examples of inorganic matter include monopotassium phosphate, dipotassium phosphate, magnesium phosphate, magnesium sulfate, sodium chloride, ferrous sulfate, manganese sulfate, copper sulfate, and calcium carbonate. The culture is usually performed at 20 to 37° C. for 12 hours to 3 days under aerobic conditions such as shake culture or aeration stirring culture.

The bacterial body or cells thus cultured may produce the modified protein of the present invention therewithin. In such a case, the bacterial body or cells are homogenized by sonication, repetitive freezing-thawing operation, homogenizer treatment, or the like to collect the protein. Alternatively, the protein may be produced outside the bacterial body or cells. In such a case, the culture solution is directly used, or the bacterial body or cells are removed by centrifugation or the like. Then, the modified protein of the present invention can be isolated and purified from the cultures using, alone or in appropriate combination, general biochemical methods for use in protein isolation and purification, for example, ammonium sulfate precipitation, gel chromatography, ion-exchange chromatography, and affinity chromatography.

A so-called cell-free synthesis system, which involves only a mixture of factors involved in protein biosynthesis reaction (enzyme, nucleic acid, ATP, amino acid, etc.), can be used to synthesize the modified protein of the present invention in vitro from the vector without the use of live cells (Reference 13). Then, the modified protein of the present invention can be isolated and purified from the mixed solution after reaction using the same purification method as above.

In order to confirm that the modified protein of the present invention thus isolated and purified is a protein comprising the amino acid sequence as intended, a sample containing the protein is analyzed. This analysis can be conducted using a method such as SDS-PAGE, Western blotting, mass spectrometry, amino acid analysis, or an amino acid sequencer (Reference 14).

(2) Production of Modified Protein by Other Approaches

The modified protein of the present invention can also be produced by an organic chemical approach, for example, a solid-phase peptide synthesis method. The method for producing proteins by use of such an approach is well known in the art and will be briefly described below.

Chemical protein production by the solid-phase peptide synthesis method preferably employs an automatic synthesizer. A protected polypeptide having the amino acid sequence of the modified protein of the present invention is synthesized on a resin through the repetitive polycondensation reaction of activated amino acid derivatives. Subsequently, this protected polypeptide is cleaved from the resin while the protective groups on the side chains are cleaved at the same time. This cleavage reaction is known to have an appropriate cocktail according to the types of the resin and the protective groups and the composition of amino acids (Reference 15). Then, the partially purified protein is transferred from the organic solvent layer to an aqueous layer, and the mutated protein of interest is purified. A method such as reverse-phase chromatography can be used in the purification (Reference 16).

3. Immobilization of Modified Protein

The modified protein of the present invention can be used as an antibody-capturing agent by use of its ability to bind to antibodies. The antibody-capturing agent can be used in antibody purification or removal, antibody-based research, diagnosis, treatment, examination, etc.

The antibody-capturing agent of the present invention can be in any form comprising the modified protein of the present invention. Preferably, a form comprising the modified protein of the present invention immobilized on a water-insoluble solid-phase support is appropriate. Examples of the water-insoluble carrier used include: inorganic carriers such as glass beads and silica gel; synthetic polymers such as cross-linked polyvinyl alcohol, cross-linked polyacrylate, cross-linked polyacrylamide, and cross-linked polystyrene; organic carriers made of polysaccharides such as crystalline cellulose, cross-linked cellulose, cross-linked agarose, and cross-linked dextran; and composite carriers such as organic-organic and organic-inorganic carriers obtained by combinations thereof. Among them, a hydrophilic carrier is preferred because of its relatively low nonspecific adsorption and favorable selectivity for an antibody, immunoglobulin G, or a protein having a constant region of immunoglobulin.

In this context, the hydrophilic carrier refers to a carrier that has a contact angle of 60 degrees or smaller with water when a compound constituting the carrier is shaped into a flat plate. Typical examples of such a carrier include carriers made of polysaccharides such as cellulose, chitosan, and dextran, polyvinyl alcohol, ethylene-vinyl acetate copolymer saponification products, polyacrylamide, polyacrylic acid, polymethacrylic acid, methyl polymethacrylate, polyacrylic acid-grafted polyethylene, polyacrylamide-grafted polyethylene, and glass.

Examples of commercially available products can include porous cellulose gels GCL2000 and GC700, Sephacryl S-1000 having allyl dextran and methylenebisacrylamide cross-linked via a covalent bond, an acrylate-based carrier Toyopearl, an agarose-based cross-linked carrier Sepharose CL4B, and epoxy group-activated polymethacrylamide Eupergit C250L. However, the carrier of the present invention is not limited to these carriers or activated carriers. These carriers may be used alone or as an arbitrary mixture of two or more thereof. Desirably, the water-insoluble carrier used in the present invention has a large surface area in view of the use purpose of the antibody-capturing agent of the present invention and a method for using the same. Preferably, the water-insoluble carrier has a large number of pores having an appropriate size, i.e., is porous.

The carrier can be in any form such as beads, fibers, or membranes (also including hollow fiber membranes), and an arbitrary form can be selected. Beads are particularly preferably used because a carrier having a particular molecular weight exclusion limit can be easily prepared. Beads having an average particle size of 10 to 2500 μm are easy to use. Particularly, the average particle size is preferably in the range of 25 μm to 800 μm because ligand immobilization reaction easily occurs.

The carrier further having, on its surface, functional groups that may be used in ligand immobilization reaction is convenient for ligand immobilization. Typical examples of these functional groups include hydroxy, amino, aldehyde, carboxyl, thiol, silanol, amide, epoxy, succinylimide, and acid anhydride groups.

More preferably, the modified protein is immobilized onto the carrier via a hydrophilic spacer in order to reduce the steric hindrance of the modified protein, thereby improving capturing efficiency and further suppressing nonspecific binding. For example, a polyalkylene oxide derivative substituted by a carboxyl, amino, aldehyde, or epoxy group at both ends is preferably used as the hydrophilic spacer.

Examples of the method for immobilizing the modified protein and the organic compound serving as a spacer onto the carrier include, but not particularly limited to, methods generally adopted for immobilizing proteins or peptides onto carriers.

Examples thereof include: a method which involves activating the carrier through its reaction with cyanogen bromide, epichlorohydrin, diglycidyl ether, tosyl chloride, tresyl chloride, hydrazine, or the like (changing the original functional groups of the carrier to functional groups easily reactive with the compound to be immobilized as a ligand) and reacting the activated carrier with the compound to be immobilized as a ligand to immobilize the compound thereon; and an immobilization method which involves adding a condensation reagent such as carbodiimide or a reagent having a plurality of functional groups in the molecule, such as glutaraldehyde, to a system containing the carrier and the compound to be immobilized as a ligand to perform condensation and cross-linking. An immobilization method that is less likely to cause the dissociation of proteins from the carrier during the sterilization or utilization of the capturing agent is more preferably applied to the present invention.

4. Performance Confirmation Test of Modified Protein and Antibody-Capturing Agent The modified protein and the antibody-capturing agent thus produced can be subjected to performance confirmation tests shown below to select favorable ones. As shown later in Examples, the modified proteins and the antibody-capturing agents of the present invention all had favorable performance.

(1) Test on Ability to Bind to Antibody

The ability of the modified protein of the present invention to bind to antibodies can be confirmed and evaluated by use of Western blotting, immunoprecipitation, pull-down assay, enzyme-linked immunosorbent assay (ELISA), a surface plasmon resonance (SPR) method, or the like. Among them, the SPR method achieves real-time observation of the interaction between living bodies over time without labels and can therefore quantitatively evaluate the binding reaction of the modified protein from a kinetic standpoint.

Also, the ability of the modified protein immobilized on the water-insoluble solid-phase support to bind to antibodies can be confirmed and evaluated by the SPR method or liquid chromatography. Among them, the liquid chromatography can accurately evaluate the pH dependence of the ability to bind to antibodies.

(2) Test on Thermal Stability of Modified Protein

The thermal stability of the modified protein of the present invention can be evaluated by use of circular dichroism (CD) spectroscopy, fluorescence spectroscopy, infrared spectroscopy, differential scanning calorimetry, residual activity after heating, or the like. Among them, the CD spectroscopy is a spectroscopic analytical method that sensitively reflects change in the secondary structure of a protein and can therefore evaluate structural stability in a thermodynamic and quantitative manner by observing temperature-dependent change in the three-dimensional structure of the modified protein.

Reference 1: Forsgren A and Sjoquist J (1966) "Protein A" from *S. Aureus. J. Immunol.* 97, 822-827.

Reference 2: Boyle M. D. P., Ed. (1990) Bacterial Immunoglobulin Binding Proteins. Academic Press, Inc., San Diego, Calif., USA.

Reference 3: Tashiro M, Montelione G T. (1995) Structures of bacterial immunoglobulin-binding domains and their complexes with immunoglobulins. Curr Opin Struct Biol. 5, 471-481.

Reference 4: Deisenhofer J. (1981) Crystallographic refinement and atomic models of a human Fc fragment and its complex with fragment B of protein A from *Staphylococcus aureus* at 2.9- and 2.8-A resolution. Biochemistry. 20 (9), 2361-2370.

Reference 5: Gouda H, Torigoe H, Saito A, Sato M, Arata Y, Shimada I. (1992) Three-dimensional solution structure of the B domain of staphylococcal protein A: comparisons of the solution and crystal structures. Biochemistry. 31 (40), 9665-9672.

Reference 6: Tashiro M.; Tejero R.; Zimmerman D. E.; Celda B.; Nilsson B.; Montelione G. T. (1997) High-resolution solution NMR structure of the Z domain of staphylococcal protein A. Journal of Molecular Biology, 272 (4), 573-590.

Reference 7: Starovasnik, M. A., Skelton, N. J., O'Connell, M. P., Kelley, R. F., Reilly, D., Fairbrother, W. J. (1996) Solution structure of the E-domain of staphylococcal protein A. Biochemistry 35, 15558-15569.

Reference 8: Graille, M., Stura, E. A., Corper, A. L., Sutton, B. J., Taussig, M. J., Charbonnier, J. B., Silverman, G. J. (2000) Crystal structure of a *Staphylococcus aureus* protein A domain complexed with the Fab fragment of a human IgM antibody: structural basis for recognition of B-cell receptors and superantigen activity. Proc. Natl. Acad. Sci. USA, 97, 5399-5404.

Reference 9: D'souza V M, Holz R C. (1999) The methionyl aminopeptidase from *Escherichia coli* can function as an iron(II) enzyme. Biochemistry 38, 11079-11085.

Reference 10: Japanese Patent Laid-Open No. 63-267281

Reference 11: Japanese Patent Laid-Open No. 2005-112827

Reference 12: Horton R. M., Hunt H. D., Ho S. N., Pullen J. M. and Pease L. R. (1989). Engineering hybrid genes without the use of restriction enzymes: gene splicing by overlap extension. Gene 77, 61-68.

Reference 13: Masato Okada and Kaoru Miyazaki (2004), Tanpakushitsu Jikken Noto, Jyo (Notebook for Protein Experiments, Vol. 1, in English), Yodosha Co., Ltd.

Reference 14; ed. by Shigeo Ono and Yoshifumi Nishimura (1997), Tanpakushitsu Jikken Protocol 1-Kinou Kaiseki Hen (Protein Experimental Protocol 1-Functional Analysis in English), Shujunsha Co., Ltd.

Reference 15; ed. by Shigeo Ono and Yoshifumi Nishimura (1997), Tanpakushitsu Jikken Protocol 2-Kouzou Kaiseki Hen (Protein Experimental Protocol 2-Structural Analysis in English), Shujunsha Co., Ltd.

Hereinafter, the present invention will be described specifically with reference to Examples. However, the technical scope of the present invention is not intended to be limited by these Examples.

In the present specification, each amino acid residue is abbreviated as follows: L-alanine residue: Ala, L-arginine residue: Arg, L-aspartic acid residue: Asp, L-asparagine residue: Asn, L-cysteine residue: Cys, L-glutamine residue: Gln, L-glutamic acid residue: Glu, L-glycine residue: Gly, L-histidine residue: His, L-isoleucine residue: Ile, L-leucine residue: Leu, L-lysine residue: Lys, L-methionine residue: Met, L-phenylalanine residue: Phe, L-proline residue: Pro, L-serine residue: Ser, L-threonine residue: Thr, L-tryptophan residue: Trp, L-tyrosine residue: Tyr, and L-valine residue: Val. In the present specification, the amino acid sequence of each peptide is described according to the standard method such that the amino terminus (hereinafter, referred to as an N-terminus) thereof is positioned on the left side and the carboxyl terminus (hereinafter, referred to as a C-terminus) thereof is positioned on the right side.

In the present specification, a base in each nucleic acid is abbreviated as follows: adenine: A, thymine: T, uracil: U, guanine: G, and cytosine: C. Also, the following abbreviations are used for mixed bases: R=(A or G), Y=(C or T), M=(A or C), K=(G or T), S=(G or C), W=(A or T), H=(A, C, or T), B=(G, T, or C), V=(G, C, or A), D=(G, A, or T), and N=(A, C, G, or T). Thymine (T) in DNA corresponds to uracil (U) in RNA. Sequence information at the DNA level also encompasses sequence information at the RNA level. In the present specification, the nucleotide sequences of DNA and RNA are described according to the standard method such that the 5' end thereof is positioned on the left side and the 3' end thereof is positioned on the right side.

EXAMPLE 1

Figure 4:
FIG. 4 is a diagram showing the three-dimensional structure of a complex of the B domain of protein A and the Fc region of human immunoglobulin G.

1) Selection of Mutation Site in Protein A Extracellular Domain and Amino Acid Residue for Substitution First, three-dimensional structure coordinate data on a complex of the B domain of protein A and the Fc region of human immunoglobulin G was downloaded from the international protein three-dimensional structure database Protein Data Bank (PDB; www.rcsb.org/pdb/home/home.do) (PDB code: 1FC2). Subsequently, amino acid residues of the B domain of protein A that were located within the range of 10 angstroms from the Fc region and had a 20% or more ratio of exposed surface area in the case of the B domain alone of protein A were calculated using the three-dimensional structure coordinate data and selected as sites to be mutated. The amino acid residues of the selected sites are 18 residues in the wild-type amino acid sequence of the B domain of protein A represented by [SEQ ID NO: 1]: Phe5, Asn6, Gln9, Gln10, Asn11, Phe13, Tyr14, Glu15, Leu17, His18, Glu24, Glu25, Arg27, Asn28, Ile31, Gln32, Lys35, and Asp36. FIG. 4 shows the positions of these sites to be mutated on the structure of the complex.

The extracellular domains of protein A have high sequence homology to each other (FIG. 2). In addition, the D, E, and Z domains whose three-dimensional structures have been revealed experimentally rarely differ in structure from the B domain alone (References 5 to 8). Thus, findings about the three-dimensional structure of the B domain-Fc complex can also be applied to E, D, A, C, and Z domain-Fc complexes.

Specifically, although the three-dimensional structures of the E domain-Fc complex, the D domain-Fc complex, the A domain-Fc complex, the C domain-Fc complex, and the Z domain-Fc complex have not yet been revealed, the deduction that the E, D, A, C, and Z domain-Fc complexes form a structure homologous to that of the B domain-Fc complex can be drawn naturally on the basis of the sequence homology of each extracellular domain and similarity in the three-dimensional structures of the B, D, E, and Z domains alone. Thus, the selected 18 sites to be mutated are strongly expected to be positioned, also in the E, D, A, C, and Z domain-Fc complexes, in spatial arrangement equivalent to that in the B domain-Fc complex. These 18 sites to be mutated (residues 5, 6, 9, 10, 11, 13, 14, 15, 17, 18, 24, 25, 27, 28, 31, 32, 35, and 36) derived from the three-dimensional structure of the B domain-Fc complex can be selected as sites to be mutated in the B domain as well as the D, A, C, and Z domains.

Specifically, the amino acid residues of the selected sites are 18 residues Phe5, Asn6, Gln9, Gln10, Asn11, Phe13, Tyr14, Glu15, Leu17, His18, Glu24, Glu25, Arg27, Asn28, Ile31, Gln32, Lys35, and Asp36 in the wild-type amino acid sequence of the B domain of protein A represented by [SEQ ID NO: 1], 18 residues Phe5, Asn6, Gln9, Gln10, Asn11, Phe13, Tyr14, Glu15, Leu17, His18, Glu24, Glu25, Arg27, Asn28, Ile31, Gln32, Lys35, and Asp36 in the amino acid sequence of the Z domain of protein A set forth in [SEQ ID NO: 2], 18 residues His5, Asp6, Gln9, Gln10, Asn11, Phe13, Tyr14, Glu15, Leu17, Asn18, Ala24, Asp25, Arg27, Asn28, Ile31, Gln32, Lys35, and Asp36 in the wild-type amino acid sequence of the E domain of protein A set forth in [SEQ ID NO: 3], 18 residues Phe5, Asn6, Gln9, Gln10, Ser11, Phe13, Tyr14, Glu15, Leu17, Asn18, Glu24, Ala25, Arg27, Asn28, Ile31, Gln32, Lys35, and Asp36 in the wild-type amino acid sequence of the D domain of protein A set forth in [SEQ ID NO: 4], 18 residues Phe5, Asn6, Gln9, Gln10, Asn11, Phe13, Tyr14, Glu15, Leu17, Asn18, Glu24, Glu25, Arg27, Asn28, Ile31, Gln32, Lys35, and Asp36 in the wild-type amino acid sequence of the A domain of protein A set forth in [SEQ ID NO: 5], and 18 residues Phe5, Asn6, Gln9, Gln10, Asn11, Phe13, Tyr14, Glu15, Leu17, His18, Glu24, Glu25, Arg27, Asn28, Ile31, Gln32, Lys35, and Asp36 in the wild-type amino acid sequence of the C domain of protein A set forth in [SEQ ID NO: 6].

On the other hand, the best amino acid residue that substitutes each of the original amino acid residues at the sites to be mutated is histidine. This is because histidine largely varies in chemical state due to the dissociation of side chain protons between a neutral region and a weakly acidic region and therefore, can largely change the ability of each domain of protein A to bind to antibodies between the neutral region and the weakly acidic region. Thus, mutation sites in each modified protein A extracellular domain and amino acid residues for substitution were selected as follows:

Mutant of the B domain of protein A; any one or more of Phe5His, Asn6His, Gln9His, Gln10His, Asn11His, Phe13His, Tyr14His, Glu15His, Leu17His, Glu24His, Glu25His, Arg27His, Asn28His, Ile31His, Gln32His, Lys35His, and Asp36H is.

Mutant of the Z domain of protein A; any one or more of Phe5His, Asn6His, Gln9His, Gln10His, Asn11His, Phe13His, Tyr14His, Glu15His, Leu17His, Glu24His, Glu25His, Arg27His, Asn28His, Ile31His, Gln32His, Lys35His, and Asp36H is.

Mutant of the E domain of protein A; any one or more of Asp6His, Gln9His, Gln10His, Asn11His, Phe13His, Tyr14His, Gln15His, Leu17His, Asn18His, Ala24His, Asp25His, Arg27His, Asn28His, Ile31His, Gln32His, Lys35His, and Asp36H is.

Mutant of the D domain of protein A; any one or more of Phe5His, Asn6His, Gln9His, Gln10His, Ser11His, Phe13His, Tyr14His, Glu15His, Leu17His, Asn18His, Glu24His, Ala25His, Arg27His, Asn28His, Ile31His, Gln32His, Lys35His, and Asp36H is.

Mutant of the A domain of protein A; any one or more of Phe5His, Asn6His, Gln9His, Gln10His, Asn11His, Phe13His, Tyr14His, Glu15His, Leu17His, Asn18His, Glu24His, Glu25His, Arg27His, Asn28His, Ile31His, Gln32His, Lys35His, and Asp36H is.

Mutant of the C domain of protein A; any one or more of Phe5His, Asn6His, Gln9His, Gln10His, Asn11His, Phe13His, Tyr14His, Glu15His, Leu17His, Glu24His, Glu25His, Arg27His, Asn28His, Ile31His, Gln32His, Lys35His, and Asp36H is.

In this context, the wild-type amino acid at residue in the E domain and residue 18 in the B, C, and Z domains is histidine. The substitution of these residues by histidine causes no change between before and after the substitution. Thus, His5His in the E domain and His18His in the B, C, and Z domains are excluded therefrom.

In this Example, calculation was performed using ccp4i 4.0 (Daresbury Laboratory, UK Science and Technology Facilities Council), Surface Racer 3.0 for Linux® (Dr. Oleg Tsodikov, The University of Michigan), Red Hat Enterprise Linux® WS release 3 (Red Hat, Inc.) (all are software), Dell Precision Workstation 370 (Dell Inc.) (hardware).

EXAMPLE 2

2) Selection of Preferred Mutation Site by Screening Experiment of Mutated Protein A Library Of the 18 sites to be mutated (residues 5, 6, 9, 10, 11, 13, 14, 15, 17, 18, 24, 25, 27, 28, 31, 32, 35, and 36) derived from the three-dimensional structure of the B domain-Fc complex, preferred sites to be mutated that could be expected to produce higher effects were selected. The total number of mutants in which any one or more of these 18 sites to be mutated is substituted by a histidine residue is theoretically 262,143 ($=2^{18}-1$) provided that each site is either wild-type amino acid residue or histidine residue. In order to identify a mutant that can be expected to have higher effects from among such a large number of mutants, a mutated protein A library can be constructed by use of a molecular evolution engineering technique and appropriately screened to select favorable mutants. The amino acid sequences of the obtained favorable mutants can be further analyzed statistically to select preferred sites to be mutated that can be expected to produce higher effects.

2-1) Preparation of Gene Library

A gene library necessary for constructing the mutated protein A library was prepared by first chemically synthesizing polynucleotides having the nucleic acid sequences represented by [SEQ ID NO: 32] to [SEQ ID NO: 35] and subsequently performing an overlap extension method (Reference 12) using combinations of these polynucleotides.

The polynucleotides having the nucleic acid sequences represented by [SEQ ID NO: 32] to [SEQ ID NO: 35] correspond to a portion of the nucleic acid sequence encoding the B domain protein of protein A consisting of the amino acid sequence represented by [SEQ ID NO: 1] and have, at their ends, complementary regions of approximately 20 bases long necessary for overlap.

In the sequence represented by [SEQ ID NO: 32], an EcoRI restriction site having the nucleotide sequence GAATTC, the nucleotide sequence GGCGGTGGAGGC encoding a glycine linker (GlyGlyGlyGly), and an NcoI restriction site having the nucleotide sequence CCATGG were added to the 5'-terminal side of the nucleic acid fragment of the B domain of protein A. In the sequence represented by [SEQ ID NO: 35], a HindIII restriction site having the nucleotide sequence AAGCTT was added to the 3'-terminal side of the nucleic acid fragment of the B domain of protein A.

Mixed bases capable of encoding both wild-type amino acid and histidine were introduced to positions corresponding to the 18 sites to be mutated. Specifically, YWT capable of encoding both Phe and His was introduced to positions corresponding to residue 5; MAY capable of encoding both Asn and His was introduced to positions corresponding to residue 6; CAW capable of encoding both Gln and His was introduced to positions corresponding to residue 9; CAW capable of encoding both Gln and His was introduced to positions corresponding to residue 10; MAY capable of encoding both Asn and His was introduced to positions corresponding to residue 11; YWT capable of encoding both Phe and His was introduced to positions corresponding to residue 13; YAT capable of encoding both Tyr and His was introduced to positions corresponding to residue 14; SAW capable of encoding both Glu and His was introduced to positions corresponding to residue 15; CWK capable of encoding both Leu and His was introduced to positions corresponding to residue 17; SAW capable of encoding both Glu and His was introduced to positions corresponding to residue 24; SAW capable of encoding both Glu and His was introduced to positions corresponding to residue 25; CRY capable of encoding both Arg and His was introduced to positions corresponding to residue 27; MAY capable of encoding both Asn and His was introduced to positions corresponding to residue 28; MWT capable of encoding both Ile and His was introduced to positions corresponding to residue 31; CAW capable of encoding both Gln and His was introduced to positions corresponding to residue 32; MAW capable of encoding both Lys and His was introduced to positions corresponding to residue 35; and SAT capable of encoding both Asp and His was introduced to positions corresponding to residue 36.

Depending on combinations in the mixed bases, not only wild-type amino acid and histidine but the third amino acid may be encoded. For example, YWT used for residue 5 achieves four sequences TTT, TAT, CTT, and CAT, which encode Phe, Tyr, Leu, and His, respectively. Thus, Tyr or Leu might be introduced as the third amino acid to the residue 5. As a result of calculating the sequence diversity of the library, including the presence of these third amino acids, $3.4 \times 10^7$ and $2.5 \times 10^7$ molecular species shall be prepared theoretically in terms of nucleic acid sequences and amino acid sequences, respectively.

2-2) Construction of Mutated Protein A Library by T7 Phage Display Method

The gene library thus designed and synthesized was treated with restriction enzymes EcoRI and HindIII and linked to the 3'-terminal side of g10 gene on the T7 phage genome through ligation reaction (16° C., 16 hr) with T7 phage vectors (Novagen).

The T7 genome was treated with a reagent of T7 Select 1-1b (Novagen) according to the procedures of T7 Select® System Manual included therein. The linked T7 phage genome was subjected to in vitro T7 phage particle packaging reaction (22° C., 2 hr) to prepare phages. At this point in time, the phage library was examined by plaque assay and consequently confirmed to form approximately $5.4 \times 10^7$ phages.

An *E. coli* BLT5403 strain cultured in 200 mL of an LB medium until O.D.600=1.0 was infected using this initial library, followed by amplification operation. Approximately 4 hours after the infection, the amplified phages were recovered (T7 phages have bacteriolytic effect and are thus released from the bacterial body by destroying *E. coli* after amplification) from the supernatant solution by centrifugation operation. To the recovered supernatant solution, ⅙ volume of a 50% polyethylene glycol (PEG, molecular weight: 8000) solution and ⅒ volume of a 5M NaCl solution were added, and the mixture was stirred at 4° C. all night and all day.

Then, the phages were PEG-precipitated and partially purified by centrifugation operation. The PEG-precipitated phages were lysed in a TST buffer (10 mM Tris-HCl (pH 7.5), 150 mM NaCl, and 0.1% Tween 20) and filtered through a particle removal filter having a pore size of 0.22 μm. In this way, a solution of a phage library displaying the mutated B domain of protein A was prepared.

2-3) Human Monoclonal Antibody Binding Screening

First, 500 μL of a monoclonal antibody (human immunoglobulin G1) solution (concentration: 3.36 μM) was mixed with 25 μl of a solution containing 1.4 mg of D-biotinoyl-ϵ-aminocaproic acid-N-hydroxy-succinimide ester (Roche) dissolved in 50 μl of dimethyl sulfoxide and reacted for 3 hours. Unreacted D-biotinoyl-ϵ-aminocaproic acid-N-hydroxy-succinimide ester was removed to prepare biotinylated monoclonal antibodies.

Subsequently, 500 μl of this biotinylated monoclonal antibody solution (concentration: 0.5 to 0.6 μM) was mixed with 0.6 mL of streptavidin magnetic beads (Promega) to immobilize the antibodies onto the magnetic beads. The above-prepared solution of a phage library displaying the mutated B domain of protein A was added to 0.65 mL of the biotinylated antibody-immobilized magnetic beads, and the mixture was left under shaking at 25° C. for 1 hour. Then, washing operation was performed approximately 10 to 20 times using a TST buffer (10 mM Tris-HCl (pH 7.5), 150 mM NaCl, and 0.1% Tween 20) to remove antibody-unbound phages.

In order to recover phages specifically bound with the antibodies, a 50 mM sodium acetate solution (pH 5.0) was added thereto and fully mixed, followed by elution. The eluted phages were subjected to the infection-amplification-PEG precipitation operation described in the preceding paragraph 2-2) to prepare again a solution of a phage library displaying the mutated B domain of protein A.

The operation of the paragraphs 2-2) and 2-3) was defined as one round of the phage display method, and 5 rounds in total of the screening experiment were repetitively performed. In this context, the eluting solution used in the screening experiment was a 50 mM sodium acetate solution of pH 6.0 from the second round, and the selective pressure of screening was changed at stages with the amount of streptavidin magnetic beads (Promega) gradually decreased.

2-4) Sequence Analysis of Favorable Mutant Selected by Screening

After the 5-round screening experiment, the phages in the eluate were cloned on an LB medium plate using plaque assay. Then, an *E. coli* BLT5403 strain cultured until O.D.600=1.0 was added at a concentration of 200 μL/well to a 96-well plate and infected with the phages by the stirring of the wells using a toothpick with which plaques on the LB medium plate were poked. The phages cause bacteriolysis by culture at 37° C. all night and all day to form a cloned phage solution.

In order to confirm the amino acid sequence of the mutated B domain of protein A displayed by the phages thus prepared, 1 μL of the phage solution from the 96-well plate was mixed with a PCR reaction solution. Phage DNA was isolated by heat treatment and subjected to PCR (annealing: 53° C., 5 sec) to amplify the gene of the mutated protein A.

The primers used were a sense primer (SEQ ID NO: 36) and an antisense primer (SEQ ID NO: 37). The sense primer (SEQ ID NO: 36) encodes the sequence of g10 gene on the T7 phage genome, while the antisense primer (SEQ ID NO: 37) encodes the C-terminal sequence of the B domain of protein A and a HindIII restriction site having the nucleotide sequence AAGCTT. The obtained amplification product was treated with Exonuclease (New England Biolabs) and Antarctic Phosphatase (New England Biolabs). Then, the nucleotide sequence of the nucleic acid was analyzed by DNA sequencing (GE Healthcare Bioscience, BigDye Terminator v1.1).

The nucleic acid sequence of the mutated B domain of protein A located at the 3'-terminal side of the g10 gene in 91 types in total of cloned phages was determined and consequently confirmed to fit into any of 16 sequences of [SEQ ID NOs: 28, 29, and 43 to 56]. The amino acid sequences corresponding to these 16 nucleic acid sequences are 16 sequences of [SEQ ID NOs: 7, 8, and 14 to 27].

2-5) Statistical Analysis of Amino Acid Sequence of Favorable Mutant

These 16 amino acid sequences obtained from the 91 types of cloned phages are only a portion of a favorable mutant group that was selected by binding screening and can be expected to have higher effect. Specifically, the 16 amino acid sequences can be regarded as samples with the favorable mutants as a population. The samples can therefore be analyzed statistically to predict an average of the population.

Table 1 shows the type of an amino acid substitution that occurred at each site to be mutated, which was determined from the 16 amino acid sequences. The value of the frequency of appearance shown in Table 1 serves as an index for whether or not the substitution of the underlined wild-type amino acid by a histidine residue at each site to be mutated is appropriate. For example, at residue 5, Phe has a value of 0.19, whereas His has a value as high as 0.63, which shows that the residue 5 is preferred as a site to be mutated that can be expected to produce so higher effects that a mutant obtained as a result of the substitution by histidine has a reduced binding activity in an acidic region while maintaining its binding activity in a neutral region. Similar analysis reveals that the residue 5 as well as residues 9, 10, 11, 15, 27, 28, 35, and 36 are preferred as sites to be mutated. Of the 18 sites to be mutated selected in the paragraph 1), 10 residues, i.e., residues 5, 9, 10, 11, 15, 18, 27, 28, 35, and 36, in addition to residue 18 at which the wild-type amino acid is originally a histidine residue, were shown to be preferred sites to be mutated.

These 10 preferred sites to be mutated can be selected, as mentioned in the paragraph 1), as sites to be mutated in the B domain of protein A as well as the D, A, C, and Z domains.

Specifically, the amino acid residues at the sites selected as preferred sites to be mutated are 10 residues Phe5, Gln9, Gln10, Asn11, Glu15, His18, Arg27, Asn28, Lys35, and Asp36 in the wild-type amino acid sequence of the B domain of protein A set forth in [SEQ ID NO: 1], 10 residues Phe5, Gln9, Gln10, Asn11, Glu15, His18, Arg27, Asn28, Lys35, and Asp36 in the wild-type amino acid sequence of the Z domain of protein A set forth in [SEQ ID NO: 2], 10 residues His5, Gln9, Gln10, Asn11, Glu15, Asn18, Arg27, Asn28, Lys35, and Asp36 in the wild-type amino acid sequence of the E domain of protein A set forth in [SEQ ID NO: 3], 10 residues Phe5, Gln9, Gln10, Ser11, Glu15, Asn18, Arg27, Asn28, Lys35, and Asp36 in the wild-type amino acid sequence of the D domain of protein A set forth in [SEQ ID NO: 4], 10 residues Phe5, Gln9, Gln10, Asn11, Glu15, Asn18, Arg27, Asn28, Lys35, and Asp36 in the wild-type amino acid sequence of the A domain of protein A set forth in [SEQ ID NO: 5], and 10 residues Phe5, Gln9, Gln10, Asn11, Glu15, His18, Arg27, Asn28, Lys35, and Asp36 in the wild-type amino acid sequence of the C domain of protein A set forth in [SEQ ID NO: 6].

Thus, preferred ones of mutation sites in each modified protein A extracellular domain selected in the paragraph 1) and amino acid residues for substitution were selected as follows:

Mutant of the B domain of protein A; any one or more of Phe5His, Gln9His, Gln10His, Asn11His, Glu15His, Arg27His, Asn28His, Lys35His, and Asp36H is.

Mutant of the Z domain of protein A; any one or more of Phe5His, Gln9His, Gln10His, Asn11His, Glu15His, Arg27His, Asn28His, Lys35His, and Asp36H is.

Mutant of the E domain of protein A; any one or more of Gln9His, Gln10His, Asn11His, Gln15His, Asn18His, Arg27His, Asn28His, Lys35His, and Asp36H is.

Mutant of the D domain of protein A; any one or more of Phe5His, Gln9His, Gln10His, Ser11His, Glu15His, Asn18His, Arg27His, Asn28His, Lys35His, and Asp36H is.

TABLE 1

| | SEQ ID NO | | | | | | | | | | | |
|---|---|---|---|---|---|---|---|---|---|---|---|---|
| | 5 | | 6 | | 9 | | 10 | | 11 | | 13 | |
| Amino acid (frequency of appearance) | Phe | 0.19 | Asn | 0.69 | Gln | 0.25 | Gln | 0.19 | Asn | 0.44 | Phe | 0.38 |
| | His | 0.63 | His | 0.31 | His | 0.75 | His | 0.81 | His | 0.56 | His | 0.06 |
| | Tyr | 0.06 | | | | | | | | | Tyr | 0.06 |
| | Leu | 0.13 | | | | | | | | | Leu | 0.50 |

| | SEQ ID NO | | | | | | | | | | | |
|---|---|---|---|---|---|---|---|---|---|---|---|---|
| | 14 | | 15 | | 17 | | 24 | | 25 | | 27 | |
| Amino acid (frequency of appearance) | Tyr | 0.88 | Glu | 0.13 | Leu | 0.88 | Glu | 0.56 | Glu | 0.25 | Arg | 0.25 |
| | His | 0.13 | His | 0.44 | His | 0.06 | His | 0.19 | His | 0.25 | His | 0.75 |
| | | | Asp | 0.19 | Gln | 0.06 | Asp | 0.0 | Asp | 0.31 | | |
| | | | Gln | 0.25 | | | Gln | 0.25 | Gln | 0.19 | | |

| | SEQ ID NO | | | | | | | | | |
|---|---|---|---|---|---|---|---|---|---|---|
| | 28 | | 31 | | 32 | | 35 | | 36 | |
| Amino acid (frequency of appearance) | Asn | 0.38 | Ile | 0.44 | Gln | 0.63 | Lys | 0.19 | Asp | 0.13 |
| | His | 0.63 | His | 0.13 | His | 0.38 | His | 0.81 | His | 0.88 |
| | | | Asn | 0.0 | | | Asn | 0.0 | | |
| | | | Leu | 0.44 | | | Gln | 0.0 | | |

Mutant of the A domain of protein A; any one or more of Phe5His, Gln9His, Gln10His, Asn11His, Glu15His, Asn18His, Arg27His, Asn28His, Lys35His, and Asp36H is.

Mutant of the C domain of protein A; any one or more of Phe5His, Gln9His, Gln10His, Asn11His, Glu15His, Arg27His, Asn28His, Lys35His, and Asp36H is.

As mentioned in the paragraph 1), the wild-type amino acid at residue 5 in the E domain and residue 18 in the B, C, and Z domains is histidine. The substitution of these residues by histidine causes no change between before and after the substitution. Thus, His5His in the E domain and His18His in the B, C, and Z domains are excluded therefrom.

EXAMPLE 3

3) Design of Modified Protein A Extracellular Domain

As is evident from above, the sites to be mutated selected in the design of the modified protein of the present invention are not limited to one residue.

Appropriate residues can be selected from among a plurality of sites to be mutated and combined to prepare a point mutant or a multiple mutant as the modified protein. This selection may be performed at random or in consideration of other pieces of information known in the art, such as structure activity correlation. Alternatively, these mutations may be combined with a mutation already known to change the properties of the protein A extracellular domain to preferred ones.

The modified protein may have, for example, the amino acid sequence of an Asn6His/Asn11His/Glu15Asp/Glu24Gln/Glu25His quintuple mutant of the B domain of protein A represented by [SEQ ID NO: 7], or an Asn6His/Glu24His/Glu25Gln/Gln32His/Asp36His quintuple mutant of the B domain of protein A represented by [SEQ ID NO: 8], which were obtained by the screening experiment of the phage display method. Also, the modified protein may have the amino acid sequence of an Asn6His/Glu24His/Glu25Gln/Gln32His/Asp36His quintuple mutant of the Z domain of protein A represented by [SEQ ID NO: 9] in which five mutations Asn6His, Glu24His, Glu25Gln, Gln32His, and Asp36His in the quintuple mutant of [SEQ ID NO: 8] obtained by the screening experiment on the B domain are introduced in the amino acid sequence of the Z domain of protein A represented by [SEQ ID NO: 2].

Alternatively, the modified protein may have, for example, the amino acid sequence of an Asn6His point mutant (SEQ ID NO: 10) of the B domain of protein A containing histidine introduced at residue 6, a Glu24His point mutant (SEQ ID NO: 11) of the B domain of protein A containing histidine introduced at residue 24, a Gln32His point mutant (SEQ ID NO: 12) of the B domain of protein A containing histidine residue introduced at residue 32, an Asp36His point mutant (SEQ ID NO: 13) of the B domain of protein A containing histidine residue introduced at residue 36, a Gln9His point mutant (SEQ ID NO: 61) of the B domain of protein A containing histidine residue introduced at residue 9, a Gln10His point mutant (SEQ ID NO: 62) of the B domain of protein A containing histidine residue introduced at residue 10, a Glu15His point mutant (SEQ ID NO: 63) of the B domain of protein A containing histidine residue introduced at residue 15, an Arg27His point mutant (SEQ ID NO: 64) of the B domain of protein A containing histidine residue introduced at residue 27, a Gln9His/Asp36His double mutant (SEQ ID NO: 65) of the B domain of protein A containing histidine residues introduced at residues 9 and 36, a Gln10His/Asp36His double mutant (SEQ ID NO: 66) of the B domain of protein A containing histidine residues introduced at residues 10 and 36, a Glu15His/Asp36His double mutant (SEQ ID NO: 67) of the B domain of protein A containing histidine residues introduced at residues 15 and 36, an Arg27His/Asp36His double mutant (SEQ ID NO: 68) of the B domain of protein A containing histidine residues introduced at residues 27 and 36, a Lys35His/Asp36His double mutant (SEQ ID NO: 69) of the B domain of protein A containing histidine residues introduced at residues 35 and 36, a Gln9His/Gln32His double mutant (SEQ ID NO: 70) of the B domain of protein A containing histidine residues introduced at residues 9 and 32, a Gln10His/Gln32His double mutant (SEQ ID NO: 71) of the B domain of protein A containing histidine residues introduced at residues 10 and 32, an Asp36His point mutant (SEQ ID NO: 72) of the Z domain of protein A containing histidine residue introduced at residue 36, an Asp36His point mutant (SEQ ID NO: 74) of the C domain of protein A containing histidine residue introduced at residue 36, a Gln9His point mutant (SEQ ID NO: 75) of the Z domain of protein A containing histidine residue introduced at residue 9, or a Gln9His/Asp36His double mutant (SEQ ID NO: 76) of the C domain of protein A containing histidine residues introduced at residues 9 and 36.

Of the modified protein A extracellular domains of the present invention, the amino acid sequences represented by [SEQ ID NO: 7] to [SEQ ID NO: 13], [SEQ ID NO: 61] to [SEQ ID NO: 72], and [SEQ ID NO: 74] to [SEQ ID NO: 76] were selected as specific examples in Examples below, and mutated proteins represented by these sequences were actually synthesized. In addition, the wild-type B domain of protein A represented by [SEQ ID NO: 1], the Z domain of protein A represented by [SEQ ID NO: 2], and the wild-type C domain of protein A represented by [SEQ ID NO: 6] were also synthesized and compared therewith to evaluate the molecular properties of the modified proteins.

4) Design of Nucleotide Sequence of Nucleic Acid Encoding Amino Acid Sequence of Modified Protein A Extracellular Domain The nucleotide sequences ([SEQ ID NO: 28] to [SEQ ID NO: 30], [SEQ ID NO: 57] to [SEQ ID NO: 60], and [SEQ ID NO: 77] to [SEQ ID NO: 91]) of genes encoding the modified protein A extracellular domains were designed on the basis of the amino acid sequences of these modified protein A extracellular domains. Since these modified proteins are produced as simple proteins without a tag or fusion using *E. coli*, start codon sequences are added to the 5' ends of the designed nucleotide sequences of the genes. As a result, the wild-type B domain of protein A or modified proteins M-PAB are synthesized to have an amino acid sequence containing Met added to the N terminus of any of [SEQ ID NO: 1], [SEQ ID NO: 7], [SEQ ID NO: 8], [SEQ ID NO: 10] to [SEQ ID NO: 13], and [SEQ ID NO: 61] to [SEQ ID NO: 71]. The wild-type Z domain of protein A or modified proteins M-PAZ are synthesized to have an amino acid sequence containing Met added to the N terminus of [SEQ ID NO: 2], [SEQ ID NO: 9], or [SEQ ID NO: 72]. The wild-type C domain of protein A or modified proteins M-PAC are synthesized to have an amino acid sequence containing Met added to the N terminus of any of [SEQ ID NO: 6] and [SEQ ID NO: 74] to [SEQ ID NO: 76]. These proteins may be synthesized with their N-terminal Met selectively cleaved by the action of an enzyme such as methionyl aminopeptidase present in *E. coli*.

5) Production of Modified Protein A Extracellular Domain

As shown below, a plasmid vector containing the gene encoding the wild-type or modified B domain, Z domain, or C domain of protein A was first synthesized.

Subsequently, the Met-added wild-type (M-PAB01) and modified (M-PAB2 to 19) B domains of protein A, wild-type (M-PAZ01) and modified (M-PAZ03 and M-PAZ08) Z domains of protein A, and wild-type (M-PAC01) and modified (M-PAC08, M-PAC09, and M-PAC13) C domains of protein A were produced using *E. coli*. The configuration of the amino acid sequences of these proteins and mutations therein are shown in Table 2.

TABLE 2

| Name | Amino acid sequence | Mutation site |
| --- | --- | --- |
| M-PAB01 | Amino acid sequence containing Met added to N-terminus of (SEQ ID NO: 1) | Wild-type sequence of 8 domain of protein A |
| M-PAB02 | Amino acid sequence containing Met added to N-terminus of (SEQ ID NO: 7) | quintuple substitution mutation of Asn6His/Asn11His/Glu15Asp/Glu24Gln/Glu25His |
| M-PAB03 | Amino acid sequence containing Met added to N-terminus of (SEQ ID NO: 8) | quintuple substitution mutation of Asn6His/Glu24His/Glu25Gln/Gln32His/Asp38His |
| M-PAB04 | Amino acid sequence containing Met added to N-terminus of (SEQ ID NO: 10) | substitution mutation of Asn6His |
| M-PAB05 | Amino acid sequence containing Met added to N-terminus of (SEQ ID NO: 11) | substitution mutation of Glu24His |
| M-PAB07 | Amino acid sequence containing Met added to N-terminus of (SEQ ID NO: 12) | substitution mutation of Glu32His |
| M-PAB08 | Amino acid sequence containing Met added to N-terminus of (SEQ ID NO: 13) | substitution mutation of Asn36His |
| M-PAB09 | Amino acid sequence containing Met added to N-terminus of (SEQ ID NO: 61) | substitution mutation of Gln9His |
| M-PAB10 | Amino acid sequence containing Met added to N-terminus of (SEQ ID NO: 62) | substitution mutation of Gln10His |
| M-PAB11 | Amino acid sequence containing Met added to N-terminus of (SEQ ID NO: 63) | substitution mutation of Glu15His |
| M-PAB12 | Amino acid sequence containing Met added to N-terminus of (SEQ ID NO: 64) | substitution mutation of Arg27His |
| M-PAB13 | Amino acid sequence containing Met added to N-terminus of (SEQ ID NO: 65) | substitution mutation of Gln9His/Asp36His |
| M-PAB14 | Amino acid sequence containing Met added to N-terminus of (SEQ ID NO: 66) | substitution mutation of Gln10His/Asp36His |
| M-PAB15 | Amino acid sequence containing Met added to N-terminus of (SEQ ID NO: 67) | substitution mutation of Gln15His/Asp36His |
| M-PAB16 | Amino acid sequence containing Met added to N-terminus of (SEQ ID NO: 68) | substitution mutation of Arg27His/Asp36His |
| M-PAB17 | Amino acid sequence containing Met added to N-terminus of (SEQ ID NO: 69) | substitution mutation of Lys35His/Asp36His |
| M-PAB18 | Amino acid sequence containing Met added to N-terminus of (SEQ ID NO: 70) | substitution mutation of Gln9His/Gln32His |
| M-PAB19 | Amino acid sequence containing Met added to N-terminus of (SEQ ID NO: 71) | substitution mutation of Gln10His/Gln32His |
| M-PAZ01 | Amino acid sequence containing Met added to N-terminus of (SEQ ID NO: 2) | Original sequence of Z domain of protein A |
| M-PAZ03 | Amino acid sequence containing Met added to N-terminus of (SEQ ID NO: 9) | quintuple substitution mutation of Asn6His/Glu24His/Glu25Gln/Gln32His/Asp36His |
| M-PAZ08 | Amino acid sequence containing Met added to N-terminus of (SEQ ID NO: 72) | substitution mutation of Asp35His |
| M-PAC01 | Amino acid sequence containing Met added to N-terminus of (SEQ ID NO: 8) | Original sequence of G domain of protein A |
| M-PAC08 | Amino acid sequence containing Met added to N-terminus of (SEQ ID NO: 74) | substitution mutation of Asp36His |
| M-PAC09 | Amino acid sequence containing Met added to N-terminus of (SEQ ID NO: 75) | substitution mutation of Gln9His |
| M-PAC13 | Amino acid sequence containing Met added to N-terminus of (SEQ ID NO: 76) | substitution mutation of Gln9His/Asp36His |

5-1) Synthesis of Plasmid for M-PAB or M-PAZ Expression

As for M-PAB02 or M-PAB03, each PAB gene region was amplified through PCR (annealing: 49° C., 15 sec) by the addition of primers containing a restriction site to the corresponding phage DNA prepared in the paragraph 2) as a template.

The primers used were a sense primer (SEQ ID NO: 36) and an antisense primer (SEQ ID NO: 37). The obtained amplification product was confirmed by agarose electrophoresis (3%, 100 V) and then purified using QIAquick PCR Purification kit (Qiagen). Then, the mutant PAB gene (pab02 or pab03) digested with restriction enzymes NcoI and HindIII (Nippon Gene Co., Ltd., 37° C., all night and all day) was ligated (Toyobo Co., Ltd., Ligation High, 16° C., 1 hr) with a plasmid pET16b or pET21d (Novagen) digested with the same restriction enzymes as above and dephosphorylated (Takara Shuzo Co., Ltd., CIAP, 50° C., 30 min). An *E. coli* DH5α strain (Toyobo Co., Ltd., Competent high) for preservation was transformed with the obtained plasmid vector and selected in an LB plate medium containing 100 μg/mL ampicillin.

A transformant having the correct insertion sequence was screened for by colony PCR and DNA sequencing (GE Healthcare Bioscience, BigDye Terminator v1.1). Plasmids for M-PAB expression were extracted using Qiaprep Spin Miniprep kit (Qiagen). An *E. coli* BL21 (DE3) strain (Novagen) for expression was further transformed using the plasmids.

As for M-PAZ01, the PAZ gene region was amplified through PCR (annealing: 49° C., 15 sec) by the addition of primers containing a restriction site to a plasmid containing a nucleotide sequence encoding the Z domain of protein A represented by [SEQ ID NO: 2] as a template.

The primers used were a sense primer having the sequence CACCATGGTGGATAACAAAC and an antisense primer having the sequence TAGGATCCTTATTTTGGTGCTTGTGCATC. The obtained amplification product was confirmed by agarose electrophoresis (3%, 100 V) and then purified using QIAquick PCR Purification kit (Qiagen).

Then, the PAZ gene (paz01) digested with restriction enzymes NcoI and BamHI (Nippon Gene Co., Ltd., 37° C., all night and all day) was ligated (Toyobo Co., Ltd., Ligation High, 16° C., 1 hr) with a plasmid pET16b (Novagen) digested with the same restriction enzymes as above and dephosphorylated (Takara Shuzo Co., Ltd., CIAP, 50° C., 30 min). An *E. coli* DH5α strain (Toyobo Co., Ltd., Competent high) for preservation was transformed with the obtained plasmid vector and selected in an LB plate medium containing 100 μg/mL ampicillin. A transformant having the correct insertion sequence was screened for by colony PCR and DNA sequencing (GE Healthcare Bioscience, BigDye Terminator v1.1). Plasmids for M-PAZ expression were extracted using Qiaprep Spin Miniprep kit (Qiagen). An *E. coli* BL21 (DE3) strain (Novagen) for expression was further transformed using the plasmids.

As for M-PAB01 or M-PAZ03, nucleotide sequences encoding the B domain of protein A and the modified Z domain of protein A represented by [SEQ ID NO: 1] and [SEQ ID NO: 9], respectively, were prepared from artificially synthesized plasmids (Biomatik). First, this plasmid was digested with restriction enzymes NdeI and XhoI (Nippon Gene Co., Ltd., 37° C., all night and all day) and ligated (Toyobo Co., Ltd., Ligation High, 16° C., 1 hr) with a plasmid pET21a (Novagen) digested with the same restriction enzymes as above and dephosphorylated (Takara Shuzo Co., Ltd., CIAP, 50° C., 30 min). An *E. coli* DH5α strain (Toyobo Co., Ltd., Competent high) for preservation was transformed with the obtained plasmid vector and selected in an LB plate medium containing 100 μg/mL ampicillin. Plasmids for M-PAB01 or M-PAZ03 expression were extracted using Qiaprep Spin Miniprep kit (Qiagen). An *E. coli* BL21 (DE3) strain (Novagen) for expression was further transformed using the plasmids.

As for M-PAB04 to M-PAB08, mutations were introduced with the prepared M-PAB01 or M-PAZ01 plasmid vector as a template using QuikChange® Multi Site-Directed Mutagenesis Kit (Stratagene). The primer sequences used for this procedure are shown in [SEQ ID NO: 38] to [SEQ ID NO: 42]. Mutations were introduced with the prepared M-PAB01 plasmid vector as a template for M-PAB09 to M-PAB12, the prepared M-PAB08 plasmid vector as a template for M-PAB13 to M-PAB17, and the prepared M-PAB07 plasmid vector as a template for M-PAB18 or M-PAB19 using QuickChange® Site-Directed Mutagenesis Kit (Stratagene). The forward primer sequences used for this procedure are shown in [SEQ ID NO: 92] to [SEQ ID NO: 96], and the reverse primers used consisted of sequences complementary to the corresponding forward primer sequences. As for M-PAZ08, mutations were introduced with the prepared M-PAZ01 plasmid vector as a template using QuickChange® Multi Site-Directed Mutagenesis Kit (Stratagene). The primer sequence used for this procedure is shown in [SEQ ID NO: 42]. An *E. coli* DH5α strain (Toyobo Co., Ltd., Competent high) for preservation was transformed with each obtained plasmid vector and selected in an LB plate medium containing 100 μg/mL ampicillin. A transformant having the correct insertion sequence was screened for by colony PCR and DNA sequencing (GE Healthcare Bioscience, BigDye Terminator v1.1). Plasmids for M-PAB expression or M-PAZ expression were extracted using Qiaprep Spin Miniprep kit (Qiagen). An *E. coli* BL21 (DE3) strain (Novagen) for expression was further transformed using the plasmids. As for M-PAC01, M-PAB08, M-PAB09, or M-PAB13, plasmids (GenScript) for expression were purchased and used to transform an *E. coli* BL21 (DE3) strain (Novagen) for expression.

5-2) Expression and Purification of Recombinant Protein

The *E. coli* BL21 (DE3) transformant precultured in an LB medium was subcultured in an LB medium containing 50 μL/10 mL of 100 μg/mL ampicillin and shake-cultured until O.D.600=0.8 to 1.0. IPTG was added thereto at a final concentration of 1 mM, and the transformant was further shake-cultured at 37° C. for 2 hours. The recovered bacterial body was suspended in 10 mL of PBS and ultrasonically homogenized. The homogenate was sterilized by filtration. Then, the filtrate was added to IgG Sepharose 6 Fast Flow (GE Healthcare Bioscience) microspin equilibrated with TST (25 mM Tris-HCl (pH 7.6), 150 mM NaCl, and 0.1% Tween 20) to bind the M-PAB, M-PAZ, or M-PAC protein thereto. Unadsorbed components were washed off with TST. Then, TST was replaced with 50 mM sodium citrate (pH 7.0) and further replaced with 0.5 M acetate (pH 2.5) to elute the M-PAB, M-PAZ, or M-PAC protein. The eluate was dialyzed against 50 mM Na phosphate (pH 6.8) and then stored at 4° C.

6) Purity of Obtained Modified Protein A Extracellular Domain

The purity of each M-PAB, M-PAZ, or M-PAC protein obtained in the paragraph 5) was confirmed by polyacrylamide gel electrophoresis as follows: each protein thus purified was prepared into an aqueous solution having a concentration of approximately 75 μM, followed by tricine-SDS-PAGE (16% T, 2.6% C, 100 V, 100 min). A band was detected by CBB (G-250) staining to confirm the purity. As a result, each protein was detected as a major band in all assayed samples, demonstrating its sufficient degree of purification.

7) Immobilization of Modified Protein A Extracellular Domain

In order to evaluate each M-PAB, M-PAZ, or M-PAC protein obtained in the paragraph 5) for its properties as an affinity ligand, each protein was immobilized by a method shown below to prepare an affinity chromatography column.

A ligand protein is immobilized onto HiTrap NHS-activated HP (GE Healthcare) 1 mL column by use of an amide bond formed between N-hydroxysuccinimide (NHS) on Sepharose and primary amine on protein A. In an immobilization method, 6 mL of 1 mM HCl is injected to the column to replace therewith an isopropanol solution in the column. Then, 1 mL of a ligand protein solution (concentration: 2.6 to 2.8 mg/mL) is injected thereto and reacted at 4° C. all night and all day. Subsequently, washing operation and blocking operation are performed using solution A (0.5M Tris-HCl and 0.5M NaCl, pH 8.3) and solution B (0.1M acetate and 0.5M NaCl, pH 4.0). 6 mL of solution A, 6 mL of solution B, and 6 mL of solution A are injected in this order to the column. In this state replaced with solution A, the column is reacted at 4° C. for 6 hours to perform blocking operation through which unreacted NHS is reacted with Tris. Subsequently, 6 mL of solution B, 6 mL of solution A, and 6 mL of solution B are injected in this order to the column for washing operation. The column is equilibrated with a TST buffer (25 mM Tris-HCl (pH 7.6), 150 mM NaCl, and 0.1% Tween 20) to complete the preparation of an affinity column.

EXAMPLE 4

8) Evaluation of Modified Protein for its Ability to Bind to Antibody Using Immobilization Column (Gradient Method)

The pH at which a monoclonal antibody was eluted was examined as shown below by pH-gradient affinity chromatography using each M-PAB, M-PAZ, or M-PAC protein-immobilized column to evaluate the modified protein A for its ability to bind to antibodies in an acidic region.

First, each M-PAB, M-PAZ, or M-PAC protein-immobilized column was loaded to a liquid chromatography apparatus AKTApurifier (GE Healthcare Bioscience) and equilibrated by the injection of a TST buffer (25 mM Tris-HCl (pH 7.6), 150 mM NaCl, and 0.1% Tween 20) under conditions of 0.5 mL/min. Then, 100 to 200 µL of a 1 mg/mL sample (IgG1-type humanized monoclonal antibody) was injected thereto. Subsequently, the TST buffer was replaced with 50 mM citrate Na (pH 7.0) and further replaced continuously with a 500 mM acetic acid solution (pH 2.5) at a flow rate of 0.5 mL/min over 10 minutes to achieve a pH gradient (pH 7.0→2.5/10 min). The pH of a peak with which the monoclonal antibody was eluted was recorded from the outputs of a UV detector (280 nm) and a pH detector included in the liquid chromatography apparatus.

Figure 5:
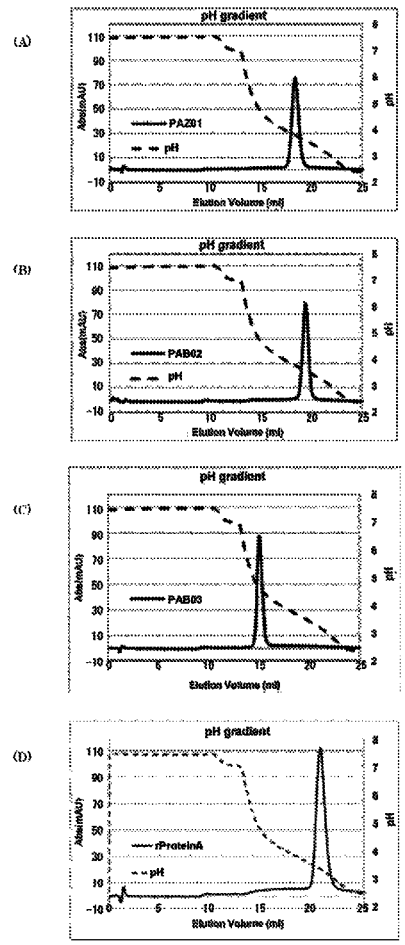
FIG. 5 is a graph showing results of evaluating (gradient method) the ability of a modified protein to bind to antibodies in an acidic region using an immobilization column.
Figure 7:
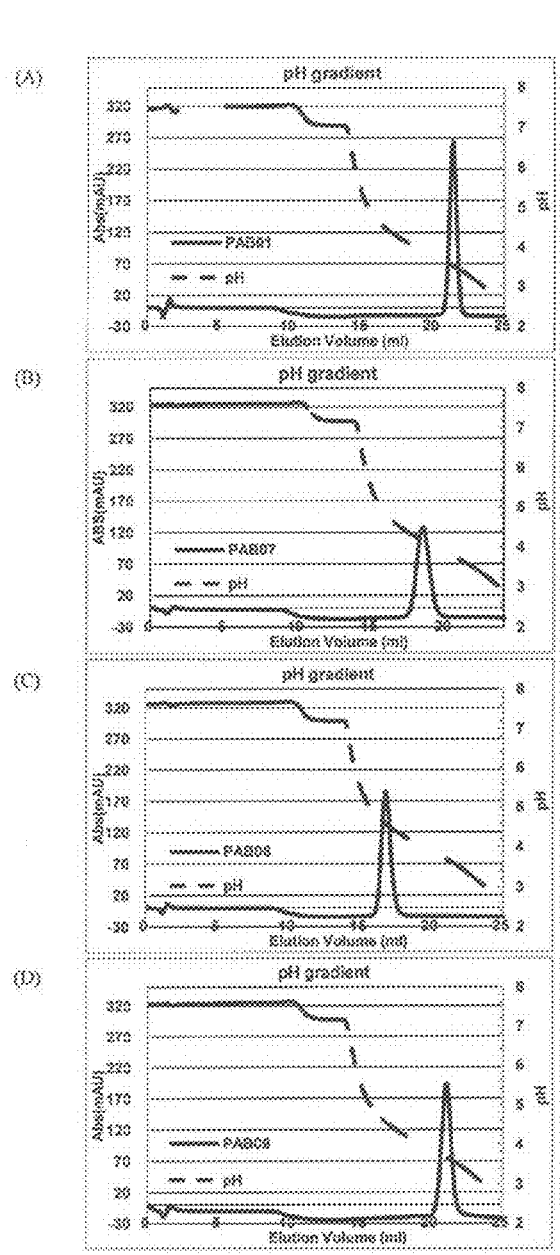
FIG. 7 is a graph showing results of evaluating (gradient method) the ability of a modified protein to bind to antibodies in an acidic region using an immobilization column.
Figure 8:
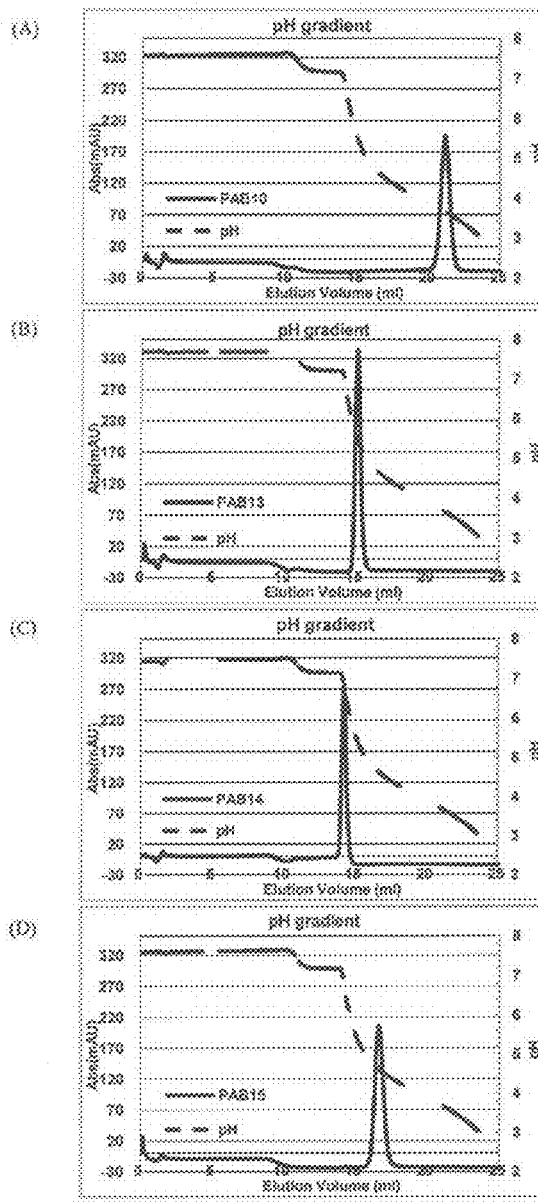
FIG. 8 is a graph showing results of evaluating (gradient method) the ability of a modified protein to bind to antibodies in an acidic region using an immobilization column.
Figure 9:
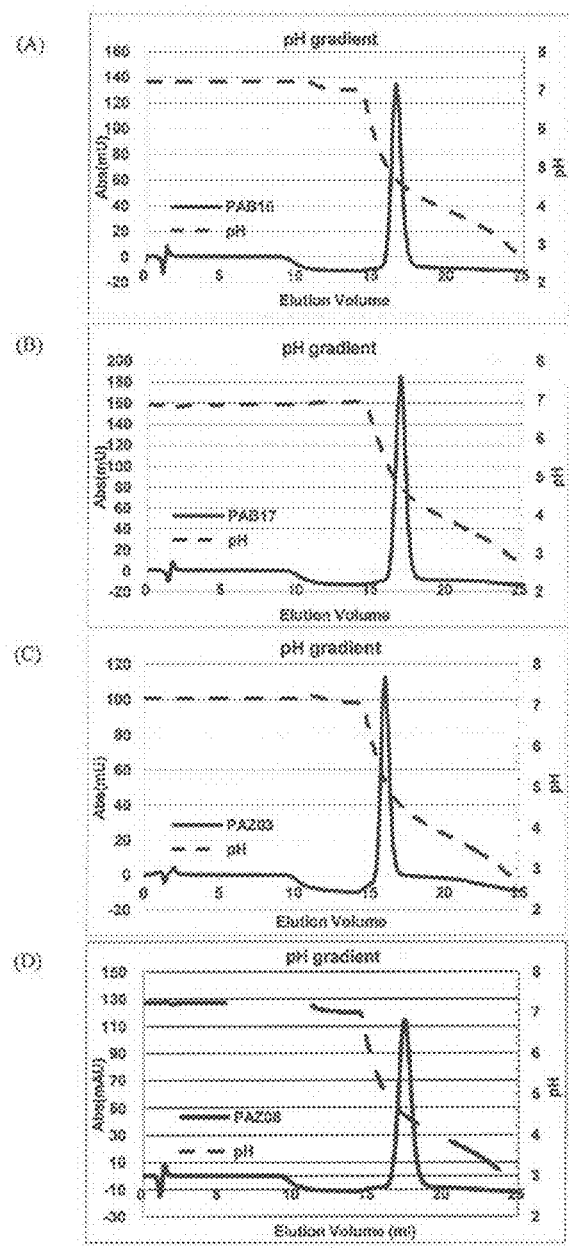
FIG. 9 is a graph showing results of evaluating (gradient method) the ability of a modified protein to bind to antibodies in an acidic region using an immobilization column.
Figure 10:
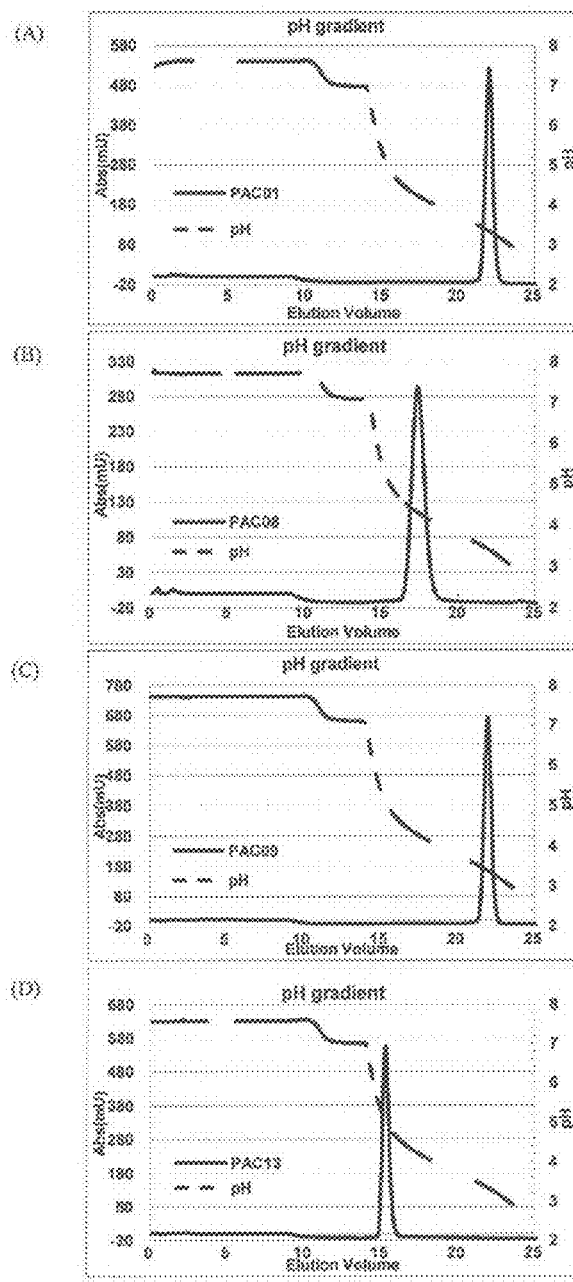
FIG. 10 is a graph showing results of evaluating (gradient method) the ability of a modified protein to bind to antibodies in an acidic region using an immobilization column.

The results demonstrated that the humanized monoclonal antibody was eluted in the M-PAB03-immobilized column at a pH approximately 1.1 points higher than that of the column with the immobilize control protein (M-PAB01) having the wild-type amino acid sequence and at a pH approximately 1.2 points higher than that of HiTrap™ rProtein A FF (GE Healthcare) (FIGS. 5 and 7). The results also demonstrated that the humanized monoclonal antibody was eluted in the M-PAB08- and M-PAB13-immobilized columns at a pH approximately 1.1 points and approximately 2.0 points, respectively, higher than that of the M-PAB01-immobilized column, in the M-PAZ08-immobilized column at a pH approximately 0.7 points higher than that of the M-PAZ01-immobilized column, and in the M-PAC08- and M-PAC13-immobilized columns at a pH approximately 1.0 points and approximately 1.7 points, respectively, higher than that of the M-PAC01-immobilized column (FIGS. 7 to 10).

9) Evaluation of Modified Protein for its Ability to Bind to Antibody Using Immobilization Column (Stepwise Method)

The elution pattern of a monoclonal antibody was examined at each pH as shown below by stepwise pH affinity chromatography using each M-PAB or M-PAZ protein-immobilized column to evaluate the modified protein A for its ability to bind to antibodies in an acidic region.

First, each M-PAB or M-PAZ protein-immobilized column was loaded to a liquid chromatography apparatus AKTA prime plus (GE Healthcare Bioscience) and equilibrated by the injection of a phosphate buffer (50 mM $Na_2HPO_4$/NaH $PO_4$ (pH 7.0)) under conditions of 0.5 mL/min. Then, 100 to 200 µL of a 1 mg/mL sample (IgG1-type humanized monoclonal antibody) was added thereto. The column was washed with 5 mL of a phosphate buffer, followed by elution with 5 mL of an elution buffer (20 mM sodium citrate, pH 4.0). Then, the column was washed with a 500 mM acetic acid solution (pH 2.5) and finally re-equilibrated with 10 mL of a phosphate buffer. The elution patterns of the human polyclonal Fc region at stepwise pHs were obtained from the output of a UV detector (280 nm) included in the liquid chromatography apparatus.

Figure 6:
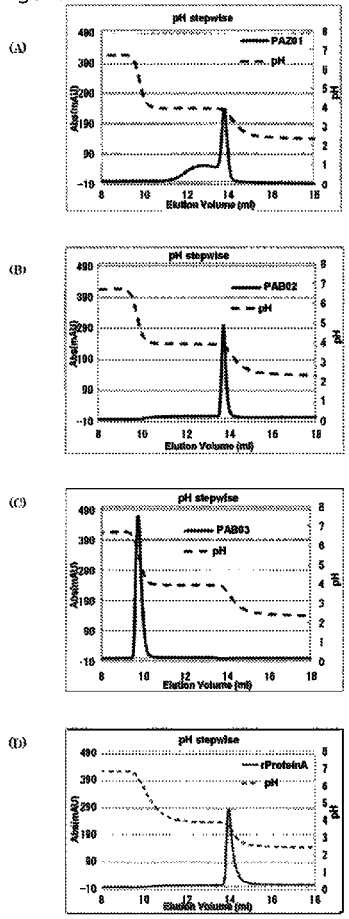
FIG. 6 is a graph showing results of evaluating (stepwise method) the ability of a modified protein to bind to antibodies in an acidic region using an immobilization column.

As a result, elution at pH 4.0 using the M-PAZ01-immobilized column caused elution in small portions at this pH and exhibited a peak at pH 3.9. Elution at pH 4.0 using the M-PAB02-immobilized column merely exhibited a peak at pH 3.9. Elution at pH 4.0 using the M-PAB03-immobilized column started elution at pH 6.4 immediately after the start of injection of an eluting solution and exhibited a peak at pH 5.7. Elution at pH 4.0 using HiTrap™ rProtein A FF (GE Healthcare) exhibited a peak at pH 3.7 (FIG. 6).

EXAMPLE 5

10) Evaluation of Modified Protein for its Ability to Bind to Antibody by Surface Plasmon Resonance Method Each M-PAB or M-PAZ protein was evaluated for its ability to bind to antibodies in a neutral region and in a weakly acidic region as shown below by a surface plasmon resonance (SPR) method.

First, an IgG1-type humanized monoclonal antibody was immobilized onto an assay cell of a sensor chip by an amine coupling method. A control cell having a carboxymethyl group blocked by ethanolamine was used as an assay control. The sensor chip used was CM5 (Biacore). Subsequently, each M-PAB or M-PAZ protein isolated and purified was dissolved in a running buffer HBS-P (10 mM HEPES (pH 7.4), 150 mM NaCl, and 0.05% v/v Surfactant P20) for a neutral region to prepare sample solutions having three concentrations of each protein. The SPR assay was conducted at a reaction temperature of 25° C. using Biacore T100 (Biacore). The collected data was analyzed using Biacore T100 Evaluation Software and fit into the 1:1 Langmuir model to calculate a dissociation equilibrium constant KD.

As a result, the modified protein M-PAZ03 was able to bind at pH 7.4 at the same level as in the control protein M-PAZ01 having the wild-type amino acid sequence, but its ability to bind to antibodies at pH 5.0 was reduced to approximately 1/25 (Table 3).

TABLE 3

| | Ability to bind to antibody | |
|---|---|---|
| Sample No. | KD at pH 7.4 (M) | KD at pH 5.0 (M) |
| M-PAB01 | $2.94 \times 10^{-10}$ | $6.71 \times 10^{-9}$ |
| M-PAB02 | $2.48 \times 10^{-10}$ | $7.36 \times 10^{-9}$ |
| M-PAB03 | $6.41 \times 10^{-9}$ | $9.88 \times 10^{-7}$ |
| M-PAB04 | $1.45 \times 10^{-10}$ | $4.91 \times 10^{-9}$ |
| M-PAB05 | $4.05 \times 10^{-10}$ | $1.14 \times 10^{-8}$ |
| M-PAB07 | $4.93 \times 10^{-10}$ | $1.93 \times 10^{-8}$ |
| M-PAB08 | $5.19 \times 10^{-9}$ | $1.31 \times 10^{-8}$ |
| M-PAZ01 | $1.32 \times 10^{-9}$ | $7.71 \times 10^{-8}$ |
| M-PAZ03 | $5.73 \times 10^{-9}$ | $1.93 \times 10^{-8}$ |

In order to further examine each M-PAB or M-PAZ protein for its ability to bind to antibodies in a neutral region and in a weakly acidic region, an evaluation test was conducted again by the SPR method.

Samples were prepared in totally the same way as above. The SPR assay was conducted at a reaction temperature of 25° C. using Biacore T100 (Biacore). The collected data was analyzed using Biacore T100 Evaluation Software and fit into the 1:1 Langmuir model to calculate a dissociation equilibrium constant KD.

In order to improve fitting accuracy, Rmax was determined in advance for pH 7.4 according to the calculation expression [Rmax=Amount of the ligand immobilized×(Molecular weight of the analyte/Molecular weight of the ligand)×The number of bindings sites in the ligand] and handled as a fixed value to perform non-linear regression calculation. As for pH 5.0, Rmax was not determined in advance and handled as a variable to perform non-linear regression calculation at the Fit Global or Fit Local mode.

As a result, the modified protein M-PAB08 or M-PAZ08 was able to bind at pH 7.4 at the same level as in the control protein M-PAB01 or M-PAZ01 having the wild-type amino acid sequence, but their ability to bind to antibodies at pH 5.0 was reduced to approximately 1/140 and approximately 1/30, respectively (Table 4). Also, M-PAB13, M-PAB14, M-PAB16, M-PAB17, or M-PAB19 exhibited large reduction in the ability to bind to antibodies at pH 5.0, which fell below the lower limit of quantification and failed to lead to the calculation of dissociation equilibrium constants.

TABLE 4

| Sample No. | Ability to bind to antibody KD at pH 7.4 (M) | KD at pH 5.0 (M) |
|---|---|---|
| M-PAB01 | $3.35 \times 10^{-9}$ | $5.29 \times 10^{-9}$ |
| M-PAB02 | $4.30 \times 10^{-9}$ | $2.28 \times 10^{-8}$ |
| M-PAB03 | $1.64 \times 10^{-8}$ | $2.52 \times 10^{-6}$ |
| M-PAB04 | $2.99 \times 10^{-9}$ | $6.90 \times 10^{-9}$ |
| M-PAB05 | $5.32 \times 10^{-9}$ | $1.15 \times 10^{-8}$ |
| M-PAB07 | $4.60 \times 10^{-9}$ | $9.68 \times 10^{-8}$ |
| M-PAB08 | $1.73 \times 10^{-8}$ | $7.52 \times 10^{-7}$ |
| M-PAB09 | $4.95 \times 10^{-9}$ | $2.84 \times 10^{-8}$ |
| M-PAB10 | $2.51 \times 10^{-8}$ | $2.89 \times 10^{-7}$ |
| M-PAB11 | $3.29 \times 10^{-9}$ | $6.11 \times 10^{-9}$ |
| M-PAB12 | $3.74 \times 10^{-9}$ | $6.99 \times 10^{-9}$ |
| M-PAB13 | $2.65 \times 10^{-7}$ | $>1 \times 10^{-5}$ |
| M-PAB14 | $4.13 \times 10^{-6}$ | $>1 \times 10^{-5}$ |
| M-PAB15 | $2.42 \times 10^{-8}$ | $7.99 \times 10^{-6}$ |
| M-PAB16 | $1.24 \times 10^{-7}$ | $>1 \times 10^{-5}$ |
| M-PAB17 | $1.89 \times 10^{-6}$ | $>1 \times 10^{-5}$ |
| M-PAB18 | $1.51 \times 10^{-8}$ | $1.59 \times 10^{-7}$ |
| M-PAB19 | $9.66 \times 10^{-8}$ | $>1 \times 10^{-5}$ |
| M-PAZ01 | $1.54 \times 10^{-8}$ | $3.94 \times 10^{-8}$ |
| M-PAZ03 | $8.56 \times 10^{-8}$ | $8.36 \times 10^{-7}$ |

11) Thermal Stability Evaluation of Modified Protein by Circular Dichroism Spectroscopy The thermal stability of each M-PAB or M-PAZ protein was evaluated as shown below by circular dichroism (CD) spectroscopy. In this context, the CD spectroscopy is known to be a spectroscopic analytical method that sensitively reflects change in the secondary structure of a protein. Molar ellipticity corresponding to the intensity of CD spectra can be observed at varying sample temperatures, thereby revealing at what temperature each modified protein A is denatured.

First, each protein isolated and purified was prepared into aqueous solutions (50 mM sodium phosphate buffer, pH 7.0) having concentrations of 5 to 25 μM. Each sample solution was injected to a cylindrical cell (cell length: 0.1 cm). A measurement wavelength was shifted from 260 nm to 195 nm at a temperature of 20° C. using a circular dichroism spectrophotometer model J805 (JASCO Corp.) to obtain CD spectra.

The same sample as above was heated to 98° C. and then cooled from 98° C. to 20° C. CD spectra were obtained at 260 nm to 195 nm. Whether or not the spectra obtained by heating followed by re-cooling are the same as spectra before heating, i.e., the rate of spectral recovery, serves as an index for reversibility for the thermal denaturation of each protein.

All of the wild-type B domain of protein A (M-PAB01) and the modified B domains of protein A (M-PAB2 to M-PAB17) rarely exhibited recovery (rate of recovery: 40% or lower), whereas the wild-type Z domain of protein A (M-PAZ01) and the modified Z domains of protein A (M-PAZ03 and M-PAZ08) exhibited sufficient recovery (rate of recovery: 60 to 90%). This means that: high or low reversibility is determined mainly by being the B domain or being the Z domain, i.e., the difference in wild-type sequence; and substitution by histidine has only a small impact on the reversibility.

Subsequently, time-dependent change in molar ellipticity was determined at a measurement wavelength fixed to 222 nm with a temperature elevated from 20° C. to 100° C. at a rate of 1° C./min. The obtained thermal melting curve was analyzed using the theoretical expression of two-dimensional phase transition models (Non Patent Literature: Arisaka, Baiosaiensu no tameno tanpakushitsu kagaku nyumon (Introduction of Protein Science for Bioscience in English) to determine a denaturation temperature Tm, and an enthalpy change dHm of denaturation at Tm.

The results demonstrated that most of the modified proteins A exhibited reduction in stability due to substitution by histidine, whereas M-PAB08 and M-PAZ08 had stability substantially equivalent to that of the control protein (M-PAB01 or M-PAZ01) having the wild-type amino acid sequence (Table 5).

TABLE 5

| Sample No. | Thermal stability Tm (K) | dHm (kJ/mol) |
|---|---|---|
| M-PAB01 | 347.1 | 290 |
| M-PAB02 | 340.5 | 108 |
| M-PAB03 | 334.5 | 170 |
| M-PAB04 | 345 | 255 |
| M-PAB05 | 343.1 | 282 |
| M-PAB07 | 341.1 | 196 |
| M-PAB08 | 346.2 | 251 |
| M-PAB09 | 344.9 | 214 |
| M-PAB10 | 342.3 | 120 |
| M-PAB13 | 343.7 | 188 |
| M-PAB14 | 343.1 | 200 |
| M-PAB15 | 339 | 174 |
| M-PAB16 | 316.2 | 124 |
| M-PAB17 | 342.5 | 212 |
| M-PAZ01 | 351.8 | 267 |

The invention claimed is:

1. A mutant protein derived from the B domain protein of protein A of the amino acid sequence set forth in SEQ ID NO: 1, the mutant protein having an amino acid sequence derived from the amino acid sequence set forth in SEQ ID NO: 1 by the substitution of the amino acid residue of Asp36 by a histidine residue, the amino acid sequence having the same length as SEQ ID NO: 1; wherein the mutant protein has a binding activity to a constant region of immunoglobulin, and has a reduced binding activity to the constant region of immunoglobulin in an acidic region of the pH scale, compared with the wild-type B domain of protein A, and wherein the amino acid derived from the amino acid sequence set forth in SEQ ID NO: 1 comprises the additional substitution of at least one of Gln9 and Gln10 by a histidine residue.

2. A mutant protein derived from the Z domain protein of protein A of the amino acid sequence set forth in SEQ ID NO: 2, the mutant protein having an amino acid sequence derived from the amino acid sequence set forth in SEQ ID NO: 2 by the substitution of the amino acid residue of Asp36 by a histidine residue, the amino acid sequence having the same length as SEQ ID NO: 2; wherein the mutant protein has a binding activity to a constant region of immunoglobulin, and has a reduced binding activity to the constant region of immunoglobulin in an acidic region of the pH scale, compared with the wild-type Z domain of protein A, and wherein the amino acid derived from the amino acid sequence set forth in SEQ ID NO: 2 comprises the additional substitution of at least one of Gln9 and Gln10 by a histidine residue.

3. A mutant protein derived from the E domain protein of protein A of the amino acid sequence set forth in SEQ ID NO: 3, the mutant protein having an amino acid sequence derived from the amino acid sequence set forth in SEQ ID NO: 3 by the substitution of the amino acid residue of Asp36 by a histidine residue, the amino acid sequence having the same length as SEQ ID NO: 3; wherein the mutant protein has a binding activity to a constant region of immunoglobulin, and has a reduced binding activity to the constant region of immunoglobulin in an acidic region of the pH scale, compared with the wild-type E domain of protein A, and wherein the amino acid derived from the amino acid sequence set forth in SEQ ID NO: 3 comprises the additional substitution of at least one of Gln9 and Gln10 by a histidine residue.

4. A mutant protein derived from the D domain protein of protein A of the amino acid sequence set forth in SEQ ID NO: 4, the mutant protein having an amino acid sequence derived from the amino acid sequence set forth in SEQ ID NO: 4 by the substitution of the amino acid residue of Asp36 by a histidine residue, the amino acid sequence having the same length as SEQ ID NO: 4; wherein the mutant protein has a binding activity to a constant region of immunoglobulin, and has a reduced binding activity to the constant region of immunoglobulin in an acidic region of the pH scale, compared with the wild-type D domain of protein A, and wherein the amino acid derived from the amino acid sequence set forth in SEQ ID NO: 4 comprises the additional substitution of at least one of Gln9 and Gln10 by a histidine residue.

5. A mutant protein derived from the A domain protein of protein A of the amino acid sequence set forth in SEQ ID NO: 5, the mutant protein having an amino acid sequence derived from the amino acid sequence set forth in SEQ ID NO:5 by the substitution of the amino acid residue of Asp36 by a histidine residue, the amino acid sequence having the same length as SEQ ID NO: 5; wherein the mutant protein has a binding activity to a constant region of immunoglobulin, and has a reduced binding activity to the constant region of immunoglobulin in an acidic region of the pH scale, compared with the wild-type A domain of protein A, and wherein the amino acid derived from the amino acid sequence set forth in SEQ ID NO: 5 comprises the additional substitution of at least one of Gln9 and Gln10 by a histidine residue.

6. A mutant protein derived from the C domain protein of protein A of the amino acid sequence set forth in SEQ ID NO: 6, the mutant protein having an amino acid sequence derived from the amino acid sequence set forth in SEQ ID NO:6 by the substitution of the amino acid residue of Asp36 by a histidine residue, the amino acid sequence having the same length as SEQ ID NO: 6; wherein the mutant protein has a binding activity to a constant region of immunoglobulin, and has a reduced binding activity to the constant region of immunoglobulin in an acidic region of the pH scale, compared with the wild-type C domain of protein A, and wherein the amino acid derived from the amino acid sequence set forth in SEQ ID NO:6 comprises the additional substitution of at least one of Gln9 and Gln10 by a histidine residue.

7. An immobilized protein comprising a protein according to any one of claims 1 to 6 immobilized on a water-insoluble solid-phase support.

8. A capturing agent for an antibody, immunoglobulin G, or a protein having a constant region of immunoglobulin, the capturing agent comprising an immobilized protein according to claim 7.

9. The mutant protein of claim 1, wherein the amino acid derived from the amino acid sequence set forth in SEQ ID NO: 1 includes the substitution of Gln9 by a histidine residue.

10. The mutant protein of claim 2, wherein the amino acid derived from the amino acid sequence set forth in SEQ ID NO: 2 includes the substitution of Gln9 by a histidine residue.

11. The mutant protein of claim 3, wherein the amino acid derived from the amino acid sequence set forth in SEQ ID NO: 3 includes the substitution of Gln9 by a histidine residue.

12. The mutant protein of claim 4, wherein the amino acid derived from the amino acid sequence set forth in SEQ ID NO: 4 includes the substitution of Gln9 by a histidine residue.

13. The mutant protein of claim 5, wherein the amino acid derived from the amino acid sequence set forth in SEQ ID NO: 5 includes the substitution of Gln9 by a histidine residue.

14. The mutant protein of claim 6, wherein the amino acid derived from the amino acid sequence set forth in SEQ ID NO: 6 includes the substitution of Gln9 by a histidine residue.

15. The mutant protein of claim 1, wherein the amino acid derived from the amino acid sequence set forth in SEQ ID NO: 1 includes the substitution of Gln10 by a histidine residue.

16. The mutant protein of claim 2, wherein the amino acid derived from the amino acid sequence set forth in SEQ ID NO: 2 includes the substitution of Gln10 by a histidine residue.

17. The mutant protein of claim 3, wherein the amino acid derived from the amino acid sequence set forth in SEQ ID NO: 3 includes the substitution of Gln10 by a histidine residue.

18. The mutant protein of claim 4, wherein the amino acid derived from the amino acid sequence set forth in SEQ ID NO: 4 includes the substitution of Gln10 by a histidine residue.

19. The mutant protein of claim 5, wherein the amino acid derived from the amino acid sequence set forth in SEQ ID NO: 5 includes the substitution of Gln10 by a histidine residue.

20. The mutant protein of claim 6, wherein the amino acid derived from the amino acid sequence set forth in SEQ ID NO: 6 includes the substitution of Gln10 by a histidine residue.

* * * * *

SEQUENCE LISTING

```
<160> NUMBER OF SEQ ID NOS: 97

<210> SEQ ID NO 1
<211> LENGTH: 58
<212> TYPE: PRT
<213> ORGANISM: Staphylococcus aureus
<220> FEATURE:
<223> OTHER INFORMATION: protein A, B domain; wild

<400> SEQUENCE: 1

Ala Asp Asn Lys Phe Asn Lys Glu Gln Gln Asn Ala Phe Tyr Glu Ile
```

```
                1               5                   10                  15
Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
            50                  55

<210> SEQ ID NO 2
<211> LENGTH: 58
<212> TYPE: PRT
<213> ORGANISM: Artificial Sequence
<220> FEATURE:
<223> OTHER INFORMATION: Artificial protein, Z domain; original

<400> SEQUENCE: 2

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
            50                  55

<210> SEQ ID NO 3
<211> LENGTH: 58
<212> TYPE: PRT
<213> ORGANISM: Staphylococcus aureus
<220> FEATURE:
<223> OTHER INFORMATION: protein A, E domain; wild

<400> SEQUENCE: 3

Asn Ala Ala Gln His Asp Glu Ala Gln Gln Asn Ala Phe Tyr Gln Val
1               5                   10                  15

Leu Asn Met Pro Asn Leu Asn Ala Asp Gln Arg Asn Gly Phe Ile Gln
            20                  25                  30

Ser Leu Lys Asp Asp Pro Ser Gln Ser Ala Asn Val Leu Gly Glu Ala
            35                  40                  45

Gln Lys Leu Asn Asp Ser Gln Ala Pro Lys
            50                  55

<210> SEQ ID NO 4
<211> LENGTH: 58
<212> TYPE: PRT
<213> ORGANISM: Staphylococcus aureus
<220> FEATURE:
<223> OTHER INFORMATION: protein A, D domain; wild

<400> SEQUENCE: 4

Gln Gln Asn Asn Phe Asn Lys Asp Gln Gln Ser Ala Phe Tyr Glu Ile
1               5                   10                  15

Leu Asn Met Pro Asn Leu Asn Glu Ala Gln Arg Asn Gly Phe Ile Gln
            20                  25                  30

Ser Leu Lys Asp Asp Pro Ser Gln Ser Thr Asn Val Leu Gly Glu Ala
            35                  40                  45

Lys Lys Leu Asn Glu Ser Gln Ala Pro Lys
            50                  55

<210> SEQ ID NO 5
```

```
<211> LENGTH: 58
<212> TYPE: PRT
<213> ORGANISM: Staphylococcus aureus
<220> FEATURE:
<223> OTHER INFORMATION: protein A, A domain; wild

<400> SEQUENCE: 5

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
        50                  55

<210> SEQ ID NO 6
<211> LENGTH: 58
<212> TYPE: PRT
<213> ORGANISM: Staphylococcus aureus
<220> FEATURE:
<223> OTHER INFORMATION: protein A, C domain; wild

<400> SEQUENCE: 6

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
        50                  55

<210> SEQ ID NO 7
<211> LENGTH: 58
<212> TYPE: PRT
<213> ORGANISM: Artificial Sequence
<220> FEATURE:
<223> OTHER INFORMATION: Mutant of protein A, B domain Asn6His,
      Asn11His, Glu15Asp, Glu24Gln, Glu25His five mutations

<400> SEQUENCE: 7

Ala Asp Asn Lys Phe His Lys Glu Gln Gln His Ala Phe Tyr Asp Ile
1               5                   10                  15

Leu His Leu Pro Asn Leu Asn Gln His Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 8
<211> LENGTH: 58
<212> TYPE: PRT
<213> ORGANISM: Artificial Sequence
<220> FEATURE:
<223> OTHER INFORMATION: Mutant of protein A, B domain Asn6His,
      Glu24His, Glu25Gln, Gln32His, Asp36His five mutations

<400> SEQUENCE: 8

Ala Asp Asn Lys Phe His Lys Glu Gln Gln Asn Ala Phe Tyr Glu Ile
1               5                   10                  15
```

```
Leu His Leu Pro Asn Leu Asn His Gln Gln Arg Asn Gly Phe Ile His
            20                  25                  30

Ser Leu Lys His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 9
<211> LENGTH: 58
<212> TYPE: PRT
<213> ORGANISM: Artificial Sequence
<220> FEATURE:
<223> OTHER INFORMATION: Mutant of protein A, Z domain Asn6His,
      Glu24His, Glu25Gln, Gln32His, Asp36His five mutations

<400> SEQUENCE: 9

Val Asp Asn Lys Phe His Lys Glu Gln Gln Asn Ala Phe Tyr Glu Ile
1               5                   10                  15

Leu His Leu Pro Asn Leu Asn His Gln Gln Arg Asn Ala Phe Ile His
            20                  25                  30

Ser Leu Lys His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 10
<211> LENGTH: 58
<212> TYPE: PRT
<213> ORGANISM: Artificial Sequence
<220> FEATURE:
<223> OTHER INFORMATION: Mutant of protein A, B domain Asn6His, single
      mutation

<400> SEQUENCE: 10

Ala Asp Asn Lys Phe His Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 11
<211> LENGTH: 58
<212> TYPE: PRT
<213> ORGANISM: Artificial Sequence
<220> FEATURE:
<223> OTHER INFORMATION: Mutant of protein A, B domain Glu24His single
      mutation

<400> SEQUENCE: 11

Ala Asp Asn Lys Phe Asn Lys Glu Gln Gln Asn Ala Phe Tyr Glu Ile
1               5                   10                  15

Leu His Leu Pro Asn Leu Asn His Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

```
<210> SEQ ID NO 12
<211> LENGTH: 58
<212> TYPE: PRT
<213> ORGANISM: Artificial Sequence
<220> FEATURE:
<223> OTHER INFORMATION: Mutant of protein A, B domain Gln32His single
      mutation

<400> SEQUENCE: 12

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile His
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 13
<211> LENGTH: 58
<212> TYPE: PRT
<213> ORGANISM: Artificial Sequence
<220> FEATURE:
<223> OTHER INFORMATION: Mutant of protein A, B domain Asp36His single
      mutation

<400> SEQUENCE: 13

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 14
<211> LENGTH: 58
<212> TYPE: PRT
<213> ORGANISM: Artificial Sequence
<220> FEATURE:
<223> OTHER INFORMATION: Mutant of protein A, B domain Phe5His, Gln9His,
      Gln10His, Asn11His, Phe13Leu, Glu15His, Glu25Asp, Arg27His,
      Asn28His, Lys35His, Asp36His eleven mutations

<400> SEQUENCE: 14

Ala Asp Asn Lys His Asn Lys Glu His His Ala Leu Tyr His Ile
1               5                   10                  15

Leu His Leu Pro Asn Leu Asn Glu Asp Gln His His Gly Phe Ile Gln
            20                  25                  30

Ser Leu His His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 15
<211> LENGTH: 58
<212> TYPE: PRT
<213> ORGANISM: Artificial Sequence
<220> FEATURE:
<223> OTHER INFORMATION: Mutant of protein A, B domain Phe5His, Asn6His,
      Gln9His, Gln10His, Asn11His, Phe13Leu, Glu15His, Glu25Asp,
      Arg27His, Asn28His, Lys35His, Asp36His twelve mutations
```

```
<400> SEQUENCE: 15

Ala Asp Asn Lys His His Lys Glu His His Ala Leu Tyr His Ile
1               5                   10                  15

Leu His Leu Pro Asn Leu Asn Glu Asp Gln His His Gly Phe Leu Gln
                20                  25                  30

Ser Leu His His Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 16
<211> LENGTH: 58
<212> TYPE: PRT
<213> ORGANISM: Artificial Sequence
<220> FEATURE:
<223> OTHER INFORMATION: Mutant of protein A, B domain Phe5His, Gln9His,
      Gln10His, Asn11His, Phe13Leu, Glu15His, Glu24Gln, Glu25Asp,
      Arg27His, Asn28His, Ile31Leu, Lys35His, Asp36His thirteen
      mutations

<400> SEQUENCE: 16

Ala Asp Asn Lys His Asn Lys Glu His His Ala Leu Tyr His Ile
1               5                   10                  15

Leu His Leu Pro Asn Leu Asn Gln Asp Gln His His Gly Phe Leu Gln
                20                  25                  30

Ser Leu His His Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 17
<211> LENGTH: 58
<212> TYPE: PRT
<213> ORGANISM: Artificial Sequence
<220> FEATURE:
<223> OTHER INFORMATION: Mutant of protein A, B domain Phe5His, Gln9His,
      Gln10His, Asn11His, Phe13Leu, Glu15Gln, Arg27His, Asn28His,
      Ile31Leu, Lys35His, Asp36His eleven mutations

<400> SEQUENCE: 17

Ala Asp Asn Lys His Asn Lys Glu His His Ala Leu Tyr Gln Ile
1               5                   10                  15

Leu His Leu Pro Asn Leu Asn Glu Glu Gln His His Gly Phe Leu Gln
                20                  25                  30

Ser Leu His His Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 18
<211> LENGTH: 58
<212> TYPE: PRT
<213> ORGANISM: Artificial Sequence
<220> FEATURE:
<223> OTHER INFORMATION: Mutant of protein A, B domain Phe5His, Gln9His,
      Gln10His, Asn11His, Phe13Leu, Gln15His, Arg27His, Asn28His,
      Ile31Leu, Lys35His, Asp36His eleven mutations

<400> SEQUENCE: 18

Ala Asp Asn Lys His Asn Lys Glu His His Ala Leu Tyr His Ile
1               5                   10                  15

Leu His Leu Pro Asn Leu Asn Glu Glu Gln His His Gly Phe Leu Gln
```

-continued

```
                 20                  25                  30

Ser Leu His His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 19
<211> LENGTH: 58
<212> TYPE: PRT
<213> ORGANISM: Artificial Sequence
<220> FEATURE:
<223> OTHER INFORMATION: Mutant of protein A, B domain Phe5His, Gln9His,
      Gln10His, Asn11His, Phe13Leu, Glu15His, Glu25Gln, Arg27His,
      Asn28His, Ile31Leu, Lys35His, Asp36His twelve mutations

<400> SEQUENCE: 19

Ala Asp Asn Lys His Asn Lys Glu His His Ala Leu Tyr His Ile
1               5                   10                  15

Leu His Leu Pro Asn Leu Asn Glu Gln Gln His His Gly Phe Leu Gln
                20                  25                  30

Ser Leu His His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 20
<211> LENGTH: 58
<212> TYPE: PRT
<213> ORGANISM: Artificial Sequence
<220> FEATURE:
<223> OTHER INFORMATION: Mutant of protein A, B domain Phe5His, Gln9His,
      Gln10His, Asn11His, Glu15His, Glu25His, Arg27His, Asn28His,
      Ile31Leu nine mutations

<400> SEQUENCE: 20

Ala Asp Asn Lys His Asn Lys Glu His His His Ala Phe Tyr His Ile
1               5                   10                  15

Leu His Leu Pro Asn Leu Asn Glu His Gln His His Gly Phe Leu Gln
                20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 21
<211> LENGTH: 58
<212> TYPE: PRT
<213> ORGANISM: Artificial Sequence
<220> FEATURE:
<223> OTHER INFORMATION: Mutant of protein A, B domain Phe5His, Gln9His,
      Gln10His, Phe13Leu, Glu15His, Glu25His, Arg27His, Ile31Leu,
      Lys35His, Asp36His ten mutations

<400> SEQUENCE: 21

Ala Asp Asn Lys His Asn Lys Glu His His Asn Ala Leu Tyr His Ile
1               5                   10                  15

Leu His Leu Pro Asn Leu Asn Glu His Gln His Asn Gly Phe Leu Gln
                20                  25                  30

Ser Leu His His Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 22
<211> LENGTH: 58
<212> TYPE: PRT
<213> ORGANISM: Artificial Sequence
<220> FEATURE:
<223> OTHER INFORMATION: Mutant of protein A, B domain Phe5His, Gln9His, Gln10His, Phe13Tyr, Glu15Asp, Leu17Gln, Glu25Asp, Arg27His, Asn28His, Ile31His, Gln32His, Lys35His, Asp36His thirteen mutations

<400> SEQUENCE: 22

Ala Asp Asn Lys His Asn Lys Glu His His Asn Ala Tyr Tyr Asp Ile
1               5                   10                  15

Gln His Leu Pro Asn Leu Asn Glu Asp Gln His His Gly Phe His His
            20                  25                  30

Ser Leu His His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 23
<211> LENGTH: 58
<212> TYPE: PRT
<213> ORGANISM: Artificial Sequence
<220> FEATURE:
<223> OTHER INFORMATION: Mutant of protein A, B domain Phe5His, Gln9His, Gln10His, Glu15Gln, Glu24Gln, Arg27His, Asn28His, Gln32His, Lys35His, Asp36His ten mutations

<400> SEQUENCE: 23

Ala Asp Asn Lys His Asn Lys Glu His His Asn Ala Phe Tyr Gln Ile
1               5                   10                  15

Leu His Leu Pro Asn Leu Asn Gln Glu Gln His His Gly Phe Ile His
            20                  25                  30

Ser Leu His His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 24
<211> LENGTH: 58
<212> TYPE: PRT
<213> ORGANISM: Artificial Sequence
<220> FEATURE:
<223> OTHER INFORMATION: Mutant of protein A, B domain Gln9His, Gln10His, Glu15Gln, Arg27His, Lys35His, Asp36His six mutations

<400> SEQUENCE: 24

Ala Asp Asn Lys Phe Asn Lys Glu His His Asn Ala Phe Tyr Gln Ile
1               5                   10                  15

Leu His Leu Pro Asn Leu Asn Glu Glu Gln His Asn Gly Phe Ile Gln
            20                  25                  30

Ser Leu His His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 25
<211> LENGTH: 58
<212> TYPE: PRT
<213> ORGANISM: Artificial Sequence
<220> FEATURE:

<223> OTHER INFORMATION: Mutant of protein A, B domain (Phe5Tyr,
      Asn6His, Gln10His, Phe13Leu, Glu15Asp, Glu24Gln, Glu25Asp,
      Asn28His, Ile31Leu, Gln32His, Lys35His, Asp36His twelve mutations)

<400> SEQUENCE: 25

```
Ala Asp Asn Lys Tyr His Lys Glu Gln His Asn Ala Leu Tyr Asp Ile
1               5                   10                  15

Leu His Leu Pro Asn Leu Asn Gln Asp Gln Arg His Gly Phe Leu His
            20                  25                  30

Ser Leu His His Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 26
<211> LENGTH: 58
<212> TYPE: PRT
<213> ORGANISM: Artificial Sequence
<220> FEATURE:
<223> OTHER INFORMATION: Mutant of protein A, B domain (Phe5Leu,
      Asn6His, Gln9His, Phe13His, Tyr14His, Glu24His, Glu25His,
      Arg27His, Gln32His, Lys35His, Asp36His eleven mutations)

<400> SEQUENCE: 26

```
Ala Asp Asn Lys Leu His Lys Glu His Gln Asn Ala His His Glu Ile
1               5                   10                  15

Leu His Leu Pro Asn Leu Asn His His Gln His Asn Gly Phe Ile His
            20                  25                  30

Ser Leu His His Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 27
<211> LENGTH: 58
<212> TYPE: PRT
<213> ORGANISM: Artificial Sequence
<220> FEATURE:
<223> OTHER INFORMATION: Mutant of protein A, B domain (Phe5Leu,
      Gln10His, Asn11His, Tyr14His, Glu15Gln, Leu17His, Glu24His,
      Glu25Gln, Ile31His, Gln32His, Lys35His, Asp36His twelve mutations)

<400> SEQUENCE: 27

```
Ala Asp Asn Lys Leu Asn Lys Glu Gln His His Ala Phe His Gln Ile
1               5                   10                  15

His His Leu Pro Asn Leu Asn His Gln Gln Arg Asn Gly Phe His His
            20                  25                  30

Ser Leu His His Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 28
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 7

<400> SEQUENCE: 28
gctgataaca aatttcacaa agaacaacaa cacgctttct atgatatcct tcatttgccg    60
aacttaaacc aacatcaacg caacggcttc attcaaagcc tgaaagatga cccaagccaa    120
agcgctaacc ttttagcaga agctaaaaag ctaaatgatg cacaagcacc aaaa          174

<210> SEQ ID NO 29
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 8

<400> SEQUENCE: 29
gctgataaca aatttcataa agaacaacaa aatgctttct atgaaatcct gcatttgccg    60
aacttaaacc atcaacaacg taacggcttc attcatagcc tgaaacatga cccaagccaa    120
agcgctaatc ttttagcaga agctaaaaag ctaaatgatg cacaagcacc aaaa          174

<210> SEQ ID NO 30
<211> LENGTH: 174
<212> TYPE: DNA
<213> ORGANISM: Artificial Sequence
<220> FEATURE:
<223> OTHER INFORMATION: Polynucleotide encoding Protein A, Z domain
      mutant of SEQUENCE 9

<400> SEQUENCE: 30
gtggataaca aatttcataa agaacaacaa aacgctttct atgaaatctt acatttgccg    60
aacttaaacc atcaacaacg caacgcgttc attcatagct taaaacatga cccaagccaa    120
agcgctaacc ttttagcaga agctaaaaag ctaaatgatg cacaagcacc aaaa          174

<210> SEQ ID NO 31
<211> LENGTH: 1551
<212> TYPE: DNA
<213> ORGANISM: Staphylococcus aureus
<220> FEATURE:
<223> OTHER INFORMATION: subsp. aureus NCTC8325strain (protein A gene)

<400> SEQUENCE: 31
ttatagttcg cgacgacgtc cagctaataa cgctgcacct aaggctaatg ataatccacc    60
aaatacagtt gtaccgatga atggattttc ttcaccagtt tctggtaatg cttgagcttt    120
gttagcatct gcatggtttg ctggttgctt cttatcaaca acaagttctt gaccaggttt    180
gatcatgttt ttatcagcta atttgttatc tgcagcaatt ttgtcagcag tagtgccgtt    240
tgcttttgca atgtcattta ctgtatcacc aggtttaacg acatgtactc cgttaccatc    300
ttctttacca ggtttgttgc atcttctttt gccaggcttg ttgccgtctt ctttaccagg    360 tttttttgttg tcttctttac caggcttgtt gccatcttct ttaccaggtt ttttgttgtc    420
ttctttacca ggcttgttgc cgtcttcttt gccaggcttg ttgttgtctt ctttaccagg    480
cttgttgttg tcttctttac caggcttgtt gttgtcttct tgccaggct tgttattgtc     540 ttctttgcca ggcttgttat tgtcttcctc ttttggtgct tgagcatcgt ttagcttttt    600
agcttctgct aaaatttctt tgctcactga aggatcgtct ttaaggcttt ggatgaagcc    660
gttacgttgt tctcagtta agttaggtaa atgtaaaatt tcatagaaag cattttgttg    720
ttctttgttg aatttgttgt cagcttttgg tgcttgagca tcatttagct ttttagcttc    780
tgctaaaagg ttagcgcttt ggctgggtc atcttttagg ctttggatga aaccattgcg    840
ttgttcttcg tttaagttag gtaaatgtaa gatttcatag aaagcatttt gttgttcttt    900
gttgaatttg ttatccgctt tcggtgcttg agattcattt aactttttag cttctgacaa    960

```
taggttagca ctttggcttg ggtcatcttt taagctttgg atgaaaccat tgcgttgttc     1020
ttcgtttaag ttaggcatat tcaagatttc atagaaagca ttttgttgtt ctttgttgaa     1080
attgttatca gctttcggtg cttgagattc gtttaatttt ttagcttcac ctaaaacgtt     1140
agtgctttgg cttgggtcgt ctttaagact ttgaatgaag ccgttacgtt gcgcttcgtt     1200
taagttaggc atgttcaaga tttcatagaa ggcgctttgt tgatctttgt tgaagttatt     1260
ttgttgcgca tcagcttttg gagcttgaga gtcattaagt ttttgagctt cacctaaaac     1320
gttagcactt tggcttggat catctttaag gctttggata aaccattgc gttgatcagc      1380 atttaagtta ggcatattta agacttgata aaaagcattt tgttgagctt catcgtgttg     1440
cgcagcattt gcagcaggtg ttacgccacc agatataagt aatgtaccta aagttacaga     1500 tgcaataccct acacctagtt tacgaattga ataaatgttt tctttttca a              1551

<210> SEQ ID NO 32
<211> LENGTH: 39
<212> TYPE: DNA
<213> ORGANISM: Artificial Sequence
<220> FEATURE:
<223> OTHER INFORMATION: Polynucleotide for Protein A mutant library

<400> SEQUENCE: 32
ccgaattccg gcggtggagg ctccatggct gataacaaa                            39

<210> SEQ ID NO 33
<211> LENGTH: 81
<212> TYPE: DNA
<213> ORGANISM: Artificial Sequence
<220> FEATURE:
<223> OTHER INFORMATION: Polynucleotide for Protein A mutant library

<400> SEQUENCE: 33
gtttaagttc ggcaaatgmw ggatwtsatr rwragcrtkw tgwtgttctt trtkawrttt      60
gttatcagcc atggagcctc c                                               81

<210> SEQ ID NO 34
<211> LENGTH: 78
<212> TYPE: DNA
<213> ORGANISM: Artificial Sequence
<220> FEATURE:
<223> OTHER INFORMATION: Polynucleotide for Protein A mutant library

<400> SEQUENCE: 34
catttgccga acttaaacsa wsawcaacry mayggcttcm wtcawagcct gmawsatgac      60
ccaagccaaa gcgctaac                                                   78

<210> SEQ ID NO 35
<211> LENGTH: 81
<212> TYPE: DNA
<213> ORGANISM: Artificial Sequence
<220> FEATURE:
<223> OTHER INFORMATION: Polynucleotide for Protein A mutant library

<400> SEQUENCE: 35
cgcaagcttg tcttattttg gtgcttgtgc atcatttagc ttttagctt ctgctaaaag       60 gttagcgctt tggcttgggt c                                               81

<210> SEQ ID NO 36
<211> LENGTH: 17
<212> TYPE: DNA
```

```
<213> ORGANISM: Artificial Sequence
<220> FEATURE:
<223> OTHER INFORMATION: primer

<400> SEQUENCE: 36
gtggtcttcg cccagaa                                                17

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
cgcaagcttg tcttattttg gtgc                                        24

<210> SEQ ID NO 38
<211> LENGTH: 46
<212> TYPE: DNA
<213> ORGANISM: Artificial Sequence
<220> FEATURE:
<223> OTHER INFORMATION: primer

<400> SEQUENCE: 38
agaaggagat ataccatggc tgataacaaa tttaacaaag aacaac                46

<210> SEQ ID NO 39
<211> LENGTH: 45
<212> TYPE: DNA
<213> ORGANISM: Artificial Sequence
<220> FEATURE:
<223> OTHER INFORMATION: primer

<400> SEQUENCE: 39
catatggctg ataacaaatt tcataaagaa caacaaaacg ctttc                 45

<210> SEQ ID NO 40
<211> LENGTH: 36
<212> TYPE: DNA
<213> ORGANISM: Artificial Sequence
<220> FEATURE:
<223> OTHER INFORMATION: primer

<400> SEQUENCE: 40
catttgccga acttaaacca tgaacaacgc aacggc                           36

<210> SEQ ID NO 41
<211> LENGTH: 35
<212> TYPE: DNA
<213> ORGANISM: Artificial Sequence
<220> FEATURE:
<223> OTHER INFORMATION: primer

<400> SEQUENCE: 41
cgcaacggct tcattcatag cttaaaagat gaccc                            35

<210> SEQ ID NO 42
<211> LENGTH: 34
<212> TYPE: DNA
<213> ORGANISM: Artificial Sequence
<220> FEATURE:
<223> OTHER INFORMATION: primer

<400> SEQUENCE: 42
cattcagagc ttaaaacatg acccaagcca aagc                             34
```

<210> SEQ ID NO 43
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 14

<400> SEQUENCE: 43
gctgataaca aacataacaa agaacatcat catgctcttt atcatatcct gcatttgccg     60
aacctaaacg aagatcaaca ccatggcttc attcaaagcc tgcatcatga cccaagccaa    120
agcgctaacc ttttagcaga agctaaaaag ctaaatgatg cacaagcacc aaaa          174

<210> SEQ ID NO 44
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 15

<400> SEQUENCE: 44
gctgataaca aacatcacaa agaacatcat catgctcttt atcatatcct gcatttgccg     60
aacctaaacg aagatcaaca ccatggcttc attcaaagcc tgcatcatga cccaagccaa    120
agcgctaacc ttttagcaga agctaaaaag ctaaatgatg cacaagcacc aaaa          174

<210> SEQ ID NO 45
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 16

<400> SEQUENCE: 45
gctgataaca aacataacaa agaacatcat cacgctcttt atcatatcct gcatttgccg     60
aacttaaacc aagatcaaca ccatggcttc cttcaaagcc tgcatcatga cccaagccaa    120
agcgctaacc ttttagcaga agctaaaaag ctaaatgatg cacaagcacc aaaa          174

<210> SEQ ID NO 46
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 17

<400> SEQUENCE: 46
gctgataaca aacataacaa agaacatcat cacgctcttt atcaaatcct tcatttgccg     60
aacttaaacg aagaacaaca ccatggcttc cttcaaagcc tgcatcatga cccaagccaa    120
agcgctaacc ttttagcaga agctaaaaag ctaaatgatg cacaagcacc aaaa          174

<210> SEQ ID NO 47
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 18

<400> SEQUENCE: 47
gctgataaca aacataataa agaacatcat catgctcttt atcatatcct gcatttgccg    60
aacttaaacg aagaacaaca ccatggcttc cttcaaagcc tgcatcatga cccaagccaa   120
agcgctaacc ttttagcaga agctaaaaag ctaaatgatg cacaagcacc aaaa         174

<210> SEQ ID NO 48
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 19

<400> SEQUENCE: 48
gctgataaca aacataataa agaacatcat catgctcttt atcatatcct tcatttgccg    60
aacttaaacg aacaacaaca tcacggcttc cttcaaagcc tgcatcatga cccaagccaa   120
agcgctaacc ttttagcaga agctaaaaag ctaaatgatg cacaagcacc aaaa         174

<210> SEQ ID NO 49
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 20

<400> SEQUENCE: 49
gctgataaca aacataataa agaacatcat catgcttttt atcatatcct gcatttgccg    60
aacttaaacg aacatcaaca tcacggcttc cttcaaagcc tgaaagatga cccaagccaa   120
agcgctaacc ttttagcaga agctaaaaag ctaaatgatg cacaagcacc aaaa         174

<210> SEQ ID NO 50
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 21

<400> SEQUENCE: 50
gctgataaca aacataacaa agaacatcat aatgctctct atcatatcct tcatttgccg    60
aacttaaacg aacatcaaca caatggcttc cttcaaagcc tgcatcatga cccaagccaa   120
agcgctaacc ttttagcaga agctaaaaag ctaaatgatg cacaagcacc aaaa         174

<210> SEQ ID NO 51
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 22

<400> SEQUENCE: 51
gctgataaca aacataacaa agaacatcat aacgcttatt atgatatcca gcatttgccg    60
aacttaaacg aagatcaaca ccatggcttc catcatagcc tgcatcatga cccaagccaa   120
agcgctaacc ttttagcaga agctaaaaag ctaaatgatg cacaagcacc aaaa         174

<210> SEQ ID NO 52
<211> LENGTH: 174
<212> TYPE: DNA

```
<213> ORGANISM: Artificial Sequence
<220> FEATURE:
<223> OTHER INFORMATION: Polynucleotide encoding Protein A, B domain
      mutant of SEQUENCE 23

<400> SEQUENCE: 52
gctgataaca acataacaa agaacatcat aacgctttct atcaaatcct tcatttgccg      60
aacttaaacc aagaacaaca tcacggcttc attcatagcc tgcatcatga cccaagccaa     120
agcgctaacc ttttagcaga agctaaaaag ctaaatgatg cacaagcacc aaaa           174

<210> SEQ ID NO 53
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 24

<400> SEQUENCE: 53
gctgataaca aatttaacaa agaacatcat aatgcttttt atcaaatcct gcatttgccg      60
aacttaaacg aagaacaaca caacggcttc attcaaagcc tgcatcatga cccaagccaa     120
agcgctaacc ttttagcaga agctaaaaag ctaaatgatg cacaagcacc aaaa           174

<210> SEQ ID NO 54
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 25

<400> SEQUENCE: 54
gctgataaca aatatcacaa agaacaacat aacgctcttt atgatatcct tcatttgccg      60
aacttaaacc aagatcaacg ccatggcttc cttcatagcc tgcatcatga cccaagccaa     120
agcgctaacc ttttagcaga agctaaaaag ctaaatgatg cacaagcacc aaaa           174

<210> SEQ ID NO 55
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 26

<400> SEQUENCE: 55
gctgataaca aacttcacaa agaacatcaa aatgctcacc atgaaatcct gcatttgccg      60
aacttaaacc atcatcaaca caacggcttc attcatagcc tgcatcatga cccaagccaa     120
agcgctaacc ttttagcaga agctaaaaag ctaaatgatg cacaagcacc aaaa           174

<210> SEQ ID NO 56
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 27

<400> SEQUENCE: 56
gctgataaca aacttaataa agaacaacat cacgctttcc atcaaatcca tcatttgccg      60
aacttaaacc atcaacaacg taatggcttc catcatagcc tgcatcatga cccaagccaa     120
```
agcgctaacc ttttagcaga agctaaaaag ctaaatgatg cacaagcacc aaaa    174

<210> SEQ ID NO 57
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 10

<400> SEQUENCE: 57
gctgataaca aatttcataa agaacaacaa aacgctttct atgaaatctt acatttacct    60
aacttaaacg aagaacaacg caatggcttc attcagagct aaaagatga cccaagccaa    120 agcgctaacc ttttagcaga agctaaaaag ctaaatgatg cacaagcacc aaaa    174

<210> SEQ ID NO 58
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 11

<400> SEQUENCE: 58
gctgataaca aatttaacaa agaacaacaa aatgctttct atgaaatctt acatttgccg    60
aacttaaacc atgaacaacg caacggcttc attcagagct aaaagatga cccaagccaa    120 agcgctaacc ttttagcaga agctaaaaag ctaaatgatg cacaagcacc aaaa    174

<210> SEQ ID NO 59
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 12

<400> SEQUENCE: 59
gctgataaca aatttaacaa agaacaacaa aatgctttct atgaaatctt acatttacct    60
aacttaaacg aagaacaacg caatggcttc attcatagct aaaagatga cccaagccaa    120 agcgctaacc ttttagcaga agctaaaaag ctaaatgatg cacaagcacc aaaa    174

<210> SEQ ID NO 60
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 13

<400> SEQUENCE: 60
gctgataaca aatttaacaa agaacaacaa aatgctttct atgaaatctt acatttacct    60
aacttaaacg aagaacaacg caatggcttc attcagagct aaaacatga cccaagccaa    120 agcgctaacc ttttagcaga agctaaaaag ctaaatgatg cacaagcacc aaaa    174

<210> SEQ ID NO 61
<211> LENGTH: 58
<212> TYPE: PRT
<213> ORGANISM: Artificial Sequence
<220> FEATURE:
<223> OTHER INFORMATION: Mutant of protein A, B domain Gln94His single
      mutation PAB09

```
<400> SEQUENCE: 61

Ala Asp Asn Lys Phe Asn Lys Glu His Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 62
<211> LENGTH: 58
<212> TYPE: PRT
<213> ORGANISM: Artificial Sequence
<220> FEATURE:
<223> OTHER INFORMATION: Mutant of protein A, B domain Gln10His single
      mutation PAB10

<400> SEQUENCE: 62

Ala Asp Asn Lys Phe Asn Lys Glu Gln His Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 63
<211> LENGTH: 58
<212> TYPE: PRT
<213> ORGANISM: Artificial Sequence
<220> FEATURE:
<223> OTHER INFORMATION: Mutant of protein A, B domain Glu15His single
      mutation PAB11

<400> SEQUENCE: 63

Ala Asp Asn Lys Phe Asn Lys Glu Gln Gln Asn Ala Phe Tyr His Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 64
<211> LENGTH: 58
<212> TYPE: PRT
<213> ORGANISM: Artificial Sequence
<220> FEATURE:
<223> OTHER INFORMATION: Mutant of protein A, B domain Arg27His single
      mutation PAB12

<400> SEQUENCE: 64

Ala Asp Asn Lys Phe Asn Lys Glu Gln Gln Asn Ala Phe Tyr Glu Ile
1               5                   10                  15

Leu His Leu Pro Asn Leu Asn Glu Glu Gln His Asn Gly Phe Ile Gln
            20                  25                  30

Ser Leu Lys Asp Asp Pro Ser Gln Ser Ala Asn Leu Leu Ala Glu Ala
        35                  40                  45
```

```
Lys Lys Leu Asn Asp Ala Gln Ala Pro Lys
    50                  55

<210> SEQ ID NO 65
<211> LENGTH: 58
<212> TYPE: PRT
<213> ORGANISM: Artificial Sequence
<220> FEATURE:
<223> OTHER INFORMATION: Mutant of protein A, B domain Gln9His Asp36His
      two mutations PAB13

<400> SEQUENCE: 65

Ala Asp Asn Lys Phe Asn Lys Glu His Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 66
<211> LENGTH: 58
<212> TYPE: PRT
<213> ORGANISM: Artificial Sequence
<220> FEATURE:
<223> OTHER INFORMATION: Mutant of protein A, B domain Gln10His Asp36His
      two mutations PAB14

<400> SEQUENCE: 66

Ala Asp Asn Lys Phe Asn Lys Glu Gln His Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 67
<211> LENGTH: 58
<212> TYPE: PRT
<213> ORGANISM: Artificial Sequence
<220> FEATURE:
<223> OTHER INFORMATION: Mutant of protein A, B domain Glu15His Asp36His
      two mutations PAB15

<400> SEQUENCE: 67

Ala Asp Asn Lys Phe Asn Lys Glu Gln Gln Asn Ala Phe Tyr His Ile
1               5                   10                  15

Leu His Leu Pro Asn Leu Asn Glu Glu Gln Arg Asn Gly Phe Ile Gln
            20                  25                  30

Ser Leu Lys His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 68
<211> LENGTH: 58
<212> TYPE: PRT
<213> ORGANISM: Artificial Sequence
<220> FEATURE:
```

-continued

<223> OTHER INFORMATION: Mutant of protein A, B domain Arg27His Asp36His
     two mutations PAB16

<400> SEQUENCE: 68

Ala Asp Asn Lys Phe Asn Lys Glu Gln Gln Asn Ala Phe Tyr Glu Ile
1               5                   10                  15

Leu His Leu Pro Asn Leu Asn Glu Glu Gln His Asn Gly Phe Ile Gln
            20                  25                  30

Ser Leu Lys His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 69
<211> LENGTH: 58
<212> TYPE: PRT
<213> ORGANISM: Artificial Sequence
<220> FEATURE:
<223> OTHER INFORMATION: Mutant of protein A, B domain Lys35His Asp36His
     two mutations PAB17

<400> SEQUENCE: 69

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu His His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 70
<211> LENGTH: 58
<212> TYPE: PRT
<213> ORGANISM: Artificial Sequence
<220> FEATURE:
<223> OTHER INFORMATION: Mutant of protein A, B domain Gln9His Gln32His
     two mutations PAB18

<400> SEQUENCE: 70

Ala Asp Asn Lys Phe Asn Lys Glu His Gln Asn Ala Phe Tyr Glu Ile
1               5                   10                  15

Leu His Leu Pro Asn Leu Asn Glu Glu Gln Arg Asn Gly Phe Ile His
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 71
<211> LENGTH: 58
<212> TYPE: PRT
<213> ORGANISM: Artificial Sequence
<220> FEATURE:
<223> OTHER INFORMATION: Mutant of protein A, B domain Gln10His Gln32His
     two mutations PAB19

<400> SEQUENCE: 71

Ala Asp Asn Lys Phe Asn Lys Glu Gln His Asn Ala Phe Tyr Glu Ile
1               5                   10                  15

Leu His Leu Pro Asn Leu Asn Glu Glu Gln Arg Asn Gly Phe Ile His
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 72
<211> LENGTH: 58
<212> TYPE: PRT
<213> ORGANISM: Artificial Sequence
<220> FEATURE:
<223> OTHER INFORMATION: Mutant of protein A, Z domain Asp36His single
      mutation PAZ08

<400> SEQUENCE: 72

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys His Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 73
<211> LENGTH: 58
<212> TYPE: PRT
<213> ORGANISM: Staphylococcus aureus
<220> FEATURE:
<223> OTHER INFORMATION: protein A, C domain; wild PAC01

<400> SEQUENCE: 73

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 74
<211> LENGTH: 58
<212> TYPE: PRT
<213> ORGANISM: Artificial Sequence
<220> FEATURE:
<223> OTHER INFORMATION: Mutant of protein A, C domain Asp36His single
      mutation PAC08

<400> SEQUENCE: 74

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys His Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 75
<211> LENGTH: 58
<212> TYPE: PRT

<213> ORGANISM: Artificial Sequence
<220> FEATURE:
<223> OTHER INFORMATION: Mutant of protein A, C domain Gln9His single mutation PAC09

<400> SEQUENCE: 75

Ala Asp Asn Lys Phe Asn Lys Glu His Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 76
<211> LENGTH: 58
<212> TYPE: PRT
<213> ORGANISM: Artificial Sequence
<220> FEATURE:
<223> OTHER INFORMATION: Mutant of protein A, C domain Gln9His Asp36His two mutations PAC13

<400> SEQUENCE: 76

Ala Asp Asn Lys Phe Asn Lys Glu His Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys His Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 77
<211> LENGTH: 174
<212> TYPE: DNA
<213> ORGANISM: Artificial Sequence
<220> FEATURE:
<223> OTHER INFORMATION: Polynucleotide encoding Protein A, B domain mutant of SEQUENCE 61

<400> SEQUENCE: 77
gctgataaca aatttaacaa agaacatcaa aatgctttct atgaaatctt acatttacct    60
aacttaaacg aagaacaacg caatggcttc attcagagct aaaagatga cccaagccaa   120 agcgctaacc ttttagcaga agctaaaaag ctaaatgatg cacaagcacc aaaa          174

<210> SEQ ID NO 78
<211> LENGTH: 174
<212> TYPE: DNA
<213> ORGANISM: Artificial Sequence
<220> FEATURE:
<223> OTHER INFORMATION: Polynucleotide encoding Protein A, B domain mutant of SEQUENCE 62

<400> SEQUENCE: 78
gctgataaca aatttaacaa agaacaacat aatgctttct atgaaatctt acatttacct    60
aacttaaacg aagaacaacg caatggcttc attcagagct aaaagatga cccaagccaa   120 agcgctaacc ttttagcaga agctaaaaag ctaaatgatg cacaagcacc aaaa          174

<210> SEQ ID NO 79
<211> LENGTH: 174

```
<212> TYPE: DNA
<213> ORGANISM: Artificial Sequence
<220> FEATURE:
<223> OTHER INFORMATION: Polynucleotide encoding Protein A, B domain
      mutant of SEQUENCE 63

<400> SEQUENCE: 79
gctgataaca aatttaacaa agaacaacaa aatgctttct atcatatctt acatttacct      60
aacttaaacg aagaacaacg caatggcttc attcagagct taaaagatga cccaagccaa     120
agcgctaacc ttttagcaga agctaaaaag ctaaatgatg cacaagcacc aaaa           174

<210> SEQ ID NO 80
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 64

<400> SEQUENCE: 80
gctgataaca aatttaacaa agaacaacaa aatgctttct atgaaatctt acatttacct      60
aacttaaacg aagaacaaca taatggcttc attcagagct taaaagatga cccaagccaa     120
agcgctaacc ttttagcaga agctaaaaag ctaaatgatg cacaagcacc aaaa           174

<210> SEQ ID NO 81
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 65

<400> SEQUENCE: 81
gctgataaca aatttaacaa agaacatcaa aatgctttct atgaaatctt acatttacct      60
aacttaaacg aagaacaacg caatggcttc attcagagct taaaacatga cccaagccaa     120
agcgctaacc ttttagcaga agctaaaaag ctaaatgatg cacaagcacc aaaa           174

<210> SEQ ID NO 82
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 66

<400> SEQUENCE: 82
gctgataaca aatttaacaa agaacaacat aatgctttct atgaaatctt acatttacct      60
aacttaaacg aagaacaacg caatggcttc attcagagct taaaacatga cccaagccaa     120
agcgctaacc ttttagcaga agctaaaaag ctaaatgatg cacaagcacc aaaa           174

<210> SEQ ID NO 83
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 67

<400> SEQUENCE: 83
gctgataaca aatttaacaa agaacaacaa aatgctttct atcatatctt acatttacct      60
aacttaaacg aagaacaacg caatggcttc attcagagct taaaacatga cccaagccaa     120
```

<210> SEQ ID NO 84
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 68

<400> SEQUENCE: 84

```
gctgataaca aatttaacaa agaacaacaa aatgctttct atgaaatctt acatttacct     60 aacttaaaacg aagaacaaca taatggcttc attcagagct aaaacatga cccaagccaa    120 agcgctaacc ttttagcaga agctaaaaag ctaaatgatg cacaagcacc aaaa          174
```

<210> SEQ ID NO 85
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 69

<400> SEQUENCE: 85

```
gctgataaca aatttaacaa agaacaacaa aatgctttct atgaaatctt acatttacct     60 aacttaaaacg aagaacaacg caatggcttc attcagagct tacatcatga cccaagccaa   120
agcgctaacc ttttagcaga agctaaaaag ctaaatgatg cacaagcacc aaaa          174
```

<210> SEQ ID NO 86
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 70

<400> SEQUENCE: 86

```
gctgataaca aatttaacaa agaacatcaa aatgctttct atgaaatctt acatttacct     60 aacttaaaacg aagaacaacg caatggcttc attcatagct taaaagatga cccaagccaa   120
agcgctaacc ttttagcaga agctaaaaag ctaaatgatg cacaagcacc aaaa          174
```

<210> SEQ ID NO 87
<211> LENGTH: 174
<212> TYPE: DNA
<213> ORGANISM: Artificial Sequence
<220> FEATURE:
<223> OTHER INFORMATION: Polynucleotide encoding Protein A, B domain
      mutant of SEQUENCE 71

<400> SEQUENCE: 87

```
gctgataaca aatttaacaa agaacaacat aatgctttct atgaaatctt acatttacct     60 aacttaaaacg aagaacaacg caatggcttc attcatagct taaaagatga cccaagccaa   120
agcgctaacc ttttagcaga agctaaaaag ctaaatgatg cacaagcacc aaaa          174
```

<210> SEQ ID NO 88
<211> LENGTH: 174
<212> TYPE: DNA
<213> ORGANISM: Artificial Sequence
<220> FEATURE:
<223> OTHER INFORMATION: Polynucleotide encoding Protein A, Z domain
      mutant of SEQUENCE 72

<400> SEQUENCE: 88
gtggataaca aatttaacaa agaacaacaa aatgctttct atgaaatctt acatttacct        60
aacttaaacg aagaacaacg caatgcgttc attcagagct aaaacatga cccaagccaa        120 agcgctaacc ttttagcaga agctaaaaag ctaaatgatg cacaagcacc aaaa            174

<210> SEQ ID NO 89
<211> LENGTH: 174
<212> TYPE: DNA
<213> ORGANISM: Artificial Sequence
<220> FEATURE:
<223> OTHER INFORMATION: Polynucleotide encoding Protein A, C domain
      mutant of SEQUENCE 74

<400> SEQUENCE: 89
gctgataaca aatttaacaa agaacaacaa aatgctttct atgaaatctt acatttacct        60
aacttaaccg aagaacaacg caatggcttc attcagagct aaaacatga cccaagcgtg        120 agcaaagaaa ttttagcaga agctaaaaag ctaaatgatg cacaagcacc aaaa            174

<210> SEQ ID NO 90
<211> LENGTH: 174
<212> TYPE: DNA
<213> ORGANISM: Artificial Sequence
<220> FEATURE:
<223> OTHER INFORMATION: Polynucleotide encoding Protein A, C domain
      mutant of SEQUENCE 75

<400> SEQUENCE: 90
gctgataaca aatttaacaa agaacatcaa aatgctttct atgaaatctt acatttacct        60
aacttaaccg aagaacaacg caatggcttc attcagagct aaagatga cccaagcgtg         120 agcaaagaaa ttttagcaga agctaaaaag ctaaatgatg cacaagcacc aaaa            174

<210> SEQ ID NO 91
<211> LENGTH: 174
<212> TYPE: DNA
<213> ORGANISM: Artificial Sequence
<220> FEATURE:
<223> OTHER INFORMATION: Polynucleotide encoding Protein A, C domain
      mutant of SEQUENCE 76

<400> SEQUENCE: 91
gctgataaca aatttaacaa agaacatcaa aatgctttct atgaaatctt acatttacct        60
aacttaaccg aagaacaacg caatggcttc attcagagct aaaacatga cccaagcgtg        120 agcaaagaaa ttttagcaga agctaaaaag ctaaatgatg cacaagcacc aaaa            174

<210> SEQ ID NO 92
<211> LENGTH: 45
<212> TYPE: DNA
<213> ORGANISM: Artificial Sequence
<220> FEATURE:
<223> OTHER INFORMATION: primer

<400> SEQUENCE: 92
gataacaaat ttaacaaaga acatcaaaac gctttctatg aaatc                       45

<210> SEQ ID NO 93
<211> LENGTH: 46
<212> TYPE: DNA
<213> ORGANISM: Artificial Sequence
<220> FEATURE:
<223> OTHER INFORMATION: primer

<400> SEQUENCE: 93
aacaaattta acaaagaaca acataatgct ttctatgaaa tcttac                         46

<210> SEQ ID NO 94
<211> LENGTH: 45
<212> TYPE: DNA
<213> ORGANISM: Artificial Sequence
<220> FEATURE:
<223> OTHER INFORMATION: primer

<400> SEQUENCE: 94
gaacaacaaa atgctttcta tcatatctta catttaccta actta                          45

<210> SEQ ID NO 95
<211> LENGTH: 42
<212> TYPE: DNA
<213> ORGANISM: Artificial Sequence
<220> FEATURE:
<223> OTHER INFORMATION: primer

<400> SEQUENCE: 95
ccgaacttaa acgaagaaca acataacggc ttcattcaga gc                             42

<210> SEQ ID NO 96
<211> LENGTH: 39
<212> TYPE: DNA
<213> ORGANISM: Artificial Sequence
<220> FEATURE:
<223> OTHER INFORMATION: primer

<400> SEQUENCE: 96
ggcttcattc agagcttaca tcatgaccca agccaaagc                                 39

<210> SEQ ID NO 97
<211> LENGTH: 1551
<212> TYPE: DNA
<213> ORGANISM: Staphylococcus aureus
<220> FEATURE:
<223> OTHER INFORMATION: subsp. aureus NCTC8325strain (protein A gene)
      reverse complement

<400> SEQUENCE: 97
ttgaaaaaga aaacattta ttcaattcgt aaactaggtg taggtattgc atctgtaact           60
ttaggtacat tacttatatc tggtggcgta acacctgctg caaatgctgc gcaacacgat         120
gaagctcaac aaaatgcttt ttatcaagtc ttaaatatgc ctaacttaaa tgctgatcaa         180
cgcaatggtt ttatccaaag ccttaaagat gatccaagcc aaagtgctaa cgttttaggt         240
gaagctcaaa aacttaatga ctctcaagct ccaaaagctg atgcgcaaca aaataacttc         300
aacaaagatc aacaaagcgc cttctatgaa atcttgaaca tgcctaactt aaacgaagcg         360
caacgtaacg gcttcattca agtcttaaaa gacgacccaa gccaaagcac taacgtttta         420
ggtgaagcta aaaaattaaa cgaatctcaa gcaccgaaag ctgataacaa tttcaacaaa         480
gaacaacaaa atgctttcta tgaaatcttg aatatgccta acttaaacga agaacaacgc         540 aatggttttca tccaaagctt aaaagatgac ccaagccaaa gtgctaacct attgtcagaa         600
gctaaaaagt taaatgaatc tcaagcaccg aaagcggata caaattcaa caaagaacaa         660 caaaatgctt tctatgaaat cttcatttta cctaacttaa acgaagaaca acgcaatggt         720
ttcatccaaa gcctaaaaga tgacccaagc caaagcgcta acctttttagc agaagctaaa         780 aagctaaatg atgctcaagc accaaaagct gacaacaaat tcaacaaaga acaacaaaat         840

```
gctttctatg aaattttaca tttacctaac ttaactgaag aacaacgtaa cggcttcatc    900
caaagcctta aagacgatcc ttcagtgagc aaagaaattt tagcagaagc taaaaagcta    960
aacgatgctc aagcaccaaa agaggaagac aataacaagc ctggcaaaga agacaataac   1020
aagcctggca aagaagacaa caacaagcct ggtaaagaag acaacaacaa gcctggtaaa   1080
gaagacaaca acaagcctgg caaagaagac ggcaacaagc ctggtaaaga agacaacaaa   1140
aaacctggta aagaagatgg caacaagcct ggtaaagaag acaacaaaaa acctggtaaa   1200
gaagacggca acaagcctgg caaagaagat ggcaacaaac ctggtaaaga agatggtaac   1260
ggagtacatg tcgttaaacc tggtgataca gtaaatgaca ttgcaaaagc aaacggcact   1320
actgctgaca aaattgctgc agataacaaa ttagctgata aaaacatgat caaacctggt   1380
caagaacttg ttgttgataa gaagcaacca gcaaaccatg cagatgctaa caaagctcaa   1440
gcattaccag aaactggtga agaaaatcca ttcatcggta caactgtatt tggtggatta   1500
tcattagcct taggtgcagc gttattagct ggacgtcgtc gcgaactata a            1551
```